US009568486B2

(12) United States Patent
Speicher et al.

(10) Patent No.: US 9,568,486 B2
(45) Date of Patent: Feb. 14, 2017

(54) METHODS AND COMPOSITIONS FOR DIAGNOSIS OF ECTOPIC PREGNANCY

(75) Inventors: David W Speicher, Berwyn, PA (US); Kurt T. Barnhart, Bryn Mawr, PA (US); Lynn A. Beer, Medford, NJ (US)

(73) Assignees: THE WISTAR INSTITUTE OF ANATOMY AND BIOLOGY, Philadelphia, PA (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 129 days.

(21) Appl. No.: 13/397,442

(22) Filed: Feb. 15, 2012

(65) Prior Publication Data
US 2012/0214685 A1 Aug. 23, 2012

Related U.S. Application Data

(60) Provisional application No. 61/443,026, filed on Feb. 15, 2011.

(51) Int. Cl.
*G01N 33/76* (2006.01)
*G01N 33/68* (2006.01)
*C07K 14/705* (2006.01)

(52) U.S. Cl.
CPC ............ *G01N 33/76* (2013.01); *C07K 14/705* (2013.01); *G01N 33/6893* (2013.01); *G01N 2333/70503* (2013.01); *G01N 2800/368* (2013.01); *G01N 2800/60* (2013.01)

(58) Field of Classification Search
None
See application file for complete search history.

(56) References Cited

U.S. PATENT DOCUMENTS

2006/0063162 A1* 3/2006 Deng .............................. 435/6
2010/0016173 A1* 1/2010 Nagalla et al. ................ 506/9

FOREIGN PATENT DOCUMENTS

EP 2107127 A1 * 10/2009

OTHER PUBLICATIONS

Beer et al. J. Proteome Res. 2011, 10, 1126-1138.*
Abbott J, Emmans, et al. Ectopic pregnancy: ten common pitfalls in diagnosis. The American Journal of Emergency Medicine. Nov. 1990;8(6):515-22.
Barnhart KT. Clinical practice. Ectopic pregnancy. New England Journal of Medicine. Jul. 2009;361(4):379-87.
Bjorhall K, et al. Comparison of different depletion strategies for improved resolution in proteomic analysis of human serum samples. Proteomics. Jan. 2005;5(1):307-17.
Boye K, et al., Novel feto-specific mRNA species suitable for identification of fetal cells from the maternal circulation. Prenatal Diagnostics, Oct. 2001;21(10):806-12.
Choolani M, et al. Proteomic technologies for prenatal diagnostics: advances and challenges ahead. Expert Review of Proteomics. Feb. 2009;6(1):87-101.
Echan LA & Speicher DW. Immunoaffinity depletion of high abundance plasma and serum proteins. The Protein Protocols Handbook, 3rd ed. Oct. 2009. pp. 139-153.
Echan LA, et al. Depletion of multiple high-abundance proteins improves protein profiling capacities of human serum and plasma. Proteomics. Aug. 2005;5(13):3292-303.
Fang Y, et al. Quantitative analysis of proteome coverage and recovery rates for upstream fractionation methods in proteomics. Journal of Proteome Research. Apr. 2010;9(4):1902-12. (e-publication Jan. 16, 2010).
Gerton GL, et al. A serum proteomics approach to the diagnosis of ectopic pregnancy. Annals of the New York Academy of Sciences. Jun. 2004;1022:306-16.
Johansen M, et al. Trophoblast deportation in human pregnancy— its relevance for pre-eclampsia. Placenta, Sep. 1999;20(7):531-9.
Larsen MB, et al. Quantification of tissue inhibitor of metalloproteinases 2 in plasma from healthy donors and cancer patients. Scandinavian Journal of Immunology. May 2005;61(5):449-60.
Lipscomb GH. Ectopic pregnancy: still cause for concern. Obstetrics & Gynecology, Mar. 2010;115(3):487-8.
Mueller MD, et al. Novel placental and nonplacental serum markers in ectopic versus normal intrauterine pregnancy. Fertility and Sterility. Apr. 2004;81(4):1106-11.
Neubert H, et al. Label-free detection of differential protein expression by LC/MALDI mass spectrometry. Journal of Proteome Research. Jun. 2008;7(6):2270-9.
Paweletz CP, et al. Application of an end-to-end biomarker discovery platform to identify target engagement markers in cerebrospinal fluid by high resolution differential mass spectrometry. Journal of Proteome Research. Mar. 2010;9(3):1392-401. (e-publication Jan. 24, 2010).
Picchiassi E, et al., Identification of universal mRNA markers for noninvasive prenatal screening of trisomies. Prenatal Diagnosis, Aug. 2010;30(8):764-70. (e-publication May 27, 2010).
Piersma SR, et al. Workflow comparison for label-free, quantitative secretome proteomics for cancer biomarker discovery: method evaluation, differential analysis, and verification in serum. Journal of Proteome Research. Apr. 2010;9(4):1913-22. (e-publication Jan. 19, 2010).

(Continued)

*Primary Examiner* — Jacob Cheu
(74) *Attorney, Agent, or Firm* — Howson & Howson LLP

(57) ABSTRACT

Methods and compositions are provided for diagnosing ectopic pregnancy in a mammalian subject by detecting changes in expression of ISM2, ADAM12, PST1, PSG7, PST11, PSG9, PSG2 and other genes identified therein, including combinations thereof. A selected gene, gene transcript or protein/peptide expression product, or profiles or signatures formed by combinations of same, detected in a biological fluid of a subject, enables comparison of the corresponding genes, proteins or profiles from that of a reference or control having a normal intrauterine pregnancy. Detection of characteristic changes in the gene profile or protein expression signature of the subject is correlated with a diagnosis of ectopic pregnancy. Various compositions for use in such diagnosis include PCR primer-probe sets or ligands, labeled or immobilized, which are capable of detecting the changes in expression or translation of these targets.

12 Claims, 30 Drawing Sheets

(56) References Cited

OTHER PUBLICATIONS

Poon LL, et al, Circulating fetal RNA in maternal plasma. Annals of the New York Academy of Sciences, Sep. 2001;945:207-10.

Randall S, et al. Placentation in the fallopian tube. International Journal of Gynecological Pathology, Jun. 1987;6(2):132-9.

Rausch ME, et al., Development of a multiple marker test for ectopic pregnancy. Obstetrics & Gynecology, Mar. 2011;117(3):573-82.

Takacs P, et al, Placental mRNA in maternal plasma as a predictor of ectopic pregnancy, International Journal of Gynecology and Obstetrics, May 2012;117(2):131-3. Epub Feb. 17, 2012.

Tong YK and Dennis Lo YM. Diagnostic developments involving cell-free (circulating) nucleic acids. Clinica Chimica Acta, Jan. 2006;363(1-2):187-96.

Tsui NB and Dennis Lo YM. Placental RNA in maternal plasma: toward noninvasive fetal gene expression profiling. Annals of the New York Academy of Sciences, Sep. 2006;1075:96-102.

Wataganara T and Bianchi DW. Fetal cell-free nucleic acids in the maternal circulation:new clinical applications. Annals of the New York Academy of Sciences, Jun. 2004;1022:90-9.

Anderson L. Candidate-based proteomics in the search for biomarkers of cardiovascular disease. Journal of Physiology, Dec. 2004;563(Pt 1):23-60.

Anderson NL and Anderson NG. The human plasma proteome: history, character, and diagnostic prospects. Molecular & Cellular Proteomics. Oct. 2002;1(11):845-67.

Anderson NL. The clinical plasma proteome: a survey of clinical assays for proteins in plasma and serum. Clinical Chemistry. Nov. 2009;56(2):177-85.

Anderson NL. The roles of multiple proteomic platforms in a pipeline for new diagnostics. Molecular & Cellular Proteomics. Jul. 2005;4(10):1441-4.

Beer, L. A. et al., Systematic Discovery of Ectopic Pregnancy Serum Biomarkers Using 3-D Protein Profiling Coupled with Label-free Quantitation. Journal of Proteome Research, Mar. 4, 2011;10(3):1126-38, published on-line Dec. 10, 2010.

Cabar FR et al. Serum markers in the diagnosis of tubal pregnancy. Clinics (Sao Paulo) Jul. 2008;63(5):701-8.

Cartwright J, et al. Serum biomarkers of tubal ectopic pregnancy: current candidates and future possibilities. Reproduction. Jul. 2009;138(1):9-22.

Chang J, et al. Pregnancy related mortality surveillance—United States, 1991-1999. Mobidity and Mortality Weekly Report Surveillance Summaries, Feb. 2003;52(2):1-8.

Daponte A, et al. The value of a single combined measurement of VEGF, glycodelin, progesterone, PAPP-A, HPL and LIF for differentiating between ectopic and abnormal intrauterine pregnancy. Human Reproduction. Jul. 2005;20(11):3163-6.

Elliott MH, et al. Current trends in quantitative proteomics. Journal of Mass Spectrometry. Dec. 2009;44(12):1637-60.

Hoover KW, et al. Trends in the diagnosis and treatment of ectopic pregnancy in the United States. Obstetrics & Gynecology. Mar. 2010;115(3):495-502.

Keller A, et al. Empirical statistical model to estimate the accuracy of peptide identifications made by MS/MS and database search. Analytical Chemistry, Oct. 2002;74(20):5383-92.

Kumpel B, et al. Phenotype and mRNA expression of syncytiotrophoblast microparticles isolated from human placenta. Annals of the New York Academy of Sciences, Aug. 2008;1137:144-7.

Masuzaki H, et al. Placental mRNA in maternal plasma and its clinical application to the evaluation of placental status in a pregnant woman with placenta previa-percreta. Clinical Chemistry, May 2005;51(5):923-5.

Mueller LN, et al. An assessment of software solutions for the analysis of mass spectrometry based quantitative proteomics data. Journal of Proteome Research. Nov. 2007;7(1):51-61.

Nesvizhskii AI, et al. A statistical model for identifying proteins by tandem mass spectrometry. Analytical Chemistry, Sep. 2003;75(17):4646-58.

Ng EK et al. mRNA of placental origin is readily detectable in maternal plasma. Proceedings of the National Academy of Sciences U S A, Apr. 2003;100(8):4748-53.

Ng EK, et al. Evaluation of human chorionic gonadotropin beta-subunit mRNA concentrations in maternal serum in aneuploid pregnancies: a feasibility study. Clinical Chemistry, Jun. 2004;50(6): 1055-7.

Okazaki S. et al, Measurement of mRNA of trophoblast-specific genes in cellular and plasma components of maternal blood. Journal of Medical Genetics, Sep. 2006;43(9):e47.

Old WM, et al. Comparison of label-free methods for quantifying human proteins by shotgun proteomics. Molecular & Cellular Proteomics. Jun. 2005;4(10):1487-502.

Omenn GS, et al. Overview of the HUPO Plasma Proteome Project: results from the pilot phase with 35 collaborating laboratories and multiple analytical groups, generating a core dataset of 3020 proteins and a publicly-available database. Proteomics. May 2005;5(13):3226-45.

Poon LL, et al., Presence of fetal RNA in maternal plasma. Clinical Chemistry, Nov. 2000;46(11):1832-4.

Rifai N and Gillette MA. Protein biomarker discovery and validation: the long and uncertain path to clinical utility. Nature Biotechnology. Aug. 2006; 24(8):971-83.

Seeber BE, et al. Suspected ectopic pregnancy. Obstetrics & Gynecology. Feb. 2006;107(2 Pt 1):399-413.

States DJ, et al. Challenges in deriving high-confidence protein identifications from data gathered by a HUPO plasma proteome collaborative study. Nature Biotechnology. Mar. 2006;24(3):333-8.

Steen H, et al. The ABC's (and XYZ's) of peptide sequencing. Nature Reviews Molecular Cell Biology.Sep. 2004;5(9):699-711.

Tang HY, et al. A novel four-dimensional strategy combining protein and peptide separation methods enables detection of low-abundance proteins in human plasma and serum proteomes. Proteomics. Feb. 2005;5(13):3329-42.

Tay JI, et al. Ectopic pregnancy. BMJ. Apr. 2000;320(7239):916-9.

Wang H, et al. Comparison of extensive protein fractionation and repetitive LC-MS/MS analyses on depth of analysis for complex proteomes. Journal of Proteome Research. Dec. 2009;9(2):1032-40.

Wewer UM, et al. ADAM12 is a four-leafed clover: the excised prodomain remains bound to the mature enzyme. Journal of Biological Chemistry. Apr. 2006;281(14):9418-22.

Zhu W, et al. Mass spectrometry-based label-free quantitative proteomics. Journal of Biomedicine & Biotechnology. Nov. 2009;2010:840518.

\* cited by examiner

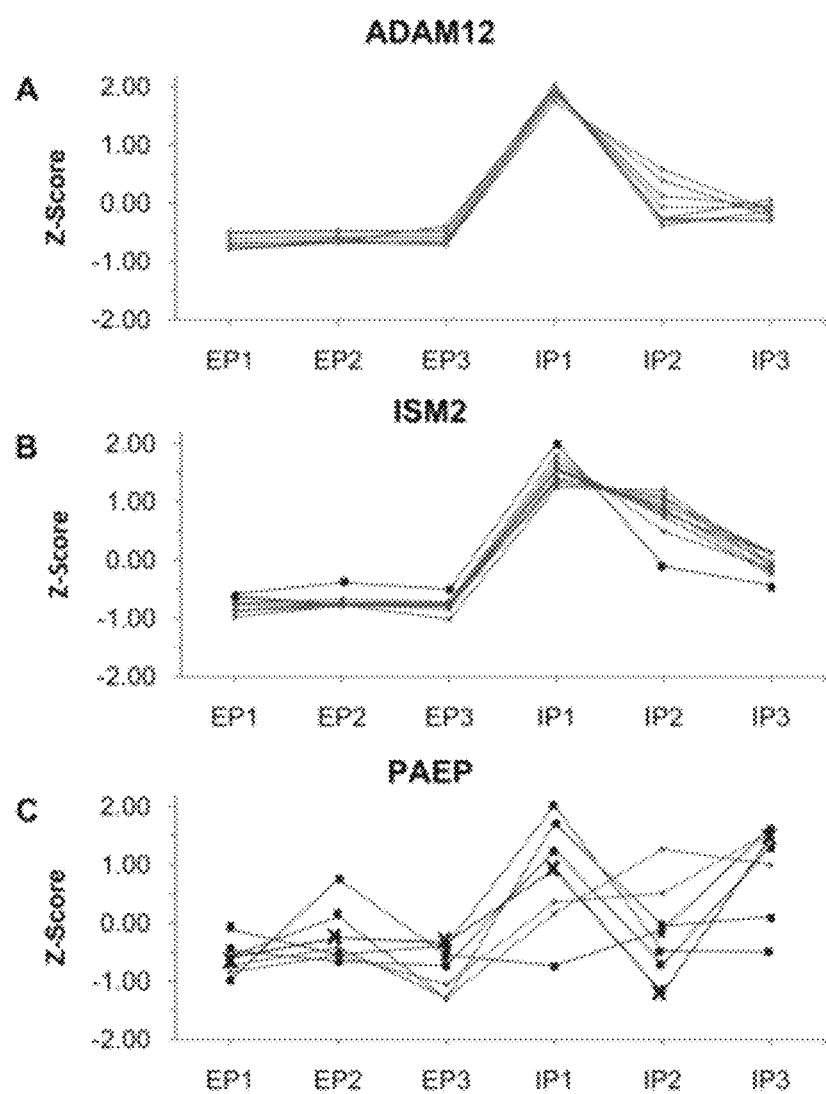

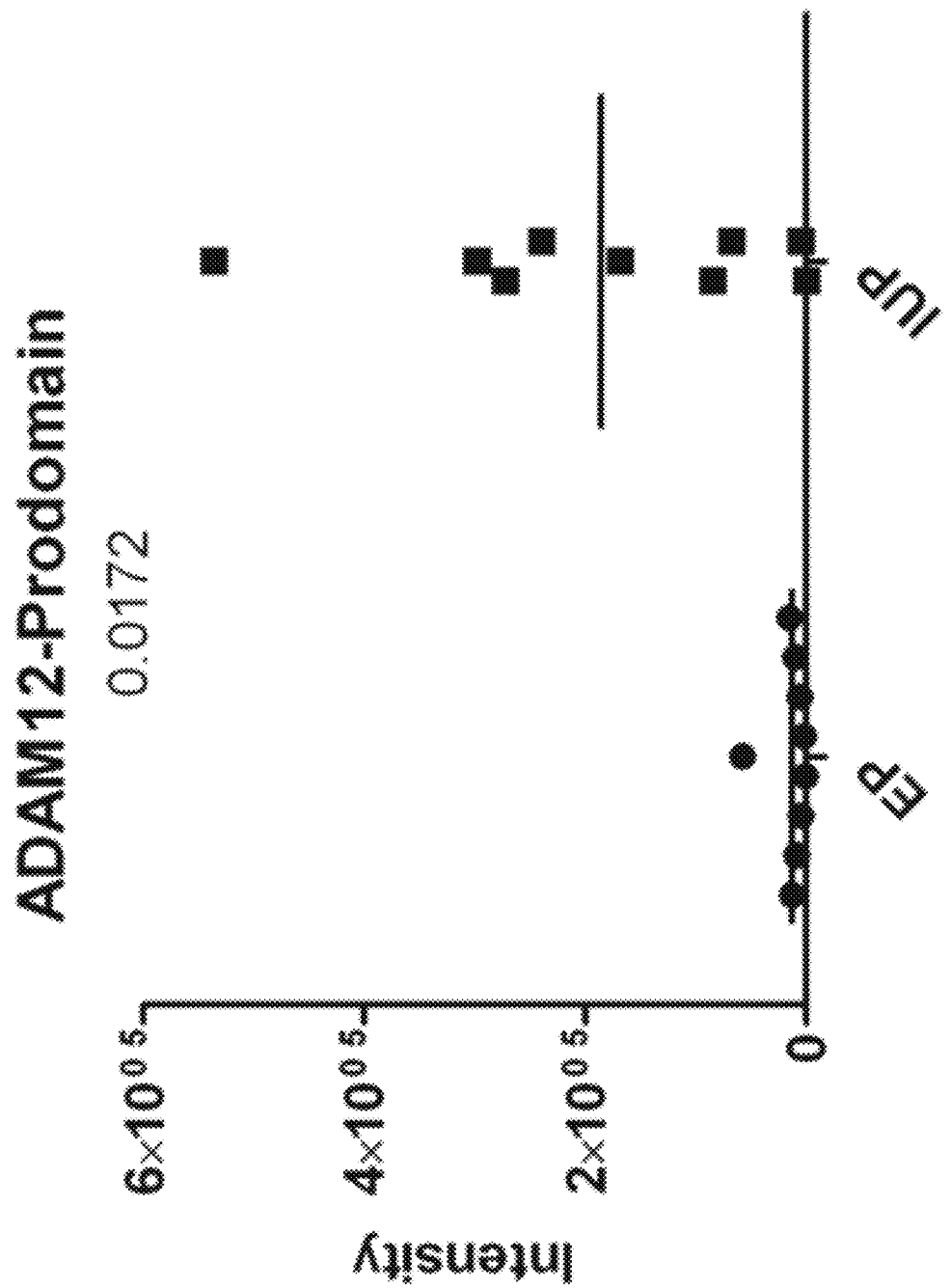

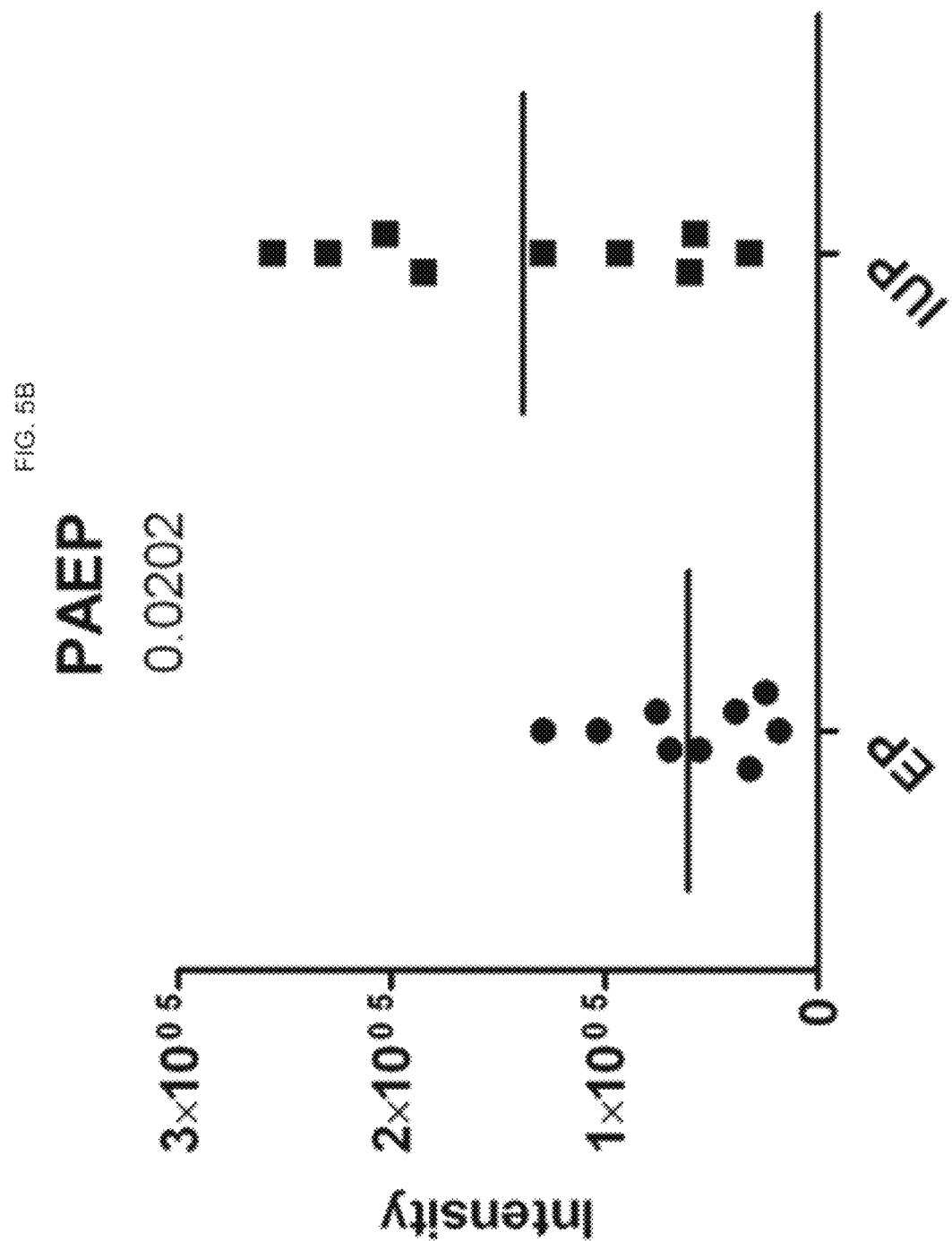

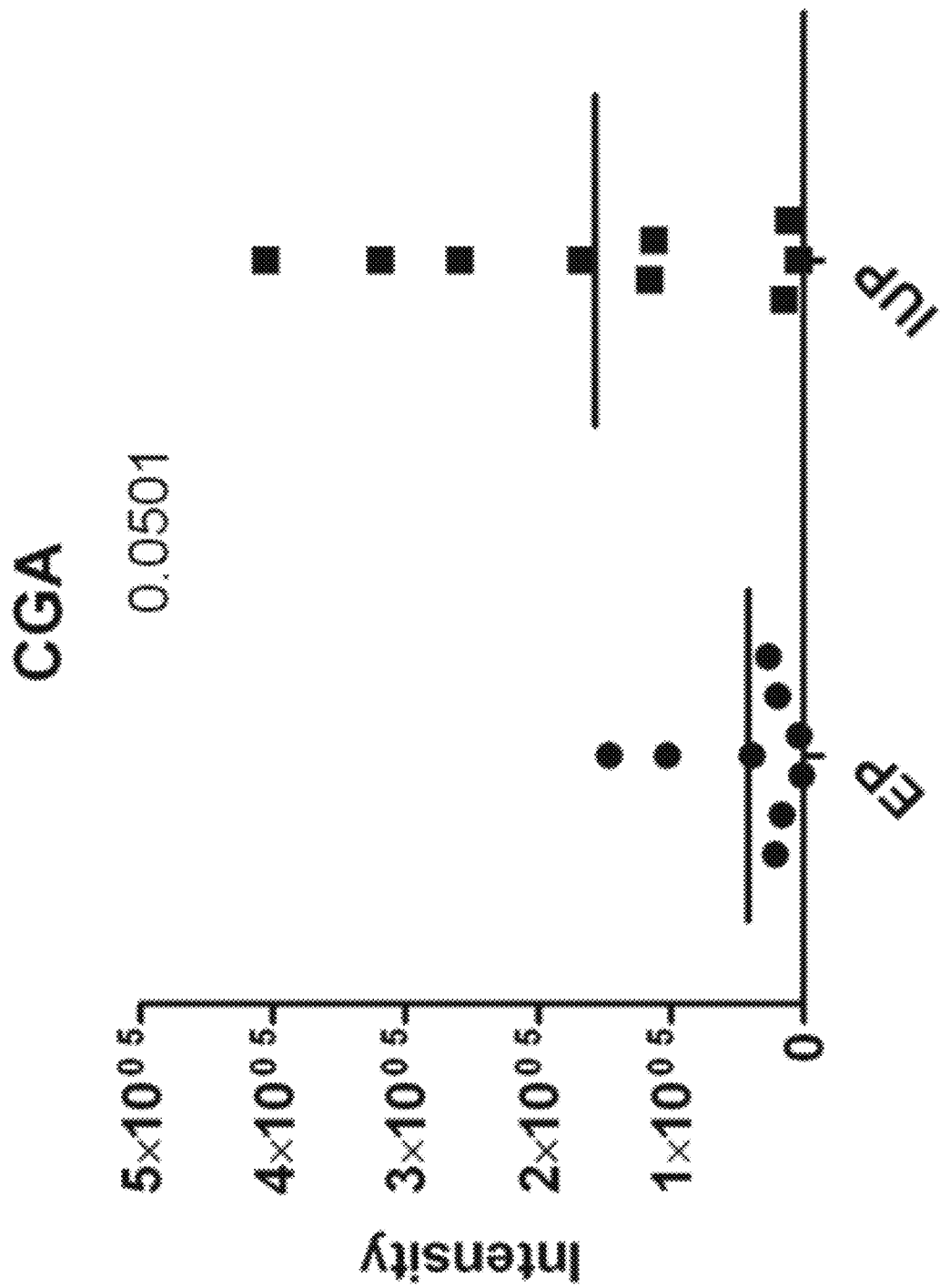

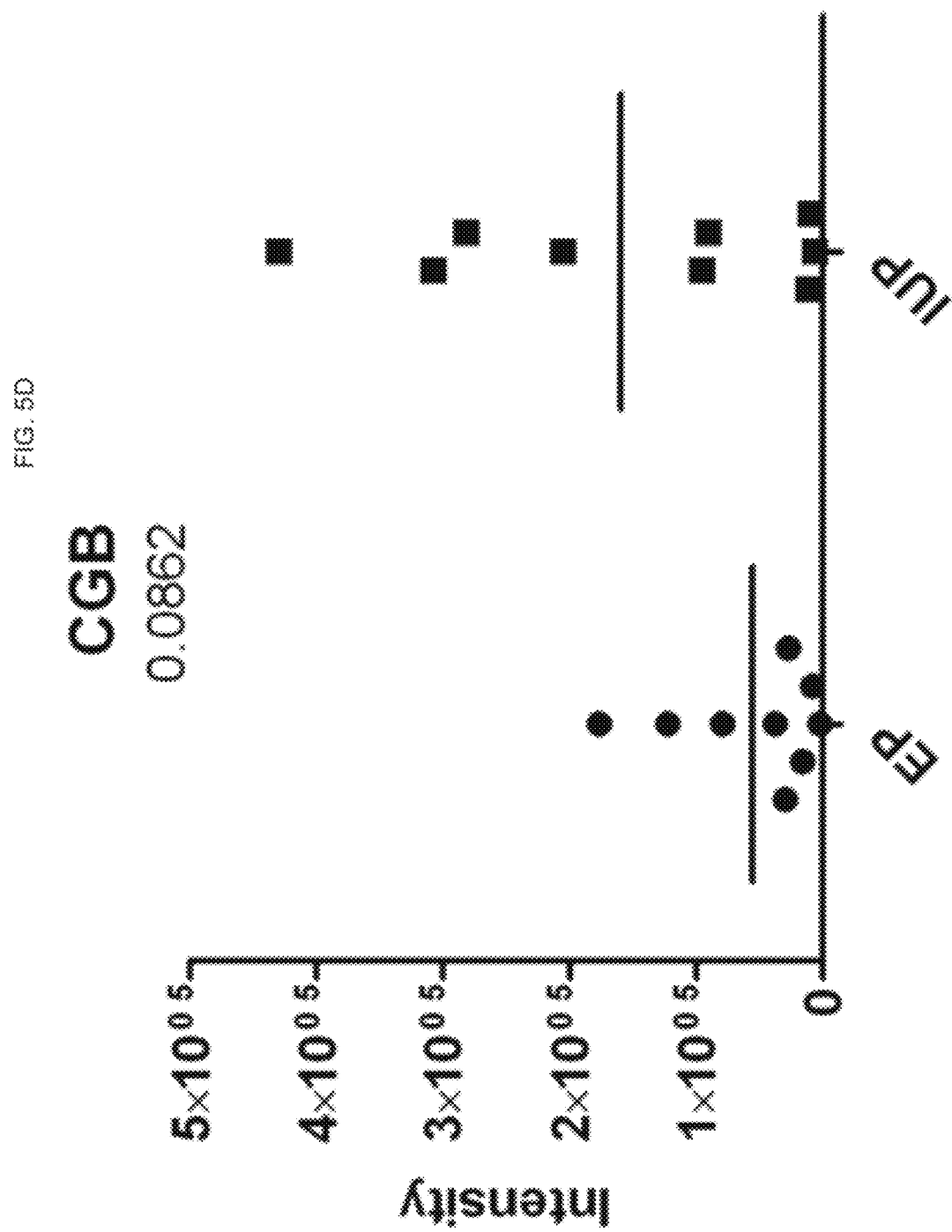

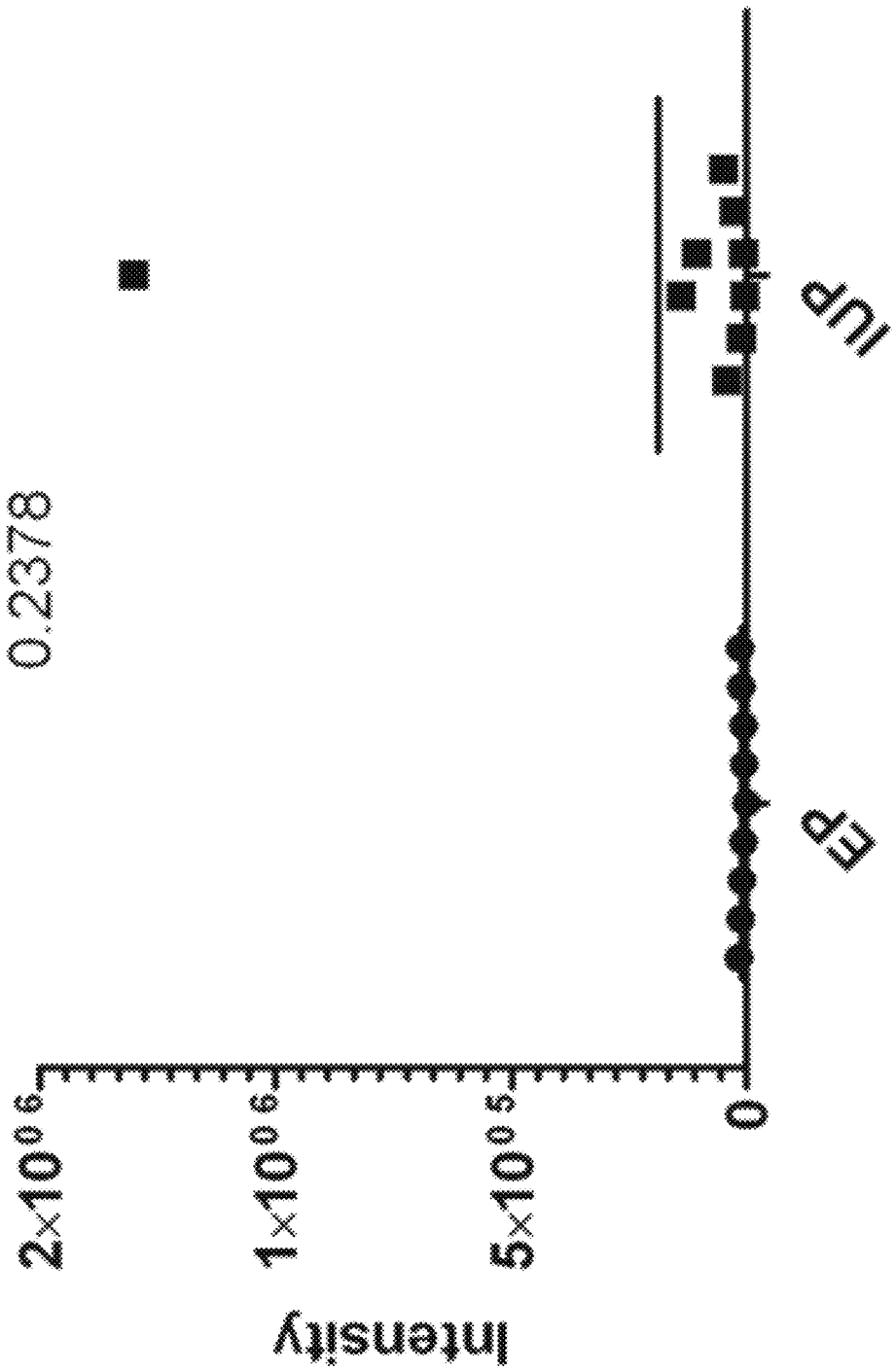

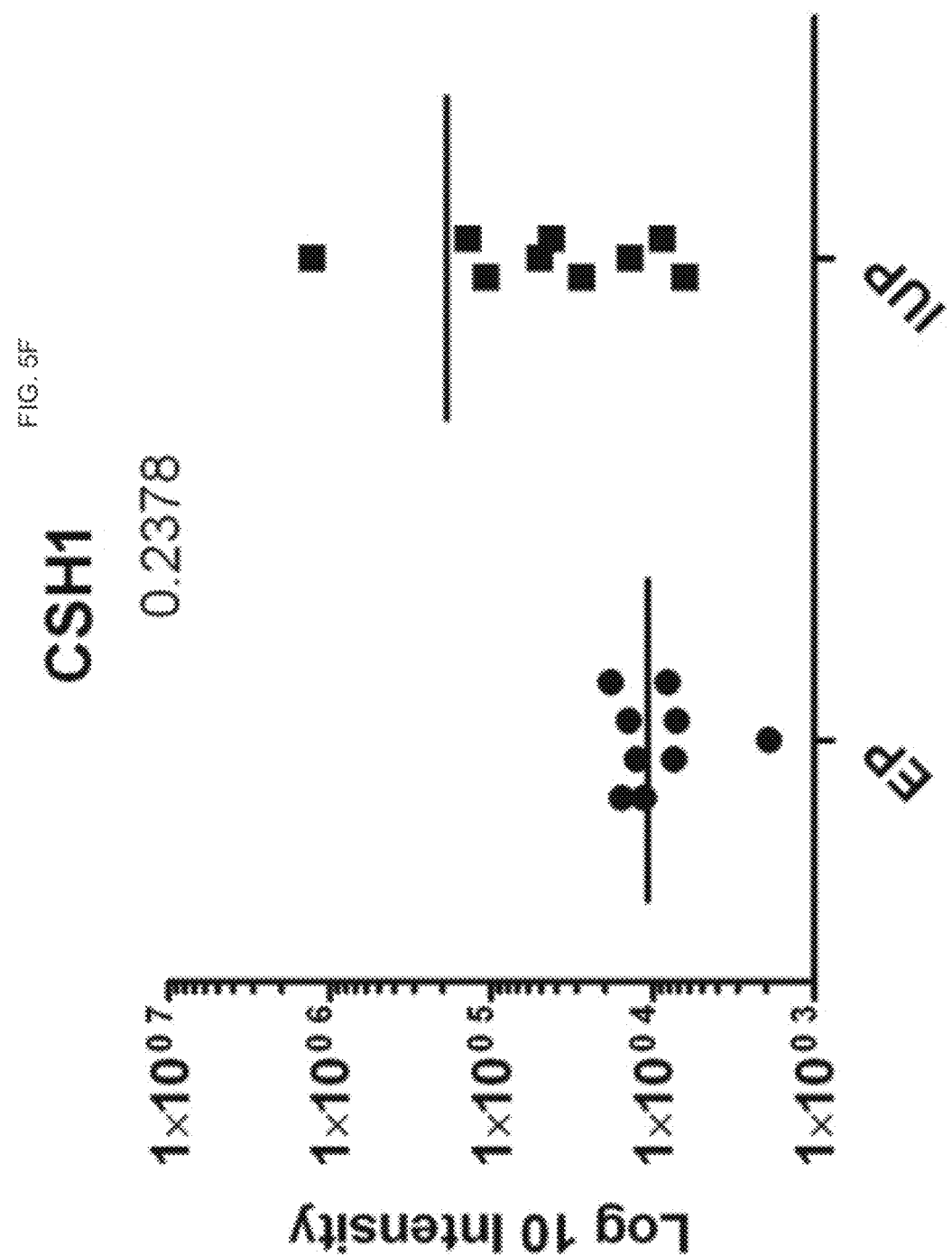

FIG. 6A

| Protein Accession | Protein Description | Modified Peptide Sequence | SEQ ID NO |
|---|---|---|---|
| O43184 | ADAM 12 precursor | EHNLER | 2 |
| O43184 | ADAM 12 precursor | GC[160.030]SC[160.030]SC[160.030]SC[160.030]Z[0]MAVEK | 3 |
| O43184 | ADAM 12 precursor | GSC[160.030]SZ[0]SHHNTPNLAAK | 4 |
| O43184 | ADAM 12 precursor | GYSDAVVLSTC[160.030]Z[0]SGLR | 5 |
| O43184 | ADAM 12 precursor | KDLETSLEK | 6 |
| O43184 | ADAM 12 precursor | MHPEVLNIR | 7 |
| O43184 | ADAM 12 precursor | SGDLWPVK | 8 |
| O43184 | ADAM 12 precursor | VNSAGDPVGNC[160.030]Z[0]IGK | 9 |

Sum of Peptide Intensities:

Sum of Significant Peptide Intensities:

Sum of Unique, Significant Peptide Intensities:

| UPI0001507638 | Pregnancy specific beta-1-glycoprotein 7 precursor | FQLSGQK | 10 |
| UPI0001507638 | Pregnancy specific beta-1-glycoprotein 7 precursor | HSQLVIC[160.030]Z[0]SVK | 11 |
| UPI0001507638 | Pregnancy specific beta-1-glycoprotein 7 precursor | LPKPYITINNLNPR | 12 |
| UPI0001507638 | Pregnancy specific beta-1-glycoprotein 7 precursor | SDPVTLNVLYGPDLPR | 13 |
| UPI0001507638 | Pregnancy specific beta-1-glycoprotein 7 precursor | YIGPAYSGR | 14 |

Sum of Peptide Intensities:

FIG. 6D

| | | | |
|---|---|---|---|
| | | Sum of Peptide Intensities: | |
| | | Sum of Significant Peptide Intensities: | |
| | | Sum of Unique, Significant Peptide Intensities: | |
| P11464-2 | Isoform 2 of Pregnancy-specific beta-1-glycoprotein 1 | TFTLHLETKPSSSSNLNPR | 45 |
| P11464-2 | Isoform 2 of Pregnancy-specific beta-1-glycoprotein 1 | HSGLYVC[160.0302]SVR | 46 |
| P11464-2 | Isoform 2 of Pregnancy-specific beta-1-glycoprotein 1 | TFLLGVTK | 47 |
| P11464-2 | Isoform 2 of Pregnancy-specific beta-1-glycoprotein 1 | YTAGPYEC[160.0302]EIR | 48 |
| | | Sum of Peptide Intensities: | |
| | | Sum of Significant Peptide Intensities: | |
| | | Sum of Unique, Significant Peptide Intensities: | |
| P11465 | Pregnancy-specific beta-1-glycoprotein 2 precursor | FQQSGSNHFPQTTK | 49 |
| P11465 | Pregnancy-specific beta-1-glycoprotein 2 precursor | IGLPLLNPT | 50 |
| | | Sum of Peptide Intensities: | |
| | | Sum of Significant Peptide Intensities: | |
| | | Sum of Unique, Significant Peptide Intensities: | |

FIG. 6F

| | | | |
|---|---|---|---|
| Q13219 | Pappalysin-1 precursor | AYSGQR...VTNCTYSGDCK | 62 |
| Q13219 | Pappalysin-1 precursor | AFLDWELK | 63 |
| Q13219 | Pappalysin-1 precursor | C[160.0302]ESDASQGLQSNVHC[160.030 2]R | 64 |
| Q13219 | Pappalysin-1 precursor | C[160.0302]YFHGEC[160.0302]EEEG... C | 65 |
| Q13219 | Pappalysin-1 precursor | ...K | 66 |
| Q13219 | Pappalysin-1 precursor | DIPHVLSVPTR | 67 |
| Q13219 | Pappalysin-1 precursor | ...C...HR | 68 |
| Q13219 | Pappalysin-1 precursor | ...C[160.0302]...R | 69 |
| Q13219 | Pappalysin-1 precursor | ...C[160.0302]...K | 70 |
| Q13219 | Pappalysin-1 precursor | EAEGHPDNEQP[160.0302]K | 71 |
| Q13219 | Pappalysin-1 precursor | EELSDMFTHGNTALPQLLQENWQNVK | 72 |
| Q13219 | Pappalysin-1 precursor | ...C[160.0302]...R | 73 |
| Q13219 | Pappalysin-1 precursor | EQVDFQIHQLAEAPK | 74 |
| Q13219 | Pappalysin-1 precursor | FHGLVCC[160.0302]TNGFDFNSEC[160.030 2]R | 75 |
| Q13219 | Pappalysin-1 precursor | G...YYPSK | 76 |
| Q13219 | Pappalysin-1 precursor | ...C[160.0302]...R | 77 |
| Q13219 | Pappalysin-1 precursor | ...K | 78 |
| Q13219 | Pappalysin-1 precursor | GFTTSPAEDSC[160.0302]VHFAC[160.0302] R | 79 |
| Q13219 | Pappalysin-1 precursor | EK | 80 |
| Q13219 | Pappalysin-1 precursor | GYGFSLK | 81 |
| Q13219 | Pappalysin-1 precursor | KC[160.0302]ESDASQGLQSNVHC[160.0 302]R | 82 |
| Q13219 | Pappalysin-1 precursor | ...R | 83 |
| Q13219 | Pappalysin-1 precursor | LSSTHLNFK | 84 |
| Q13219 | Pappalysin-1 precursor | LLANC[160.0302]DSK | |
| Q13219 | Pappalysin-1 precursor | MNPLIPVYHDLCQPYYSQAVR | |
| Q13219 | Pappalysin-1 precursor | QEVSFNC[160.0302]EQC[160.0302]PSR | |

FIG. 7A

| Protein Accession # | Gene Name | Protein Description | IUP Intensity | EP Intensity | # Peptides Pass ANOVA/Total # Peptides | Fold Change |
|---|---|---|---|---|---|---|
| Q9UKU6 | LNPEP | Leucyl-cystinyl aminopeptidase | 2.77E+06 | 6.26E+04 | 4/4 | -44.26 |
| O43184 | ADAM12 | ADAM 12 precursor | 2.35E+07 | 1.07E+06 | 8/8 | -21.93 |
| Q13219 | PAPPA | Pappalysin-1 precursor | 1.84E+08 | 1.11E+07 | 40/40 | -16.67 |
| UPI0001807638 | PSG7 | Pregnancy specific beta-1-glycoprotein 7 precursor | 6.35E+07 | 5.06E+06 | 5/5 | -12.53 |
| UPI00004B4B14C | BM2 | bisturin 2 (thrombospondin, type 1 domain containing 3 isoform 1) | 2.85E+07 | 2.34E+06 | 10/10 | -12.19 |
| UPI000251E28 | PSG11 | Pregnancy specific beta-1-glycoprotein 11 isoform | 5.47E+07 | 4.64E+06 | 5/5 | -11.78 |
| P01241 | CSH1 | Chorionic somatomammotropin hormone | 9.31E+07 | 8.56E+06 | 14/14 | -10.89 |
| Q6EU7 | PSG9 | Pregnancy specific beta-1-glycoprotein 9 (PSG9) | 2.61E+08 | 2.51E+07 | 15/15 | -10.40 |
| P13464-2 | PSG1 | Isoform 2 of Pregnancy-specific beta-1- | 6.97E+07 | 7.07E+06 | 4/4 | -9.86 |
| P11465 | PSG2 | Pregnancy-specific beta-1-glycoprotein 2 precursor | 5.97E+06 | 6.14E+05 | 2/2 | -9.73 |
| P13727 | PRG2 | Bone marrow proteoglycan precursor | 4.06E+08 | 5.45E+07 | 9/9 | -7.45 |
| Q28KL2 | PZP | PZP protein | 1.00E+09 | 1.47E+08 | 12/12 | -6.81 |
| Q07654 | TFF3 | Trefoil factor 3 precursor | 2.83E+05 | 4.43E+04 | 2/2 | -6.38 |
| P20742 | PZP | Pregnancy zone protein precursor | 1.89E+10 | 3.54E+09 | 73/73 | -5.35 |
| P00799 | LALBA | Alpha-lactalbumin precursor | 8.63E+05 | 1.63E+05 | 3/3 | -5.30 |
| P01215 | CGA | Glycoprotein hormones alpha chain precursor | 7.22E+07 | 1.47E+07 | 3/3 | -4.91 |
| P01233 | CGB | Choriogonadotropin subunit beta precursor | 2.67E+08 | 5.44E+07 | 4/4 | -4.90 |
| UPI000013D168 | PZP | Pregnancy zone protein precursor | 1.11E+08 | 2.33E+07 | 4/4 | -4.84 |
| UPI00008D61B9 | SVEP1 | Polydom | 4.14E+05 | 1.23E+05 | 2/2 | -3.37 |
| P31151 | S100A7 | Protein S100-A7 | 1.22E+06 | 3.79E+05 | 2/2 | -3.23 |
| P06732 | CKM | Creatine kinase M-type | 4.53E+06 | 1.44E+06 | 2/6 | -3.16 |
| Q8WUA8 | TSKU | Tsukushi precursor | 2.42E+07 | 8.56E+06 | 9/9 | -2.83 |
| P08833 | IGFBP1 | Insulin-like growth factor-binding protein 1 | 1.72E+06 | 6.19E+05 | 3/3 | -2.77 |
| P03951 | F11 | Coagulation factor XI precursor | 7.98E+06 | 2.97E+06 | 4/4 | -2.69 |
| Q15166 | PON3 | Serum paraoxonase/lactonase 3 | 3.76E+06 | 1.44E+06 | 2/10 | -2.62 |
| Q5T6T0 | PAEP | Progestagen-associated endometrial protein | 3.39E+07 | 1.30E+07 | 6/7 | -2.60 |
| UPI0000233611 | UBE2V1 | ubiquitin-conjugating enzyme E2 K(us-UEV) isoform | 1.14E+06 | 2.84E+06 | 2/4 | 2.50 |
| Q9UL83 | N/A | Myosin-reactive immunoglobulin light chain | 9.92E+06 | 2.49E+07 | 4/4 | 2.51 |

FIG. 7B

| ID | Gene | Description | | | |
|---|---|---|---|---|---|
| UPI0002239910 | N/A | Fab 47e light chain | 1.56E+06 | 4.00E+06 | 2/2 | 2.56 |
| Q5NV65 | IGLV2-18 | V2-5 protein | 1.25E+06 | 3.21E+06 | 2/2 | 2.58 |
| P30040 | CAT | Catalase | 3.48E+07 | 9.04E+07 | 16/16 | 2.60 |
| P21291 | CSRP1 | Cysteine and glycine-rich protein 1 | 4.45E+05 | 1.17E+06 | 2/3 | 2.62 |
| A6NH80 | SOD1 | Superoxide dismutase [Cu-Zn] | 4.65E+06 | 1.24E+07 | 4/4 | 2.66 |
| Q99497 | PARK7 | Protein DJ-1 | 3.50E+08 | 1.01E+07 | 9/10 | 2.81 |
| Q15185 | PTGES3 | Prostaglandin E synthase 3 | 1.56E+05 | 4.43E+05 | 2/3 | 2.84 |
| A5YM50 | RAB31B | RAB31B protein | 2.22E+08 | 6.38E+08 | 7/7 | 2.88 |
| P00738 | HP | Haptoglobin precursor | 1.90E+07 | 5.55E+07 | 9/9 | 2.92 |
| P30041 | PRDX6 | Peroxiredoxin-6 | 2.21E+07 | 6.51E+07 | 14/15 | 2.94 |
| P67936 | TPM4 | Tropomyosin alpha-4 chain | 1.96E+08 | 5.90E+08 | 7/7 | 3.01 |
| Q4KMW9 | SLC4A1 | Solute carrier family 4, anion exchanger, member 1 (Band 3 anion transport protein) | 1.08E+05 | 3.29E+05 | 2/3 | 3.04 |
| Q15404 | RSU1 | Ras suppressor protein 1 | 1.88E+05 | 5.70E+05 | 2/3 | 3.04 |
| Q96IU4 | ABHD14B | Abhydrolase domain-containing protein 14B | 4.06E+05 | 1.25E+06 | 3/3 | 3.08 |
| PGS241-2 | EIF5A | Isoform 2 of eukaryotic translation initiation factor | 1.10E+06 | 3.55E+06 | 5/5 | 3.23 |
| Q68R81 | PGLYRP2 | Peptidoglycan recognition protein L (N-acetylmuramoyl-L-alanine amidase) | 1.24E+08 | 4.14E+08 | 4/4 | 3.33 |
| Q15257 | PPP2R4 | Serine/threonine-protein phosphatase 2A regulatory subunit B' | 5.86E+05 | 2.04E+06 | 3/4 | 3.48 |
| A6NMY0 | TLN2 | Uncharacterized protein TLN1 | 2.12E+07 | 7.47E+07 | 72/77 | 3.53 |
| O75347 | TBCA | Tubulin-specific chaperone A | 1.84E+05 | 6.55E+05 | 2/5 | 3.56 |
| A6NRJ9 | SELENBP1 | Uncharacterized protein SELENBP1 | 2.84E+06 | 1.04E+07 | 5/6 | 3.66 |
| P62208 | SKP1 | S-phase kinase-associated protein 1A | 1.45E+05 | 5.46E+05 | 3/4 | 3.75 |
| UP1000133C00F | CAP1 | Adenylyl cyclase-associated protein 1 (CAP 1) | 1.09E+06 | 4.13E+06 | 5/5 | 3.79 |
| A6NN74 | N/A | Uncharacterized protein ENSP00000374604 | 7.96E+06 | 3.06E+07 | 2/2 | 3.85 |
| O00299 | CLIC3 | Chloride intracellular channel protein 1 | 3.51E+06 | 1.40E+07 | 5/6 | 4.00 |
| P51452 | DUSP3 | Dual specificity protein phosphatase 3 | 2.10E+05 | 8.52E+05 | 3/3 | 4.06 |
| UP100028083 | ALAD | Delta-aminolevulinic acid dehydratase isoform a | 1.60E+08 | 6.78E+08 | 6/9 | 4.23 |
| UP1000041AD6 | PARVB | Parvin, beta isoform a | 3.17E+05 | 1.52E+06 | 3/3 | 4.79 |
| Q12YL5 | TPM1 | Tropomyosin 1 alpha variant 6 | 1.35E+05 | 6.52E+05 | 2/3 | 4.83 |
| Q59EH3 | N/A | Acid phosphatase 1 isoform c variant | 3.92E+05 | 1.94E+06 | 4/4 | 4.97 |
| UP1000230CC3 | GPX1 | Glutathione peroxidase 1 isoform 1 | 1.14E+05 | 6.20E+05 | 3/4 | 5.42 |

FIG. 7C

| | Gene Name[a] | Description | | | Fold change[b] |
|---|---|---|---|---|---|
| UPI0000208SC1 | PLEK | Pleckstrin | 1.50E+06 | 8.30E+06 | 3/3 | 5.55 |
| Q13642 | FHL1 | Four and a half LIM domains protein 1 | 2.21E+05 | 1.24E+06 | 2/2 | 5.62 |
| A6NEJ8 | LIMS3 | Uncharacterized protein LIMS3 | 3.46E+05 | 1.98E+06 | 2/2 | 5.74 |
| Q9UBW5 | BIN2 | Bridging integrator 2 | 1.15E+05 | 7.10E+05 | 2/2 | 6.19 |
| Q549N7 | HBB | Mutant beta-globin | 2.56E+07 | 2.63E+08 | 3/3 | 10.26 |
| P02042 | HBD | Hemoglobin subunit delta | 3.72E+07 | 4.78E+08 | 2/2 | 12.85 |
| Q1HDT5 | HBA1 | Hemoglobin alpha 1-2 hybrid | 1.95E+07 | 2.95E+08 | 5/5 | 15.10 |
| Q9UK54 | HBB | Hemoglobin beta subunit variant | 5.76E+07 | 1.12E+09 | 10/10 | 19.50 |
| Q96T46 | HBA2 | Hemoglobin alpha 2 | 3.06E+07 | 6.07E+08 | 6/6 | 19.82 |
| P69891 | HBG1 | Hemoglobin subunit gamma-1 | 4.79E+05 | 1.07E+07 | 9/9 | 22.39 |
| P18989 | HBB | Hemoglobin subunit beta | 4.59E+05 | 1.50E+07 | 4/4 | 32.66 |
| P02042 | HBD | Hemoglobin subunit delta | 1.30E+06 | 6.34E+07 | 7/7 | 48.75 |

[a] Gene Name extracted from UniRef100 protein database using the indicated protein accession #; N/A indicates Gene Name not available.
[b] Fold change values are for peptides which passed ANOVA filter of p > 0.001 and are expressed using IUP as the reference.

Fig. 8
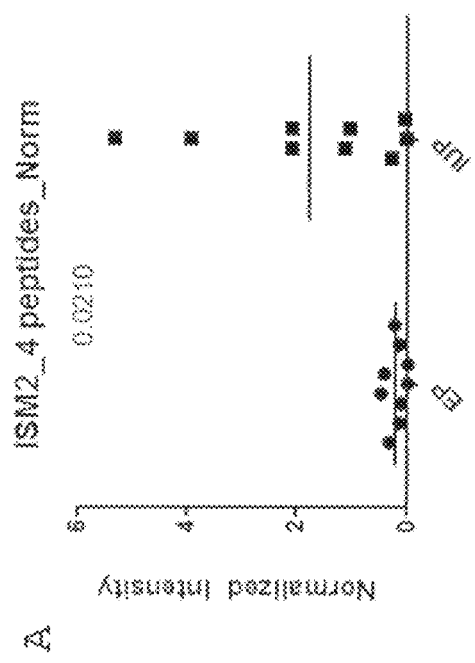
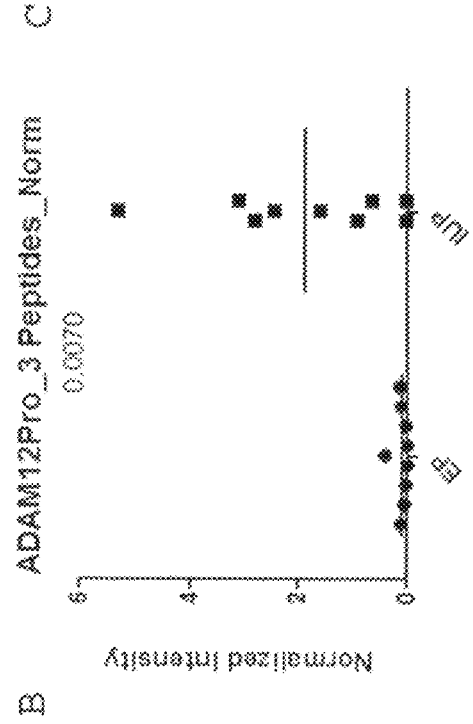
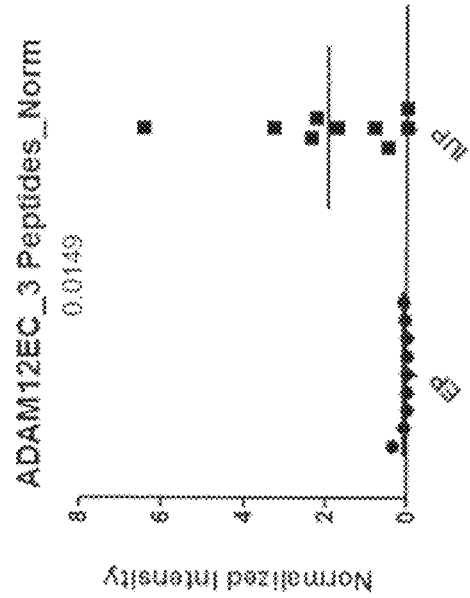

SEQUENCE LISTING

<160> NUMBER OF SEQ ID NOS: 118

<210> SEQ ID NO 1
<211> LENGTH: 909
<212> TYPE: PRT
<213> ORGANISM: Homo sapiens

<400> SEQUENCE: 1

Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

Leu Trp Asn Gln Gly Arg Ala Asp Glu Val Val Ser Ala Ser Val Arg
        35                  40                  45

Ser Gly Asp Leu Trp Ile Pro Val Lys Ser Phe Asp Ser Lys Asn His
    50                  55                  60

Pro Glu Val Leu Asn Ile Arg Leu Gln Arg Glu Ser Lys Glu Leu Ile
65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Val Ile Leu Gly His Cys Tyr Tyr His Gly His Val Arg Gly Tyr
        115                 120                 125

Ser Asp Ser Ala Val Ser Leu Ser Thr Cys Ser Gly Leu Arg Gly Leu
    130                 135                 140

Ile Val Phe Glu Asn Glu Ser Tyr Val Leu Glu Pro Met Ser Lys Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg Arg His Lys Arg Glu
        195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255

Ile Arg Ile Val Leu Val Gly Val Glu Val Trp Asn Asp Met Asp Lys
            260                 265                 270

Cys Ser Val Ser Gln Asp Pro Phe Thr Ser Leu His Glu Phe Leu Asp
        275                 280                 285

Trp Arg Lys Met Lys Leu Leu Pro Arg Lys Ser His Asp Asn Ala Gln
    290                 295                 300

Leu Val Ser Gly Val Tyr Phe Gln Gly Thr Thr Ile Gly Met Ala Pro
305                 310                 315                 320

Ile Met Ser Met Cys Thr Ala Asp Gln Ser Gly Gly Ile Val Met Asp
                325                 330                 335

His Ser Asp Asn Pro Leu Gly Ala Ala Val Thr Leu Ala His Glu Leu
            340                 345                 350

Gly His Asn Phe Gly Met Asn His Asp Thr Leu Asp Arg Gly Cys Ser
        355                 360                 365

```
Cys Gln Met Ala Val Glu Lys Gly Gly Cys Ile Met Asn Ala Ser Thr
    370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
            420                 425                 430

Glu Glu Gly Glu Glu Cys Asp Cys Gly Glu Pro Glu Glu Cys Met Asn
        435                 440                 445

Arg Cys Cys Asn Ala Thr Thr Cys Thr Leu Lys Pro Asp Ala Val Cys
450                 455                 460

Ala His Gly Leu Cys Cys Glu Asp Cys Gln Leu Lys Pro Ala Gly Thr
465                 470                 475                 480

Ala Cys Arg Asp Ser Ser Asn Ser Cys Asp Leu Pro Glu Phe Cys Thr
                485                 490                 495

Gly Ala Ser Pro His Cys Pro Ala Asn Val Tyr Leu His Asp Gly His
            500                 505                 510

Ser Cys Gln Asp Val Asp Gly Tyr Cys Tyr Asn Gly Ile Cys Gln Thr
        515                 520                 525

His Glu Gln Gln Cys Val Thr Leu Trp Gly Pro Gly Ala Lys Pro Ala
    530                 535                 540

Pro Gly Ile Cys Phe Glu Arg Val Asn Ser Ala Gly Asp Pro Tyr Gly
545                 550                 555                 560

Asn Cys Gly Lys Val Ser Lys Ser Ser Phe Ala Lys Cys Glu Met Arg
                565                 570                 575

Asp Ala Lys Cys Gly Lys Ile Gln Cys Gln Gly Gly Ala Ser Arg Pro
            580                 585                 590

Val Ile Gly Thr Asn Ala Val Ser Ile Glu Thr Asn Ile Pro Leu Gln
        595                 600                 605

Gln Gly Gly Arg Ile Leu Cys Arg Gly Thr His Val Tyr Leu Gly Asp
    610                 615                 620

Asp Met Pro Asp Pro Gly Leu Val Leu Ala Gly Thr Lys Cys Ala Asp
625                 630                 635                 640

Gly Lys Ile Cys Leu Asn Arg Gln Cys Gln Asn Ile Ser Val Phe Gly
                645                 650                 655

Val His Glu Cys Ala Met Gln Cys His Gly Arg Gly Val Cys Asn Asn
            660                 665                 670

Arg Lys Asn Cys His Cys Glu Ala His Trp Ala Pro Pro Phe Cys Asp
        675                 680                 685

Lys Phe Gly Phe Gly Gly Ser Thr Asp Ser Gly Pro Ile Arg Gln Ala
    690                 695                 700

Asp Asn Gln Gly Leu Thr Ile Gly Ile Leu Val Thr Ile Leu Cys Leu
705                 710                 715                 720

Leu Ala Ala Gly Phe Val Val Tyr Leu Lys Arg Lys Thr Leu Ile Arg
                725                 730                 735

Leu Leu Phe Thr Asn Lys Lys Thr Thr Ile Glu Lys Leu Arg Cys Val
            740                 745                 750

Arg Pro Ser Arg Pro Pro Arg Gly Phe Gln Pro Cys Gln Ala His Leu
        755                 760                 765

Gly His Leu Gly Lys Gly Leu Met Arg Lys Pro Pro Asp Ser Tyr Pro
    770                 775                 780
```

```
Pro Lys Asp Asn Pro Arg Arg Leu Leu Gln Cys Gln Asn Val Asp Ile
785                 790                 795                 800

Ser Arg Pro Leu Asn Gly Leu Asn Val Pro Gln Pro Gln Ser Thr Gln
            805                 810                 815

Arg Val Leu Pro Pro Leu His Arg Ala Pro Arg Ala Pro Ser Val Pro
            820                 825                 830

Ala Arg Pro Leu Pro Ala Lys Pro Ala Leu Arg Gln Ala Gln Gly Thr
            835                 840                 845

Cys Lys Pro Asn Pro Pro Gln Lys Pro Leu Pro Ala Asp Pro Leu Ala
            850                 855                 860

Arg Thr Thr Arg Leu Thr His Ala Leu Ala Arg Thr Pro Gly Gln Trp
865                 870                 875                 880

Glu Thr Gly Leu Arg Leu Ala Pro Leu Arg Pro Ala Pro Gln Tyr Pro
            885                 890                 895

His Gln Val Pro Arg Ser Thr His Thr Ala Tyr Ile Lys
            900                 905

<210> SEQ ID NO 2
<211> LENGTH: 8
<212> TYPE: PRT
<213> ORGANISM: Homo sapiens

<400> SEQUENCE: 2

Glu Leu Ile Ile Asn Leu Glu Arg
1               5

<210> SEQ ID NO 3
<211> LENGTH: 10
<212> TYPE: PRT
<213> ORGANISM: Homo sapiens

<400> SEQUENCE: 3

Gly Cys Ser Cys Gln Met Ala Val Glu Lys
1               5                   10

<210> SEQ ID NO 4
<211> LENGTH: 15
<212> TYPE: PRT
<213> ORGANISM: Homo sapiens

<400> SEQUENCE: 4

Gly Ser Cys Gly Ser His His Asn Thr Pro Asn Leu Ala Ala Lys
1               5                   10                  15

<210> SEQ ID NO 5
<211> LENGTH: 16
<212> TYPE: PRT
<213> ORGANISM: Homo sapiens

<400> SEQUENCE: 5

Gly Tyr Ser Asp Ser Ala Val Ser Leu Ser Thr Cys Ser Gly Leu Arg
1               5                   10                  15

<210> SEQ ID NO 6
<211> LENGTH: 9
<212> TYPE: PRT
<213> ORGANISM: Homo sapiens

<400> SEQUENCE: 6

Lys Asp Leu Glu Thr Ser Leu Glu Lys
1               5
```

-continued

<210> SEQ ID NO 7
<211> LENGTH: 9
<212> TYPE: PRT
<213> ORGANISM: Homo sapiens

<400> SEQUENCE: 7

Asn His Pro Glu Val Leu Asn Ile Arg
1               5

<210> SEQ ID NO 8
<211> LENGTH: 9
<212> TYPE: PRT
<213> ORGANISM: Homo sapiens

<400> SEQUENCE: 8

Ser Gly Asp Leu Trp Ile Pro Val Lys
1               5

<210> SEQ ID NO 9
<211> LENGTH: 13
<212> TYPE: PRT
<213> ORGANISM: Homo sapiens

<400> SEQUENCE: 9

Val Asn Ser Ala Gly Asp Pro Tyr Gly Asn Cys Gly Lys
1               5                   10

<210> SEQ ID NO 10
<211> LENGTH: 7
<212> TYPE: PRT
<213> ORGANISM: Homo sapiens

<400> SEQUENCE: 10

Phe Gln Leu Ser Gly Gln Lys
1               5

<210> SEQ ID NO 11
<211> LENGTH: 10
<212> TYPE: PRT
<213> ORGANISM: Homo sapiens

<400> SEQUENCE: 11

His Ser Gly Leu Tyr Ala Cys Ser Val Arg
1               5                   10

<210> SEQ ID NO 12
<211> LENGTH: 14
<212> TYPE: PRT
<213> ORGANISM: Homo sapiens

<400> SEQUENCE: 12

Leu Pro Lys Pro Tyr Ile Thr Ile Asn Asn Leu Asn Pro Arg
1               5                   10

<210> SEQ ID NO 13
<211> LENGTH: 16
<212> TYPE: PRT
<213> ORGANISM: Homo sapiens

<400> SEQUENCE: 13

Ser Asp Pro Val Thr Leu Asn Val Leu Tyr Gly Pro Asp Leu Pro Arg
1               5                   10                  15

<210> SEQ ID NO 14

```
<211> LENGTH: 8
<212> TYPE: PRT
<213> ORGANISM: Homo sapiens

<400> SEQUENCE: 14

Tyr Gly Pro Ala Tyr Ser Gly Arg
1               5

<210> SEQ ID NO 15
<211> LENGTH: 19
<212> TYPE: PRT
<213> ORGANISM: Homo sapiens

<400> SEQUENCE: 15

Ala Cys Thr Asp Asn Pro Leu Glu Glu Glu Tyr Leu Ala Gln Leu Gln
1               5                   10                  15

Glu Ala Lys

<210> SEQ ID NO 16
<211> LENGTH: 27
<212> TYPE: PRT
<213> ORGANISM: Homo sapiens

<400> SEQUENCE: 16

Asp Leu Pro Ser Cys Pro Cys Ala Tyr Pro Leu Glu Ala Met Asp Ser
1               5                   10                  15

Pro Val Ser Leu Gln Asp Glu His Gln Gly Arg
            20                  25

<210> SEQ ID NO 17
<211> LENGTH: 27
<212> TYPE: PRT
<213> ORGANISM: Homo sapiens

<400> SEQUENCE: 17

Asp Leu Pro Ser Cys Pro Cys Ala Tyr Pro Leu Glu Ala Met Asp Ser
1               5                   10                  15

Pro Val Ser Leu Gln Asp Glu His Gln Gly Arg
            20                  25

<210> SEQ ID NO 18
<211> LENGTH: 10
<212> TYPE: PRT
<213> ORGANISM: Homo sapiens

<400> SEQUENCE: 18

Phe Asp Thr Thr Pro Trp Ile Leu Cys Lys
1               5                   10

<210> SEQ ID NO 19
<211> LENGTH: 9
<212> TYPE: PRT
<213> ORGANISM: Homo sapiens

<400> SEQUENCE: 19

Leu Asp Ile Tyr Gln Pro Thr Ala Arg
1               5

<210> SEQ ID NO 20
<211> LENGTH: 9
<212> TYPE: PRT
<213> ORGANISM: Homo sapiens

<400> SEQUENCE: 20
```

Pro Leu Arg Glu Glu Glu Ala Arg
1               5

<210> SEQ ID NO 21
<211> LENGTH: 22
<212> TYPE: PRT
<213> ORGANISM: Homo sapiens

<400> SEQUENCE: 21

Ser Met Leu Ser Gly Glu Ser Ser Thr Leu Ala Ala Gln His Cys Cys
1               5                   10                  15

Tyr Asp Glu Asp Ser Arg
            20

<210> SEQ ID NO 22
<211> LENGTH: 24
<212> TYPE: PRT
<213> ORGANISM: Homo sapiens

<400> SEQUENCE: 22

Thr Cys Asp Leu Pro Ser Cys Pro Gly Thr Glu Asp Lys Asp Thr Leu
1               5                   10                  15

Gly Leu Pro Ser Glu Glu Trp Lys
            20

<210> SEQ ID NO 23
<211> LENGTH: 14
<212> TYPE: PRT
<213> ORGANISM: Homo sapiens

<400> SEQUENCE: 23

Thr Arg Pro Cys Gly Tyr Gly Cys Thr Ala Thr Glu Thr Arg
1               5                   10

<210> SEQ ID NO 24
<211> LENGTH: 7
<212> TYPE: PRT
<213> ORGANISM: Homo sapiens

<400> SEQUENCE: 24

Tyr Leu Ser Gln Met Leu Arg
1               5

<210> SEQ ID NO 25
<211> LENGTH: 12
<212> TYPE: PRT
<213> ORGANISM: Homo sapiens

<400> SEQUENCE: 25

Glu Asp Ala Gly Ser Tyr Thr Leu His Ile Ile Lys
1               5                   10

<210> SEQ ID NO 26
<211> LENGTH: 9
<212> TYPE: PRT
<213> ORGANISM: Homo sapiens

<400> SEQUENCE: 26

Leu Phe Ile Pro Gln Ile Thr Pro Lys
1               5

<210> SEQ ID NO 27
<211> LENGTH: 15

```
<212> TYPE: PRT
<213> ORGANISM: Homo sapiens

<400> SEQUENCE: 27

Asn Ser Ala Thr Gly Glu Glu Ser Ser Thr Ser Leu Thr Ile Arg
1               5                   10                  15

<210> SEQ ID NO 28
<211> LENGTH: 16
<212> TYPE: PRT
<213> ORGANISM: Homo sapiens

<400> SEQUENCE: 28

Ser Asp Pro Val Thr Leu Asn Leu Leu His Gly Pro Asp Leu Pro Arg
1               5                   10                  15

<210> SEQ ID NO 29
<211> LENGTH: 16
<212> TYPE: PRT
<213> ORGANISM: Homo sapiens

<400> SEQUENCE: 29

Val Ile Ala Pro Pro Gly Leu Gly Thr Phe Ala Phe Asn Asn Pro Thr
1               5                   10                  15

<210> SEQ ID NO 30
<211> LENGTH: 11
<212> TYPE: PRT
<213> ORGANISM: Homo sapiens

<400> SEQUENCE: 30

Asp Ala Gly Thr Tyr Thr Leu His Ile Ile Lys
1               5                   10

<210> SEQ ID NO 31
<211> LENGTH: 20
<212> TYPE: PRT
<213> ORGANISM: Homo sapiens

<400> SEQUENCE: 31

Asp Val Leu Leu Leu Val His Asn Leu Pro Gln Asn Leu Pro Gly Tyr
1               5                   10                  15

Phe Trp Tyr Lys
            20

<210> SEQ ID NO 32
<211> LENGTH: 18
<212> TYPE: PRT
<213> ORGANISM: Homo sapiens

<400> SEQUENCE: 32

Gly Glu Met Thr Asp Leu Tyr His Tyr Ile Ile Ser Tyr Ile Val Asp
1               5                   10                  15

Gly Lys

<210> SEQ ID NO 33
<211> LENGTH: 11
<212> TYPE: PRT
<213> ORGANISM: Homo sapiens

<400> SEQUENCE: 33

Ile Ile Ile Tyr Gly Pro Ala Tyr Ser Gly Arg
1               5                   10
```

<210> SEQ ID NO 34
<211> LENGTH: 9
<212> TYPE: PRT
<213> ORGANISM: Homo sapiens

<400> SEQUENCE: 34

Ile Leu Ile Leu Pro Ser Val Thr Arg
1               5

<210> SEQ ID NO 35
<211> LENGTH: 12
<212> TYPE: PRT
<213> ORGANISM: Homo sapiens

<400> SEQUENCE: 35

Lys Asp Ala Gly Thr Tyr Thr Leu His Ile Ile Lys
1               5                   10

<210> SEQ ID NO 36
<211> LENGTH: 8
<212> TYPE: PRT
<213> ORGANISM: Homo sapiens

<400> SEQUENCE: 36

Leu Phe Ile Pro Gln Ile Thr Arg
1               5

<210> SEQ ID NO 37
<211> LENGTH: 26
<212> TYPE: PRT
<213> ORGANISM: Homo sapiens

<400> SEQUENCE: 37

Leu Ile Cys Asp Pro Glu Thr Leu Asp Ala Ser Tyr Leu Trp Trp Met
1               5                   10                  15

Asn Gly Gln Ser Leu Pro Val Thr His Arg
            20                  25

<210> SEQ ID NO 38
<211> LENGTH: 14
<212> TYPE: PRT
<213> ORGANISM: Homo sapiens

<400> SEQUENCE: 38

Leu Pro Ile Pro Tyr Ile Thr Ile Asn Asn Leu Asn Pro Arg
1               5                   10

<210> SEQ ID NO 39
<211> LENGTH: 10
<212> TYPE: PRT
<213> ORGANISM: Homo sapiens

<400> SEQUENCE: 39

Arg Gly Asp Glu Thr Arg Glu Glu Ile Arg
1               5                   10

<210> SEQ ID NO 40
<211> LENGTH: 11
<212> TYPE: PRT
<213> ORGANISM: Homo sapiens

<400> SEQUENCE: 40

Ser Asp Pro Val Thr Leu Asn Leu Leu Pro Lys
1               5                   10

```
<210> SEQ ID NO 41
<211> LENGTH: 16
<212> TYPE: PRT
<213> ORGANISM: Homo sapiens

<400> SEQUENCE: 41

Ser Asn Pro Val Ile Leu Asn Val Leu Tyr Gly Pro Asp Leu Pro Arg
1               5                   10                  15

<210> SEQ ID NO 42
<211> LENGTH: 9
<212> TYPE: PRT
<213> ORGANISM: Homo sapiens

<400> SEQUENCE: 42

Thr Leu Tyr Leu Phe Gly Val Thr Lys
1               5

<210> SEQ ID NO 43
<211> LENGTH: 14
<212> TYPE: PRT
<213> ORGANISM: Homo sapiens

<400> SEQUENCE: 43

Val Ser Gly Pro Cys His Gly Asp Leu Thr Glu Ser Gln Ser
1               5                   10

<210> SEQ ID NO 44
<211> LENGTH: 11
<212> TYPE: PRT
<213> ORGANISM: Homo sapiens

<400> SEQUENCE: 44

Tyr Ile Ala Gly Pro Tyr Glu Cys Glu Ile Arg
1               5                   10

<210> SEQ ID NO 45
<211> LENGTH: 22
<212> TYPE: PRT
<213> ORGANISM: Homo sapiens

<400> SEQUENCE: 45

Phe Thr Phe Thr Leu His Leu Glu Thr Pro Lys Pro Ser Ile Ser Ser
1               5                   10                  15

Ser Asn Leu Asn Pro Arg
            20

<210> SEQ ID NO 46
<211> LENGTH: 10
<212> TYPE: PRT
<213> ORGANISM: Homo sapiens

<400> SEQUENCE: 46

His Ser Gly Leu Tyr Val Cys Ser Val Arg
1               5                   10

<210> SEQ ID NO 47
<211> LENGTH: 9
<212> TYPE: PRT
<213> ORGANISM: Homo sapiens

<400> SEQUENCE: 47

Thr Leu Phe Leu Leu Gly Val Thr Lys
```

```
<210> SEQ ID NO 48
<211> LENGTH: 11
<212> TYPE: PRT
<213> ORGANISM: Homo sapiens

<400> SEQUENCE: 48

Tyr Thr Ala Gly Pro Tyr Glu Cys Glu Ile Arg
1               5                   10

<210> SEQ ID NO 49
<211> LENGTH: 16
<212> TYPE: PRT
<213> ORGANISM: Homo sapiens

<400> SEQUENCE: 49

Phe Gln Gln Ser Gly Gln Asn Leu Phe Ile Pro Gln Ile Thr Thr Lys
1               5                   10                  15

<210> SEQ ID NO 50
<211> LENGTH: 10
<212> TYPE: PRT
<213> ORGANISM: Homo sapiens

<400> SEQUENCE: 50

Ile Gly Leu Leu Pro Leu Leu Asn Pro Thr
1               5                   10

<210> SEQ ID NO 51
<211> LENGTH: 12
<212> TYPE: PRT
<213> ORGANISM: Homo sapiens

<400> SEQUENCE: 51

Cys Arg Pro Ile Asn Ala Thr Leu Ala Val Glu Lys
1               5                   10

<210> SEQ ID NO 52
<211> LENGTH: 10
<212> TYPE: PRT
<213> ORGANISM: Homo sapiens

<400> SEQUENCE: 52

Asp His Pro Leu Thr Cys Asp Asp Pro Arg
1               5                   10

<210> SEQ ID NO 53
<211> LENGTH: 20
<212> TYPE: PRT
<213> ORGANISM: Homo sapiens

<400> SEQUENCE: 53

Gly Val Asn Pro Val Val Ser Tyr Ala Val Ala Leu Ser Cys Gln Cys
1               5                   10                  15

Ala Leu Cys Arg
            20

<210> SEQ ID NO 54
<211> LENGTH: 17
<212> TYPE: PRT
<213> ORGANISM: Homo sapiens

<400> SEQUENCE: 54
```

```
Val Leu Gln Gly Val Leu Pro Ala Leu Pro Gln Val Val Cys Asn Tyr
1               5                   10                  15

Arg

<210> SEQ ID NO 55
<211> LENGTH: 7
<212> TYPE: PRT
<213> ORGANISM: Homo sapiens

<400> SEQUENCE: 55

Lys Thr Met Leu Val Gln Lys
1               5

<210> SEQ ID NO 56
<211> LENGTH: 8
<212> TYPE: PRT
<213> ORGANISM: Homo sapiens

<400> SEQUENCE: 56

Val Thr Val Met Gly Gly Phe Lys
1               5

<210> SEQ ID NO 57
<211> LENGTH: 8
<212> TYPE: PRT
<213> ORGANISM: Homo sapiens

<400> SEQUENCE: 57

Val Thr Val Met Gly Gly Phe Lys
1               5

<210> SEQ ID NO 58
<211> LENGTH: 7
<212> TYPE: PRT
<213> ORGANISM: Homo sapiens

<400> SEQUENCE: 58

Ala Asp Leu Glu Leu Pro Arg
1               5

<210> SEQ ID NO 59
<211> LENGTH: 16
<212> TYPE: PRT
<213> ORGANISM: Homo sapiens

<400> SEQUENCE: 59

Ala Phe Cys Asn Tyr Asp Gly Gly Asp Cys Cys Thr Ser Thr Val Lys
1               5                   10                  15

<210> SEQ ID NO 60
<211> LENGTH: 7
<212> TYPE: PRT
<213> ORGANISM: Homo sapiens

<400> SEQUENCE: 60

Ala Leu Tyr Phe Ser Gly Arg
1               5

<210> SEQ ID NO 61
<211> LENGTH: 27
<212> TYPE: PRT
<213> ORGANISM: Homo sapiens

<400> SEQUENCE: 61
```

```
Ala Tyr Phe Ser Gln Pro Met Val Ala Ala Val Ile Val His Leu
1               5                   10                  15

Val Thr Asp Gly Thr Tyr Tyr Gly Asp Gln Lys
            20                  25
```

<210> SEQ ID NO 62
<211> LENGTH: 27
<212> TYPE: PRT
<213> ORGANISM: Homo sapiens

<400> SEQUENCE: 62

```
Ala Tyr Phe Ser Gln Pro Met Val Ala Ala Val Ile Val His Leu
1               5                   10                  15

Val Thr Asp Gly Thr Tyr Tyr Gly Asp Gln Lys
            20                  25
```

<210> SEQ ID NO 63
<211> LENGTH: 9
<212> TYPE: PRT
<213> ORGANISM: Homo sapiens

<400> SEQUENCE: 63

```
Ala Tyr Leu Asp Val Asn Glu Leu Lys
1               5
```

<210> SEQ ID NO 64
<211> LENGTH: 18
<212> TYPE: PRT
<213> ORGANISM: Homo sapiens

<400> SEQUENCE: 64

```
Cys Glu Asp Ser Asp Ala Ser Gln Gly Leu Gly Ser Asn Val Ile His
1               5                   10                  15

Cys Arg
```

<210> SEQ ID NO 65
<211> LENGTH: 16
<212> TYPE: PRT
<213> ORGANISM: Homo sapiens

<400> SEQUENCE: 65

```
Cys Tyr Phe His Asp Gly Asp Gly Val Cys Glu Glu Phe Glu Gln Lys
1               5                   10                  15
```

<210> SEQ ID NO 66
<211> LENGTH: 10
<212> TYPE: PRT
<213> ORGANISM: Homo sapiens

<400> SEQUENCE: 66

```
Asp Ile Pro His Trp Leu Asn Pro Thr Arg
1               5                   10
```

<210> SEQ ID NO 67
<211> LENGTH: 16
<212> TYPE: PRT
<213> ORGANISM: Homo sapiens

<400> SEQUENCE: 67

```
Asp Pro Pro Leu Gln Met Asp Val Ala Ser Ile Leu His Leu Asn Arg
1               5                   10                  15
```

<210> SEQ ID NO 68

```
<211> LENGTH: 11
<212> TYPE: PRT
<213> ORGANISM: Homo sapiens

<400> SEQUENCE: 68

Asp Gln Gly Glu Gln Cys Asp Asp Met Asn Lys
1               5                   10

<210> SEQ ID NO 69
<211> LENGTH: 14
<212> TYPE: PRT
<213> ORGANISM: Homo sapiens

<400> SEQUENCE: 69

Asp Gln Ser His Asp Leu Gly Leu His Val Leu Ser Cys Arg
1               5                   10

<210> SEQ ID NO 70
<211> LENGTH: 13
<212> TYPE: PRT
<213> ORGANISM: Homo sapiens

<400> SEQUENCE: 70

Glu Ala Glu Gly His Pro Asp Val Glu Gln Pro Cys Lys
1               5                   10

<210> SEQ ID NO 71
<211> LENGTH: 28
<212> TYPE: PRT
<213> ORGANISM: Homo sapiens

<400> SEQUENCE: 71

Glu Ile Leu Ser Asp Met Glu Thr His Gly Ala His Thr Ala Leu Pro
1               5                   10                  15

Gln Leu Leu Leu Gln Glu Asn Trp Asp Asn Val Lys
            20                  25

<210> SEQ ID NO 72
<211> LENGTH: 13
<212> TYPE: PRT
<213> ORGANISM: Homo sapiens

<400> SEQUENCE: 72

Glu Leu Gly Ser Ala Cys His Leu Cys Leu Glu Gly Arg
1               5                   10

<210> SEQ ID NO 73
<211> LENGTH: 15
<212> TYPE: PRT
<213> ORGANISM: Homo sapiens

<400> SEQUENCE: 73

Glu Gln Val Asp Phe Gln His His Gln Leu Ala Glu Ala Phe Lys
1               5                   10                  15

<210> SEQ ID NO 74
<211> LENGTH: 18
<212> TYPE: PRT
<213> ORGANISM: Homo sapiens

<400> SEQUENCE: 74

Phe His Gly Leu Tyr Gln Cys Thr Asn Gly Phe Gln Phe Asn Ser Glu
1               5                   10                  15

Cys Arg
```

```
<210> SEQ ID NO 75
<211> LENGTH: 11
<212> TYPE: PRT
<213> ORGANISM: Homo sapiens

<400> SEQUENCE: 75

Gly Ala Thr Glu Glu Pro Ser Pro Pro Ser Arg
1               5                   10

<210> SEQ ID NO 76
<211> LENGTH: 17
<212> TYPE: PRT
<213> ORGANISM: Homo sapiens

<400> SEQUENCE: 76

Gly Cys Glu Pro Phe Met Gly Asp Asn Tyr Cys Asp Ala Ile Asn Asn
1               5                   10                  15

Arg

<210> SEQ ID NO 77
<211> LENGTH: 18
<212> TYPE: PRT
<213> ORGANISM: Homo sapiens

<400> SEQUENCE: 77

Gly Glu Thr Tyr Ser Pro Ala Glu Gln Ser Cys Val His Phe Ala Cys
1               5                   10                  15

Glu Lys

<210> SEQ ID NO 78
<211> LENGTH: 10
<212> TYPE: PRT
<213> ORGANISM: Homo sapiens

<400> SEQUENCE: 78

Gly Tyr Ile Glu His Phe Ser Leu Trp Lys
1               5                   10

<210> SEQ ID NO 79
<211> LENGTH: 20
<212> TYPE: PRT
<213> ORGANISM: Homo sapiens

<400> SEQUENCE: 79

Ile Lys Cys Glu Asp Ser Asp Ala Ser Gln Gly Leu Gly Ser Asn Val
1               5                   10                  15

Ile His Cys Arg
            20

<210> SEQ ID NO 80
<211> LENGTH: 34
<212> TYPE: PRT
<213> ORGANISM: Homo sapiens

<400> SEQUENCE: 80

Lys Pro Ala Pro Val Ala Leu Ala Pro Gln Val Leu Gly His Thr Thr
1               5                   10                  15

Asp Ser Val Thr Leu Glu Trp Phe Pro Pro Ile Asp Gly His Phe Phe
                20                  25                  30

Glu Arg
```

```
<210> SEQ ID NO 81
<211> LENGTH: 13
<212> TYPE: PRT
<213> ORGANISM: Homo sapiens

<400> SEQUENCE: 81

Leu Asp Gly Ser Thr His Leu Asn Ile Phe Phe Ala Lys
1               5                   10

<210> SEQ ID NO 82
<211> LENGTH: 10
<212> TYPE: PRT
<213> ORGANISM: Homo sapiens

<400> SEQUENCE: 82

Leu Ile Leu Ala Asn Cys Asp Ile Ser Lys
1               5                   10

<210> SEQ ID NO 83
<211> LENGTH: 23
<212> TYPE: PRT
<213> ORGANISM: Homo sapiens

<400> SEQUENCE: 83

Asn Asn Pro Leu Ile Ile Pro Val Val His Asp Leu Ser Gln Pro Phe
1               5                   10                  15

Tyr His Ser Gln Ala Val Arg
            20

<210> SEQ ID NO 84
<211> LENGTH: 13
<212> TYPE: PRT
<213> ORGANISM: Homo sapiens

<400> SEQUENCE: 84

Gln Glu Val Ser Phe Asn Cys Ile Asp Glu Pro Ser Arg
1               5                   10

<210> SEQ ID NO 85
<211> LENGTH: 11
<212> TYPE: PRT
<213> ORGANISM: Homo sapiens

<400> SEQUENCE: 85

Arg Leu Ile Leu Ala Asn Cys Asp Ile Ser Lys
1               5                   10

<210> SEQ ID NO 86
<211> LENGTH: 15
<212> TYPE: PRT
<213> ORGANISM: Homo sapiens

<400> SEQUENCE: 86

Ser Phe Asp Asn Phe Asp Pro Val Thr Leu Ser Ser Cys Gln Arg
1               5                   10                  15

<210> SEQ ID NO 87
<211> LENGTH: 11
<212> TYPE: PRT
<213> ORGANISM: Homo sapiens

<400> SEQUENCE: 87

Ser Pro Ala Val Ile Thr Gly Leu Tyr Asp Lys
1               5                   10
```

```
<210> SEQ ID NO 88
<211> LENGTH: 15
<212> TYPE: PRT
<213> ORGANISM: Homo sapiens

<400> SEQUENCE: 88

Ser Gln Thr Gly Pro Ser Val Thr Val Thr Cys Thr Glu Gly Lys
1               5                   10                  15

<210> SEQ ID NO 89
<211> LENGTH: 20
<212> TYPE: PRT
<213> ORGANISM: Homo sapiens

<400> SEQUENCE: 89

Ser Tyr Leu Pro Gly Gln Trp Val Tyr Leu Ala Ala Thr Tyr Asp Gly
1               5                   10                  15

Gln Phe Met Lys
            20

<210> SEQ ID NO 90
<211> LENGTH: 8
<212> TYPE: PRT
<213> ORGANISM: Homo sapiens

<400> SEQUENCE: 90

Thr Gly Tyr Val Leu Gln Ile Arg
1               5

<210> SEQ ID NO 91
<211> LENGTH: 16
<212> TYPE: PRT
<213> ORGANISM: Homo sapiens

<400> SEQUENCE: 91

Val Ser Phe Ser Ser Pro Leu Val Ala Ile Ser Gly Val Ala Leu Arg
1               5                   10                  15

<210> SEQ ID NO 92
<211> LENGTH: 8
<212> TYPE: PRT
<213> ORGANISM: Homo sapiens

<400> SEQUENCE: 92

Val Val Cys Thr Ala Gly Leu Lys
1               5

<210> SEQ ID NO 93
<211> LENGTH: 16
<212> TYPE: PRT
<213> ORGANISM: Homo sapiens

<400> SEQUENCE: 93

Val Val Asn Leu Tyr Glu Asp Asp His Lys Asn Pro Thr Val Thr Arg
1               5                   10                  15

<210> SEQ ID NO 94
<211> LENGTH: 19
<212> TYPE: PRT
<213> ORGANISM: Homo sapiens

<400> SEQUENCE: 94

Val Val Arg Asp Pro Pro Leu Gln Met Asp Val Ala Ser Ile Leu His
```

-continued

```
1               5                  10                  15

Leu Asn Arg

<210> SEQ ID NO 95
<211> LENGTH: 12
<212> TYPE: PRT
<213> ORGANISM: Homo sapiens

<400> SEQUENCE: 95

Trp Tyr Pro His Pro Ala Leu Ile His Cys Val Lys
1               5                  10

<210> SEQ ID NO 96
<211> LENGTH: 6
<212> TYPE: PRT
<213> ORGANISM: Homo sapiens

<400> SEQUENCE: 96

Tyr Phe Phe Ser Leu Lys
1               5

<210> SEQ ID NO 97
<211> LENGTH: 11
<212> TYPE: PRT
<213> ORGANISM: Homo sapiens

<400> SEQUENCE: 97

Tyr His Gly Ala Gln Cys Thr Val Ser Cys Arg
1               5                  10

<210> SEQ ID NO 98
<211> LENGTH: 19
<212> TYPE: PRT
<213> ORGANISM: Homo sapiens

<400> SEQUENCE: 98

Ala His Gln Leu Ala Ile Asp Thr Tyr Gln Glu Phe Glu Glu Thr Tyr
1               5                  10                  15

Ile Pro Lys

<210> SEQ ID NO 99
<211> LENGTH: 12
<212> TYPE: PRT
<213> ORGANISM: Homo sapiens

<400> SEQUENCE: 99

Asp Leu Glu Glu Gly Ile Gln Thr Leu Met Gly Arg
1               5                  10

<210> SEQ ID NO 100
<211> LENGTH: 12
<212> TYPE: PRT
<213> ORGANISM: Homo sapiens

<400> SEQUENCE: 100

Asp Leu Glu Glu Gly Ile Gln Thr Leu Met Gly Arg
1               5                  10

<210> SEQ ID NO 101
<211> LENGTH: 10
<212> TYPE: PRT
<213> ORGANISM: Homo sapiens

<400> SEQUENCE: 101
```

Asp Met Asp Lys Val Glu Thr Phe Leu Arg
1               5                   10

<210> SEQ ID NO 102
<211> LENGTH: 10
<212> TYPE: PRT
<213> ORGANISM: Homo sapiens

<400> SEQUENCE: 102

Asp Met Asp Lys Val Glu Thr Phe Leu Arg
1               5                   10

<210> SEQ ID NO 103
<211> LENGTH: 13
<212> TYPE: PRT
<213> ORGANISM: Homo sapiens

<400> SEQUENCE: 103

Phe Asp Thr Asn Ser His Asn His Asp Ala Leu Leu Lys
1               5                   10

<210> SEQ ID NO 104
<211> LENGTH: 11
<212> TYPE: PRT
<213> ORGANISM: Homo sapiens

<400> SEQUENCE: 104

Lys Asp Met Asp Lys Val Glu Thr Phe Leu Arg
1               5                   10

<210> SEQ ID NO 105
<211> LENGTH: 11
<212> TYPE: PRT
<213> ORGANISM: Homo sapiens

<400> SEQUENCE: 105

Lys Asp Met Asp Lys Val Glu Thr Phe Leu Arg
1               5                   10

<210> SEQ ID NO 106
<211> LENGTH: 11
<212> TYPE: PRT
<213> ORGANISM: Homo sapiens

<400> SEQUENCE: 106

Leu Phe Asp His Ala Met Leu Gln Ala His Arg
1               5                   10

<210> SEQ ID NO 107
<211> LENGTH: 11
<212> TYPE: PRT
<213> ORGANISM: Homo sapiens

<400> SEQUENCE: 107

Leu Phe Asp His Ala Met Leu Gln Ala His Arg
1               5                   10

<210> SEQ ID NO 108
<211> LENGTH: 9
<212> TYPE: PRT
<213> ORGANISM: Homo sapiens

<400> SEQUENCE: 108

Asn Tyr Gly Leu Leu Tyr Cys Phe Arg

```
1               5

<210> SEQ ID NO 109
<211> LENGTH: 21
<212> TYPE: PRT
<213> ORGANISM: Homo sapiens

<400> SEQUENCE: 109

Ser Met Phe Ala Asn Asn Leu Val Tyr Asp Thr Ser Asp Ser Asp Asp
1               5                   10                  15

Tyr His Leu Leu Lys
            20

<210> SEQ ID NO 110
<211> LENGTH: 21
<212> TYPE: PRT
<213> ORGANISM: Homo sapiens

<400> SEQUENCE: 110

Ser Met Phe Ala Asn Asn Leu Val Tyr Asp Thr Ser Asp Ser Asp Asp
1               5                   10                  15

Tyr His Leu Leu Lys
            20

<210> SEQ ID NO 111
<211> LENGTH: 7
<212> TYPE: PRT
<213> ORGANISM: Homo sapiens

<400> SEQUENCE: 111

Ser Asn Leu Glu Leu Leu Arg
1               5

<210> SEQ ID NO 112
<211> LENGTH: 9
<212> TYPE: PRT
<213> ORGANISM: Homo sapiens

<400> SEQUENCE: 112

His Leu Trp Tyr Leu Leu Asp Leu Lys
1               5

<210> SEQ ID NO 113
<211> LENGTH: 8
<212> TYPE: PRT
<213> ORGANISM: Homo sapiens

<400> SEQUENCE: 113

Gln Met Glu Glu Pro Cys Arg Phe
1               5

<210> SEQ ID NO 114
<211> LENGTH: 8
<212> TYPE: PRT
<213> ORGANISM: Homo sapiens

<400> SEQUENCE: 114

Gln Met Glu Glu Pro Cys Arg Phe
1               5

<210> SEQ ID NO 115
<211> LENGTH: 20
<212> TYPE: PRT
<213> ORGANISM: Homo sapiens
```

-continued

```
<400> SEQUENCE: 115

Val His Ile Thr Ser Leu Leu Pro Thr Pro Glu Asp Asn Leu Glu Ile
1               5                   10                  15

Val Leu His Arg
            20

<210> SEQ ID NO 116
<211> LENGTH: 14
<212> TYPE: PRT
<213> ORGANISM: Homo sapiens

<400> SEQUENCE: 116

Val Leu Val Glu Asp Asp Glu Ile Met Gln Gly Phe Ile Arg
1               5                   10

<210> SEQ ID NO 117
<211> LENGTH: 14
<212> TYPE: PRT
<213> ORGANISM: Homo sapiens

<400> SEQUENCE: 117

Val Leu Val Glu Asp Asp Glu Ile Met Gln Gly Phe Ile Arg
1               5                   10

<210> SEQ ID NO 118
<211> LENGTH: 10
<212> TYPE: PRT
<213> ORGANISM: Homo sapiens

<400> SEQUENCE: 118

Val Pro Ala Met Asp Ile Pro Gln Thr Lys
1               5                   10
```

METHODS AND COMPOSITIONS FOR DIAGNOSIS OF ECTOPIC PREGNANCY

CROSS REFERENCE TO RELATED APPLICATIONS

This application claims the benefit of the priority of U.S. Provisional Patent Application No. 61/443,026, filed Feb. 15, 2011, which is incorporated herein by reference.

STATEMENT REGARDING FEDERALLY SPONSORED RESEARCH OR DEVELOPMENT

This invention was made with government support under Grant No. 5R01HD036455 and NCI Cancer Core Grant CA10815 awarded by the National Institutes of Health. The government has certain rights in this invention.

BACKGROUND OF THE INVENTION

Ectopic Pregnancy (EP) is a clinical condition that occurs when the embryo implants at a site other than in the uterus, typically the fallopian tube. As the fetus grows, this condition becomes life-threatening due to potential tubal rupture and internal hemorrhage. The incidence of EP is increasing due to a number of factors, and it is now the second-most-common cause of maternal death in the first trimester of pregnancy. Nearly a third of all cases do not exhibit any clinical signs and 9% have no symptoms prior to tubal rupture.

EP is currently diagnosed using a combination of transvaginal ultrasound and serial detections of the biomarker, β-human chorionic gonadotrophin (β-hCG, gene name: CGB) levels, in serum. However, EP, for which there is no good experimental model system, remains difficult to diagnose at an early stage. Approximately 50% of patients with this condition initially are misdiagnosed—resulting in significant morbidity and mortality.

Efforts to diagnose EP at an early point in the pregnancy using blood tests have been hampered because of the lack of useful and reliable serum biomarkers which reliably characterize EP. Considerable difficulty in determining and identifying biomarkers for EP diagnosis has been attributed to a number of factors such as the high complexity of serum proteomes; a wide protein abundance range spanning more than 10 orders of magnitude; the presence of most clinically useful biomarkers at very low levels; a high patient-to-patient variability; and potential biases due to variations in sample collection and processing. Serum's complexity and wide dynamic range, combined with the need to detect low-abundance proteins, requires that extensive fractionation be used in order to achieve a good depth of analysis, which limits throughput. However, patient-to-patient heterogeneity requires that relatively large numbers of patient samples be analyzed.

Common compromises for dealing with these opposing factors include use of mouse or in vitro models, pooling of patient samples for the discovery phase, and/or analyzing less than ideal numbers of patients in the discovery phase followed by evaluation of candidate biomarkers in larger numbers of patients. All of these methods have not lead to a reliable early diagnostic test for EP to date.

SUMMARY OF THE INVENTION

In one aspect, a diagnostic reagent or kit for use in diagnosing an ectopic pregnancy in a mammalian subject includes: (a) one or more ligands, wherein each ligand binds to a different gene expression product or protein selected from Table 2 and/or from FIG. 7, or fragments thereof; or (b) one or more polynucleotides or oligonucleotides, wherein each polynucleotide or oligonucleotide hybridizes to a different gene, gene fragment, gene transcript or expression product encoding the biomarkers selected from Table 2 and/or from FIG. 7. In one embodiment, at least one of the polynucleotide or oligonucleotide sequence, or ligand, forming the reagent or kit is associated with a detectable label or with a substrate. In other embodiments, the reagent or kit is designed to permit detection of selected multiple members of Table 2 and/or from FIG. 7 that form a gene profile or protein expression level signature characteristic of ectopic pregnancy.

In still another aspect are reagents including the biomarker proteins or fragments thereof associated with a detectable label or immobilized on a suitable substrate.

In another aspect, a kit containing multiple reagents forming an EP biomarker signature is provided.

In another aspect, a method for diagnosing an ectopic pregnancy in a female mammalian subject includes measuring in a biological fluid sample of the subject the expression level of a protein from Table 2 or FIG. 7, or a peptide fragment thereof and/or the expression of a biomarker gene, gene fragment, gene transcript or expression product encoding the biomarker; and comparing the subject's selected biomarker protein or biomarker gene, gene fragment, gene transcript or expression product expression level with the level of the same biomarker or its gene, gene fragment, gene transcript or expression product in the biological fluid of a reference or control female mammalian subject having a normal intrauterine pregnancy (IUP). Changes in expression of the subject's selected biomarker or biomarker gene, gene fragment, gene transcript or expression product from those of the reference or control are characteristic of and correlate with a diagnosis of ectopic pregnancy.

In still other aspects, optional labels, label systems, substrates for immobilization and controls may be included in or with the reagent or kit, and used in these diagnostic methods to identify a characteristic change in the level of expression of the one or more gene, gene fragment, gene transcript or protein expression product indicative of the diagnosis of ectopic pregnancy.

In another aspect, use of the diagnostic reagents described herein in the methods for the diagnosis of EP are provided.

Other aspects and advantages of these compositions and methods are described further in the following detailed description of the preferred embodiments thereof.

BRIEF DESCRIPTION OF THE DRAWINGS

FIGS. 1A-1C lines with round datapoints indicate peptides that passed both the Elucidator ANOVA test and the more stringent probability of misclassification test ($P_m$). Lines with square datapoints indicate peptides that only failed the probability of misclassification test. Lines with X datapoints indicate peptides that failed both statistical tests.

FIG. 1A is a peptide trend plot for the high-priority candidate EP biomarker ADAM12, where all peptides (see list in FIG. 6) passed both statistical analyses.

FIG. 1B is a peptide trend plot for the high-priority candidate biomarker ISM2, where a single peptide failed the probability of misclassification test. See FIG. 6.

FIG. 1C is a peptide trend plot for an additional candidate biomarker, PAEP, which shows substantial noise at the peptide level, with only two peptides passing both statistical tests, the majority of peptides failing the probability of misclassification test, and one peptide that failed both tests. This protein was retained as a candidate biomarker because of previously reported association with EP. See FIG. 6.

FIG. 5A is a scatter plot for candidate EP biomarker ADAM12-prodomain. MRM intensities (summed for gel slices 12-15) for individual samples are shown. Responses for individual peptides were normalized and multiplied by $10^5$ to acquire an adjusted intensity value, similar to individual intensity values shown in FIGS. 4A-4B. Samples were analyzed statistically using the unpaired t-test with Welch's correction and P-values are indicated below the protein name.

FIG. 5B is a scatter plot for candidate EP biomarker PAEP. MRM intensities (summed for gel slices 12-15) for individual samples are shown. Responses for individual peptides were normalized and multiplied by $10^5$ to acquire an adjusted intensity value, similar to individual intensity values shown in FIGS. 4C-4D. Samples were analyzed statistically using the unpaired t-test with Welch's correction and P-values are indicated below the protein name.

FIG. 5C is a scatter plot for candidate EP biomarker CGA. MRM intensities for individual samples, responses for individual peptides, analysis and P-value were as described in FIG. 5A.

FIG. 5D is a scatter plot for candidate EP biomarker CGB. MRM intensities for individual samples, responses for individual peptides, analysis and P-value were as described in FIG. 5A.

FIG. 5E is a scatter plot for candidate EP biomarker CSH1. MRM intensities for individual samples, responses for individual peptides, analysis and P-value were as described in FIG. 5A. Data for the CSH1 are shown on both a linear scale for comparison to other biomarkers.

FIG. 5F is a scatter plot for candidate EP biomarker CSH1 as described in FIG. 5E, but shown on a log scale to better illustrate differences between EP and IUP.

FIG. 7 is a list of 70 putative biomarker candidates initially identified from the Rosetta Elucidator analysis described below. A list of peptide sequences and intensities for additional putative candidate biomarkers of FIG. 7 that are not listed in Table 2 can be found at Beer et al, J.

Proteome Research, 10(3):1126-38 (2011) and in FIG. 10 of U.S. Provisional Patent Application No. 61/443,026, incorporated by reference herein.

Figure 8:
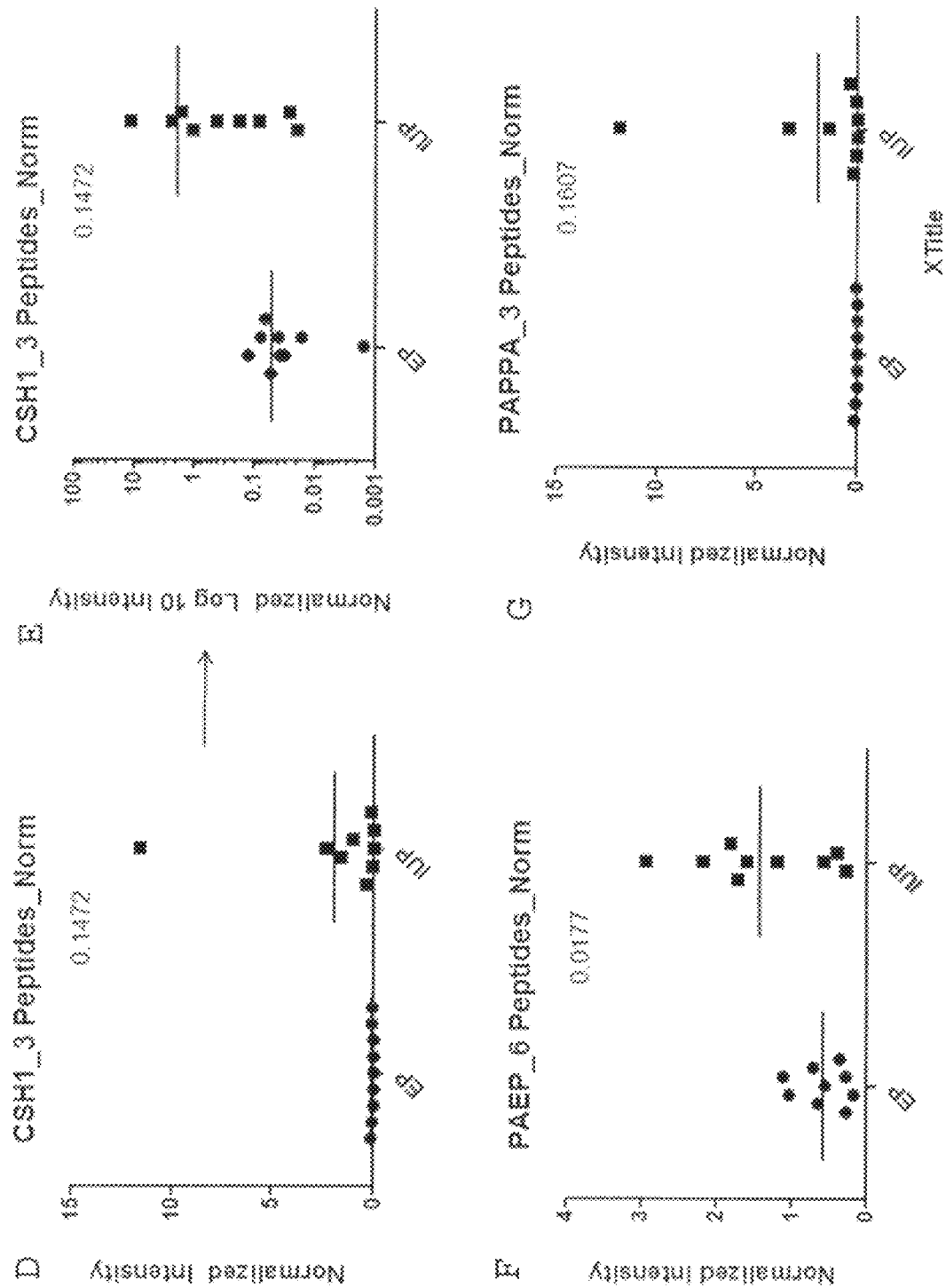
Figure 8:
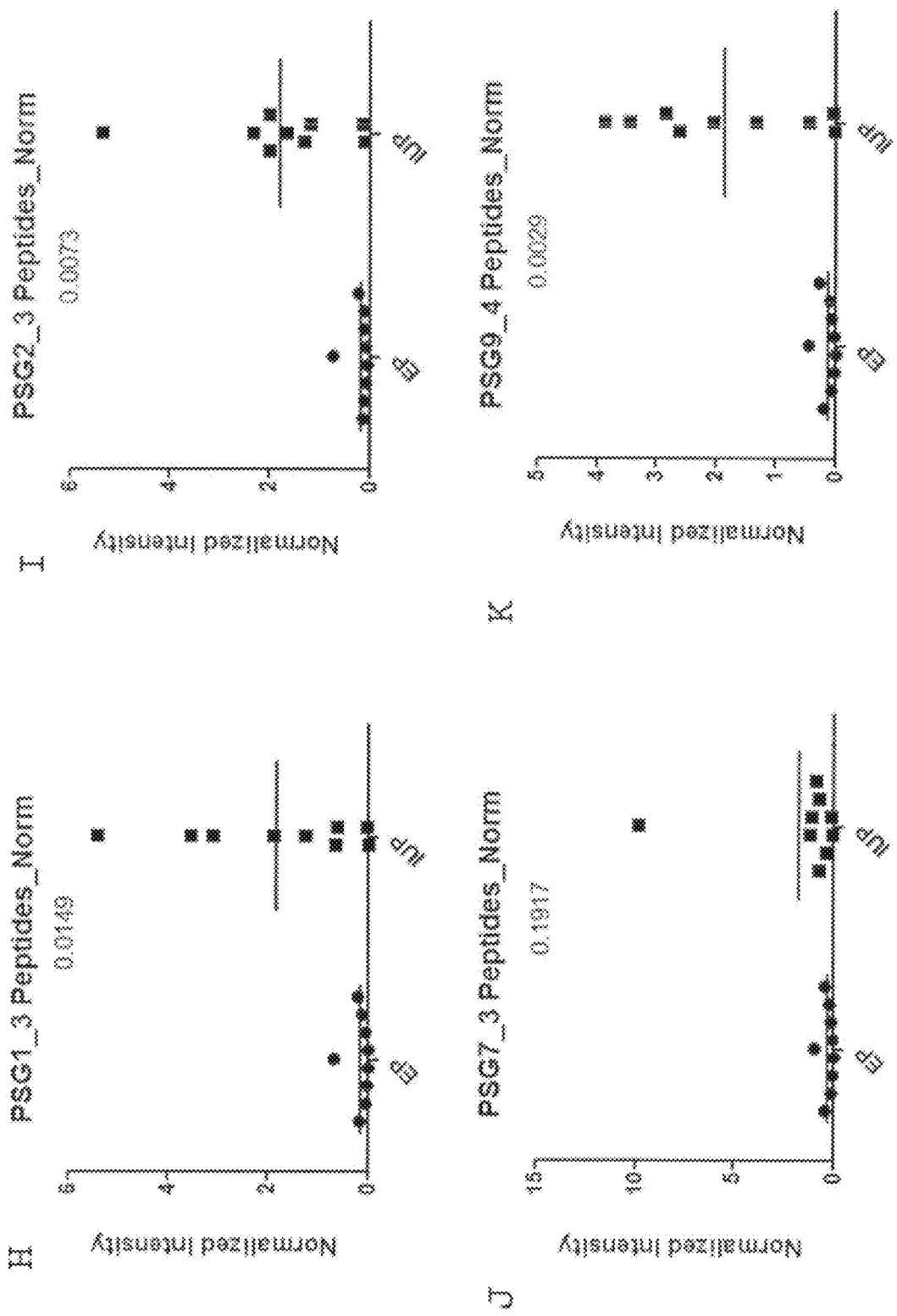
Figure 8:
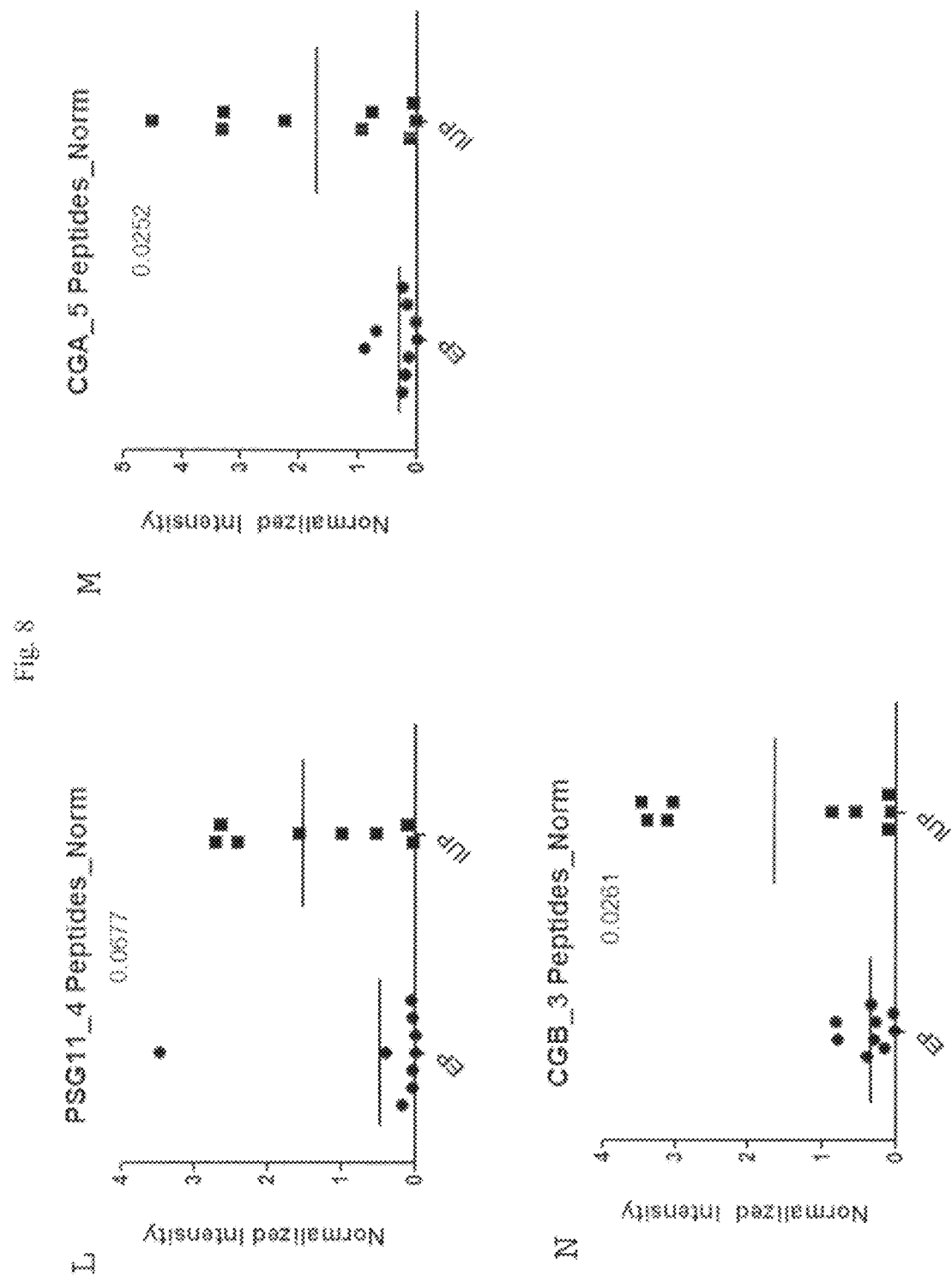

FIGS. 8A-8N are intensity graphs for the biomarkers ISM2 (4 peptides), ADAM12Pro (3 peptides); ADAM12EC (3 peptides), CSH1 (normalized log intensities for 3 peptides); PAEP (6 peptides), PAPPA (3 peptides); PSG1 (3 peptides); PSG2 (3 peptides); PSG7 (3 peptides), PSG9 (4 peptides), PSG11 (4 peptides), CGA (5 peptides) and CGB (3 peptides).

DETAILED DESCRIPTION OF THE INVENTION

The compositions and methods described herein provide means for early detection of ectopic pregnancy (EP) utilizing certain identified biomarkers, which display characteristic expression level in biological fluids of subjects with EP in contrast to the same fluids of subjects with normal intrauterine pregnancies (IUP). These compositions and methods permit diagnosis of EP in a more accurate and less invasive manner than currently available.

In one embodiment, the compositions and methods allow the detection and measurement of the expression levels of one or more "target" biomarker protein or peptide fragment thereof a biological fluid. In another embodiment, the compositions and methods allow the detection and measurement of the expression levels of one or more "target" biomarker gene, gene fragment, or gene transcript in biological fluids. Diagnostic reagents that can detect and measure these targets and methods for evaluating the level of these targets vs. their levels in normal IUP are valuable tools in the early detection of EP.

As described in the Examples below, the inventors identified specific fragments and isoforms of protein families present in the serum of patients with EP. The identification of such a panel of biomarkers provides a critical, more precise basis of knowledge to incorporate into pre-clinical and clinical diagnostic assays targeting these biomarkers.

I. DEFINITIONS

"Patient" or "subject" as used herein means a female mammalian animal, including a human, a veterinary or farm animal, a domestic animal or pet, and animals normally used for clinical research. In one embodiment, the subject of these methods and compositions is a human.

"Control" or "Control subject" as used herein refers to both an individual female with IUP or the pooled biological fluids (e.g., sera) from multiple females with IUP or numerical or graphical averages of the expression levels of the selected biomarkers obtained from large groups of females with IUP. Such controls are the types that are commonly used in similar diagnostic assays for other biomarkers. Selection of the particular class of controls depends upon the use to which the diagnostic methods and compositions are to be put by the physician. As used herein, the term "predetermined control" refers to a numerical level, average, mean or average range of the expression of a biomarker in a defined population. The predetermined control level is preferably provided by using the same assay technique as is used for measurement of the subject's biomarker levels, to avoid any error in standardization. For example, the control may comprise a single healthy pregnant mammalian subject at the same time of pregnancy as the subject. In another embodiment, the control comprises a population of multiple healthy pregnant mammalian subjects at the same time of pregnancy as the subject or multiple healthy IUP mammalian subjects. In another embodiment, the control comprises the same subject at an earlier time in the pregnancy. In yet another embodiment, the control comprises one or multiple subjects with one or more clinical indicators of EP, but who did not develop EP. In addition, a predetermined control may also be a negative predetermined control. In one embodiment, a negative predetermined control comprises one or multiple subjects who have EP. The control can refer to a numerical average, mean or average range of the expression of one or more biomarkers, in a defined population, rather than a single subject.

"Sample" as used herein means any biological fluid or tissue that contains the EP biomarkers. The most suitable samples for use in the methods and with the compositions are blood samples, including serum, plasma, whole blood, and peripheral blood. It is also anticipated that other biological fluids, such as saliva or urine, vaginal or cervical secretions, amniotic fluid, and placental fluid may be used similarly. Such samples may further be diluted with saline, buffer or a physiologically acceptable diluent. Alternatively, such samples are concentrated by conventional means.

By "change in expression" is meant an increased expression level of a selected biomarker, or upregulation of the genes or transcript encoding it in comparison to the reference or control; a decreased expression level of a selected biomarker or a downregulation of the genes or transcript encoding it in comparison to the reference or control; or a combination of certain increased/upregulated and decreased/down regulated biomarkers. The degree of change in target expression can vary with each individual and is subject to variation with each population and days or weeks of the pregnancy. For example, in one embodiment, a large change, e.g., 2-3 fold increase or decrease in a small number of biomarkers, e.g., from 1 to 9 characteristic biomarkers, is statistically significant. In another embodiment, a smaller relative change in about 10, 20, 24, 29, or 30 or more biomarkers is statistically significant.

By "target biomarker" or "target biomarker signature" as used herein is meant those proteins/peptides or the genes/transcripts encoding same, the expression of which changes (either in an up-regulated or down-regulated manner) characteristically in the presence of an ectopic pregnancy from that in an IUP. In one embodiment, at least one target biomarker forms a suitable biomarker signature for use in the methods and compositions. In one embodiment, at least two target biomarkers form a suitable biomarker signature for use in the methods and compositions. In another embodiment, at least five biomarkers form a suitable biomarker signature for use in the methods and compositions. In still further embodiments, at least 9, at least 12, at least 15, at least 20, 30, 40, 50 or at least 60 of the biomarkers including any numbers therebetween identified in FIG. 7 form a suitable biomarker signature for the diagnosis of EP. Specific biomarker signatures can include any combination of EP biomarkers employing at least one biomarker from (i) to (vii) identified herein and including all 12 biomarkers in Table 2, as well as other combinations with the biomarkers of FIG. 7. The biomarkers identified in FIGS. 8, 9, 10 and in Table 2 are publicly available. One skilled in the art may readily reproduce the compositions and methods described herein by use of the sequences of the biomarkers, all of which are publicly available from conventional sources, such as GenBank.

The term "microarray" refers to an ordered arrangement of hybridizable array elements, e.g., primers, probes, ligands, on a substrate.

The term "ligand" refers to a molecule that binds to a protein or peptide, and includes antibodies and fragments thereof.

The term "polynucleotide," when used in singular or plural form, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide of less than 20 bases, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

As used herein, "labels" or "reporter molecules" are chemical or biochemical moieties useful for labeling a nucleic acid (including a single nucleotide), polynucleotide, oligonucleotide, or protein ligand, e.g., amino acid, peptide sequence, protein, or antibody. "Labels" and "reporter molecules" include fluorescent agents, chemiluminescent agents, chromogenic agents, quenching agents, radionucleotides, enzymes, substrates, cofactors, inhibitors, radioactive isotopes, magnetic particles, and other moieties known in the art. "Labels" or "reporter molecules" are capable of generating a measurable signal and may be covalently or noncovalently joined to an oligonucleotide or nucleotide (e.g., a non-natural nucleotide) or ligand.

It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" is used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

II. TARGET BIOMARKERS AND BIOMARKER SIGNATURES USEFUL IN THE METHODS AND COMPOSITIONS

The "targets" of the compositions and methods of these inventions include, in one aspect, the genes, gene fragments, transcripts and the expression products, including the proteins and peptide fragments thereof listed in FIG. 7 and Table 2. As described in the Examples below, the inventors identified 70 proteins (FIG. 7) that differed in expression by more than 2.5 fold between the conditions of EP and IUP. Further analysis resulted in the identification of highly significant protein biomarkers that could reliably distinguish between the conditions of EP and IUP (Table 2). In certain embodiments, superior diagnostic tests for distinguishing ectopic pregnancy from normal intrauterine pregnancy utilize at least one of the novel biomarkers, or one of the specifically identified isoforms or fragments of known markers. In other embodiments, superior diagnostic tests for distinguishing ectopic pregnancy from normal intrauterine pregnancy utilize at least two or more of the specific target biomarker protein forms identified herein. In still other embodiments, superior diagnostic tests for distinguishing ectopic pregnancy from normal intrauterine pregnancy will utilize at least nine or more of the specific target biomarker protein forms identified herein. In still other embodiments, at least 12 or more biomarkers will be employed in the methods and compositions described herein for diagnosis of EP.

In one embodiment a target of the methods and compositions described herein is ISM2, known as Isthmin2, thrombospondin, type I domain containing 3 isoform 1. The amino acid sequence for ISM2 is publicly available, see, e.g., GENBANK Accession No. AAI0120. Certain fragments of ISM2 that may be useful as targets in the methods and compositions described herein include one or more of the eight fragments identified in FIG. 6 as "modified peptide sequences". It should be understood that, depending upon the context, any reference to ISM2 herein also refers to any of these peptides, as well as the nucleotide sequences encoding ISM2 and/or any of these peptides.

In another embodiment a target of the methods and compositions described herein is ADAM12, i.e., the 909AA sequence appearing in FIG. 3B. The amino acid sequence for ADAM12 is publicly available, see, e.g., GENBANK Accession No. 043184.3. Specifically two proteolytically processed forms of the extracellular domain of ADAM12 were found to be shed into the patient's blood and are useful as targets. One of these targets is the pro-domain of ADAM12, which spans the sequence of FIG. 3B from aa30 to AA207. A second target is the extracellular domain of ADAM12 which spans the sequence of FIG. 3B from aa208 to aa708. Certain fragments of ADAM12 that may also be useful as targets include one or more of the 6 highlighted fragments in the pro domain of ADAM12 (identified by highlighting in FIG. 3B. In another embodiment, one or more of the 3 highlighted fragments in the EC domain of ADAM12 (FIG. 3B) are also useful as targets in the compositions and methods described herein. In still another embodiment, one or more of the fragments identified in FIG. 6 as "modified peptide sequences" are also useful as targets in the compositions and methods described herein. It should be understood that, depending upon the context, any reference to ADAM12 herein also refers to ADAM12pro, ADAM12EC, any of the peptides identified herein or in FIG. 6, as well as the nucleotide sequences encoding ADAM12 and/or any of these peptides.

In another embodiment a target of the methods and compositions described herein are specific isoforms of a family of related proteins produced by the placenta, called pregnancy specific beta-1 glycoprotein (PSG; also called serum specific protein-1 (SP1)). The inventors determined that certain isoforms not previously associated with EP can be used as biomarkers/targets in the methods and compositions described herein. Thus, in one embodiment a target for use herein is PSG, isoform 1 (PSG1). The amino acid sequence for PSG1 is publicly available, see, e.g., GENBANK Accession No. NP_001171754.1. In still another embodiment, one or more of the fragments identified in FIG. 6 as "modified peptide sequences" are also useful as targets in the compositions and methods described herein. It should be understood that, depending upon the context, any reference to PSG1 herein also refers to any of these peptides, as well as the nucleotide sequences encoding PSG1 and/or any of these peptides.

In another embodiment, a target for use herein is PSG, isoform 2 (PSG2). The amino acid sequence for PSG2 is publicly available, see, e.g., GENBANK Accession No. NP_112536.2. In still another embodiment, one or more of the fragments identified in FIG. 6 as "modified peptide sequences" are also useful as targets in the compositions and methods described herein. It should be understood that, depending upon the context, any reference to PSG2 herein also refers to any of these peptides, as well as the nucleotide sequences encoding PSG2 and/or any of these peptides.

In another embodiment a target for use herein is PSG, isoform 7 (PSG7). The amino acid sequence for PSG17 is publicly available, see, e.g., GENBANK Accession No. AAA75293. In still another embodiment, one or more of the fragments identified in FIG. 6 as "modified peptide sequences" are also useful as targets in the compositions and methods described herein. It should be understood that, depending upon the context, any reference to PSG7 herein also refers to any of these peptides, as well as the nucleotide sequences encoding PSG7 and/or any of these peptides.

In another embodiment a target for use herein is PSG, isoform 9 (PSG9). The amino acid sequence for PSG9 is publicly available, see, e.g., GENBANK Accession No. AAH05925.1. In still another embodiment, one or more of the fragments identified in FIG. 6 as "modified peptide sequences" are also useful as targets in the compositions and methods described herein. It should be understood that, depending upon the context, any reference to PSG9 herein also refers to any of these peptides, as well as the nucleotide sequences encoding PSG9 and/or any of these peptides.

In another embodiment a target for use herein is PSG, isoform 11 (PSG11). The amino acid sequence for PSG11 is publicly available, see, e.g., GENBANK Accession No. NP_002776. In still another embodiment, one or more of the fragments identified in FIG. 6 as "modified peptide sequences" are also useful as targets in the compositions and methods described herein. It should be understood that, depending upon the context, any reference to PSG11 herein also refers to any of these peptides, as well as the nucleotide sequences encoding PSG11 and/or any of these peptides.

In still other embodiments, the target for use in the methods and compositions described herein can include various combinations of these target biomarkers and/or fragments thereof.

In another embodiment a target combination, protein biomarker signature for use herein includes the known EP biomarker, choriogonadotropin subunit beta precursor (CGB) in combination with one or more of the above-noted targets. The amino acid sequence for CGB is publicly available, see, e.g., GENBANK Accession No. NP_000728.1. In another embodiment, one or more of the fragments identified in FIG. 6 as "modified peptide sequences" are also useful as targets in the compositions and methods described herein, optionally in combination with one or more of the above-noted targets. It should be understood that, depending upon the context, any reference to CGB herein also refers to any of these peptides, as well as the nucleotide sequences encoding CGB and/or any of these peptides.

In another embodiment a target combination, protein biomarker signature for use herein includes the known EP biomarker, glycoprotein hormone alpha chain precursor (CGA) in combination with one or more of the above-noted targets. The amino acid sequence for CGA is publicly available, see, e.g., GENBANK Accession No. P01241.2. In another embodiment, one or more of the fragments identified in FIG. 6 as "modified peptide sequences" are also useful as targets in the compositions and methods described herein, optionally in combination with one or more of the above-noted targets. It should be understood that, depending upon the context, any reference to CGA herein also refers to any of these peptides, as well as the nucleotide sequences encoding CGA and/or any of these peptides.

In another embodiment a target combination, protein biomarker signature for use herein includes the known EP biomarker, pappalysin-1 precursor (PAPPA) in combination with one or more of the above-noted targets. The amino acid sequence for PAPPA is publicly available, see, e.g., GENBANK Accession No. Q13219.3. In another embodiment, one or more of the fragments identified in FIG. 6 as "modified peptide sequences" are also useful as targets in the compositions and methods described herein, optionally in combination with one or more of the above-noted targets. It should be understood that, depending upon the context, any reference to PAPPA herein also refers to any of these peptides, as well as the nucleotide sequences encoding PAPPA and/or any of these peptides.

In another embodiment a target combination, protein biomarker signature for use herein includes the known EP biomarker, chorionic somatomammotropin hormone precursor (CSH1) in combination with one or more of the above-noted targets. The amino acid sequence for CSH1 is publicly available, see, e.g., GENBANK Accession No. P01241.2. In another embodiment, one or more of the fragments identified in FIG. 6 as "modified peptide sequences" are also useful as targets in the compositions and methods described herein, optionally in combination with one or more of the above-noted targets. It should be understood that, depending upon the context, any reference to CSH1 herein also refers to any of these peptides, as well as the nucleotide sequences encoding CSH1 and/or any of these peptides.

In another embodiment a target combination, protein biomarker signature for use herein includes the known EP biomarker, progestagen-associated endometrial protein (PAEP), in combination with one or more of the above-noted targets. The amino acid sequence for PAEP is publicly available, see, e.g., GENBANK Accession No. AAI13729.1. In another embodiment, one or more of the fragments identified in FIG. 6 as "modified peptide sequences" are also useful as targets in the compositions and methods described herein, optionally in combination with one or more of the above-noted targets. It should be understood that, depending upon the context, any reference to PAEP herein also refers to any of these peptides, as well as the nucleotide sequences encoding PAEP and/or any of these peptides.

In yet a further embodiment, a variety of target biomarker signatures for EP include any combination of the EP biomarkers identified in Table 2 (including fragments of FIG. 6), which further include one or more of the biomarkers identified in FIG. 7 other than those already identified above, including fragments of FIG. 10 of U.S. Provisional Patent Application No. 61/443,026.

Among desirable biomarker signatures are signatures at least two biomarkers, at least 5 biomarkers or all seven biomarkers selected from ISM2, the pro-domain or extracellular (EC) domain of ADAM12, pregnancy specific beta-1 glycoprotein isoform 1 (PSG1), pregnancy specific beta-1 glycoprotein isoform 7 (PSG7), pregnancy specific beta-1 glycoprotein isoform 11 (PSG11), pregnancy specific beta-1 glycoprotein isoform 9 (PSG9), and pregnancy specific beta-1 glycoprotein isoform 2 (PSG2). Other suitable biomarker signatures include combinations of at least one of the above noted 7 biomarkers with at least one of the following biomarkers: CGB, CBA, PAPPA, CSH1 and PAEP. Still another embodiment of a biomarker signature contains all 12 of the above-recited biomarkers. In another embodiment, a biomarker signature contains at least one, at least 5, at least 10, at least 15, at least 25, at least 30 or more additional biomarker from those identified in FIG. 7.

III. DIAGNOSTIC REAGENTS AND KITS

A. Labeled or Immobilized Biomarkers or Peptides

In one embodiment, diagnostic reagents for use in the methods of diagnosing EP includes one target biomarker identified in FIG. 7 or Table 2 herein, associated with a detectable label or portion of a detectable label system. In another embodiment, a diagnostic reagent includes one target biomarker identified in FIG. 7 or Table 2 herein, immobilized on a substrate. In still another embodiment, combinations of such labeled or immobilized biomarkers are suitable reagents and components of a diagnostic kit. Among such immobilized or labeled biomarkers are those selected from the biomarkers:
  i. Isthmin2 (ISM2),
  ii. the pro-domain or extracellular (EC) domain of ADAM12,
  iii. pregnancy specific beta-1 glycoprotein isoform 1 (PSG1),
  iv. pregnancy specific beta-1 glycoprotein isoform 7 (PSG7),
  v. pregnancy specific beta-1 glycoprotein isoform 11 (PSG11),
  vi. pregnancy specific beta-1 glycoprotein isoform 9 (PSG9),
  vii. pregnancy specific beta-1 glycoprotein isoform 2 (PSG2),
  viii. choriogonadotropin subunit beta precursor (CGB);
  ix. glycoprotein hormones alpha chain precursor (CGA);
  x. pappalysin-1 precursor (PAPPA);
  xi. chorionic somatomammotropin hormone precursor (CSH1); and
  xii. progestagen-associated endometrial protein (PAEP).

In another aspect, suitable embodiments of such labeled or immobilized reagents include at least one, 2, 3, 4, 5, 6, 7 or all 8 of biomarkers (i) to (viii) or their unique peptide fragments therein (see FIG. 6). In another aspect, other suitable embodiments of such labeled or immobilized reagents include an additional at least one, 2, 3, or 4 of biomarkers (ix) through (xii) or their unique peptide fragments therein (see FIG. 6).

Still other diagnostic reagents are the surrogate peptides used for the MRM assays as disclosed in FIGS. 6 and 10, as well as additional peptides from the selected biomarker proteins, domains or isoforms of FIG. 7 and Table 2.

Any combination of labeled or immobilized biomarkers can be assembled in a diagnostic kit for the purposes of diagnosing EP. For example, one embodiment of a diagnostic kit includes labeled or immobilized reagents (i) through (v). Another embodiment of a diagnostic kit includes labeled or immobilized reagents (i) through (viii). Still another embodiment of a diagnostic kit includes labeled or immobilized reagents (i) through (xii). Still other components of the biomarker signatures, associated with detectable labels or immobilized on substrates provide additional diagnostic kits. Still other components of the biomarker signatures are labeled or immobilized biomarkers or fragments thereof as listed on FIG. 7.

For these reagents, the labels may be selected from among many known diagnostic labels, including those described above. Similarly, the substrates for immobilization may be any of the common substrates, glass, plastic, a microarray, a microfluidics card, a chip or a chamber.

B. Labeled or Immobilized Ligands that Bind the Biomarkers or Peptides

In another embodiment, the diagnostic reagent is a ligand that binds to a biomarker of any one or more of (i) to (viii) or a unique peptide thereof, as indicated in FIG. 6. Such a ligand desirably binds to a protein biomarker or a unique peptide contained therein, and can be an antibody which specifically binds a single biomarker from (i) to (viii), or a unique peptide in that single biomarker. Various forms of antibody, e.g., polyclonal, monoclonal, recombinant, chimeric, as well as fragments and components (e.g., CDRs, single chain variable regions, etc.) may be used in place of antibodies. The ligand itself may be labeled or immobilized.

In another aspect, suitable embodiments of such labeled or immobilized reagents include at least one, 2, 3, 4, 5, 6, 7 or 8 ligands. Each ligand binds to a single biomarker (i) to (viii) or their unique peptide fragments therein (see FIG. 6). In another aspect, other suitable embodiments of such labeled or immobilized reagents include an additional at least one, 2, 3, 4 or 5 ligands, wherein each ligand binds to a single biomarker (ix) through (xii) or their unique peptide fragments therein (see FIG. 6).

Any combination of labeled or immobilized biomarker-binding ligands can be assembled in a diagnostic kit for the purposes of diagnosing EP. For example, one embodiment of a diagnostic kit includes labeled or immobilized reagents that bind to biomarkers (i) through (v). Another embodiment of a diagnostic kit includes labeled or immobilized reagents that bind to biomarkers (i) through (viii). Still another embodiment of a diagnostic kit includes labeled or immobilized reagents that bind to biomarkers (i) through (xii). Still other components of the many biomarker signatures that may be formed by various combinations of ligand to the biomarkers (i) through (xiii), or their unique fragments (FIG. 6) associated with detectable labels or immobilized on substrates provide additional diagnostic kits. Still other components include ligands to biomarkers or fragments thereof as listed on FIG. 7.

C. Labeled or Immobilized Polynucleotide/Oligonucleotides that Hybridize to Genes, Gene Fragments, Gene Transcripts of Other Sequences Encoding the Biomarkers or Peptides In another embodiment, the diagnostic reagent is a polynucleotide or oligonucleotide sequence that hybridizes to gene, gene fragment, gene transcript or nucleotide sequence encoding a biomarker of any one or more of (i) to (vii) or encoding a unique peptide thereof, as indicated in FIG. 6. Such a polynucleotide/oligonucleotide can be a probe or primer, and may itself be labeled or immobilized. In another aspect, suitable embodiments of such labeled or immobilized reagents include at least one, 2, 3, 4, 5, 6, 7 or 8 polynucleotide/oligonucleotide. Each polynucleotide/oligonucleotide hybridizes to a gene, gene fragment, gene transcript or expression product encoding a single biomarker (i) to (viii) or their unique peptide fragments therein (see FIG. 6). In another aspect, other suitable embodiments of such labeled or immobilized reagents include an additional at least one, 2, 3, 4 or 5 polynucleotide/oligonucleotides, wherein each sequence hybridizes to a gene, gene fragment, gene transcript of expression product encoding a single biomarker (ix) through (xii) or their unique peptide fragments therein (see FIG. 6).

Any combination of labeled or immobilized biomarker-hybridizable sequences can be assembled in a diagnostic kit for the purposes of diagnosing EP. For example, one embodiment of a diagnostic kit includes labeled or immobilized reagents that hybridize to biomarkers (i) through (v). Another embodiment of a diagnostic kit includes labeled or immobilized reagents that hybridize to biomarkers (i) through (vii). Still another embodiment of a diagnostic kit includes labeled or immobilized reagents that hybridize to biomarkers (i) through (xii). Still other components of the many biomarker signatures that may be formed by various combinations of polynucleotide/oligonucleotide sequences that hybridize to the biomarkers (i) through (xii), or their unique fragments (FIG. 6) associated with detectable labels or immobilized on substrates provide additional diagnostic kits. Still other components include similar reagents that hybridize to biomarkers or fragments thereof as listed on FIG. 7. In one embodiment, these polynucleotide or oligonucleotide reagent(s) are part of a primer-probe set, and the kit comprises both primer and probe. Each said primer-probe set amplifies a different gene, gene fragment or gene expression product that encodes a different biomarker of any combination of (i) through (viii), optionally including one or more additional biomarkers (ix) through (xii). In still another embodiment, additional polynucleotide or oligonucleotide sequences in the diagnostic reagent or kit, hybridize to a gene, gene fragment, gene transcript or expression product identified in FIG. 7.

For use in the compositions the PCR primers and probes are preferably designed based upon intron sequences present in the biomarker gene(s) to be amplified selected from the gene expression profile. The design of the primer and probe sequences is within the skill of the art once the particular gene target is selected. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publicly available tools such as DNA BLAST software, the Repeat Masker program (Baylor College of Medicine), Primer Express (Applied Biosystems); MGB assay-by-design (Applied Biosystems); Primer3 (Steve Rozen and Helen J. Skaletsky (2000) Primer3 on the WWW for general users and for biologist programmers and other publications.

In general, optimal PCR primers and probes used in the compositions described herein are generally 17-30 bases in length, and contain about 20-80%, such as, for example, about 50-60% G+C bases. Melting temperatures of between 50 and 80° C., e.g. about 50 to 70° C. are typically preferred.

Thus, a composition for diagnosing ectopic pregnancy in a mammalian subject as described herein can be a kit containing multiple reagents or one or more individual reagents. For example, one embodiment of a composition includes a substrate upon which the biomarkers, polynucleotides or oligonucleotides, or ligands are immobilized. In another embodiment, the composition is a kit also contains optional detectable labels, immobilization substrates, optional substrates for enzymatic labels, as well as other laboratory items.

The compositions based on the biomarkers selected from Tables 2 or FIG. 7 described herein, optionally associated with detectable labels, can be presented in the format of a microfluidics card, a chip or chamber, or a kit adapted for use with the assays described in the Examples, ELISAs or PCR, RT-PCR or Q PCR techniques described herein.

The selection of the ligands, poly/oligonucleotide sequences, their length, suitable labels and substrates used in the composition are routine determinations made by one of skill in the art in view of the teachings of which biomarkers form signature suitable for the diagnosis of ectopic pregnancy.

IV. METHODS FOR DIAGNOSING EP

A. Protein Assays

In one embodiment, a method for diagnosing an ectopic pregnancy in a female mammalian subject includes measuring in a biological fluid sample of the subject the expression level of a protein or peptide fragment thereof selected from at least one biomarker of (i) to (viii). Alternatively, the method includes measuring a combination of two or more biomarkers (i) through (viii). The method further involves comparing the subject's expression level of the selected biomarker or biomarker fragment with the level of the same protein or peptide in the biological fluid of a reference or control female mammalian subject having a normal intrauterine pregnancy (IUP). Changes in expression of the subject's selected biomarker protein or peptide fragment from those of the reference or control correlates with a diagnosis of ectopic pregnancy.

In another embodiment, the above method further includes measuring in the biological fluid sample of the subject the expression level of an additional biomarker protein or peptide fragment of (ix) to (xii). In another embodiment, the above method further includes measuring in the biological fluid sample of the subject the expression level of two or more additional biomarker protein or peptide fragments of (ix) to (xii).

In another embodiment, the above method further includes measuring in the biological fluid sample of the subject the expression level of an additional biomarker protein or peptide fragment of a biomarker identified in FIG. 7, which is other than (i) through (xii).

In this diagnostic method, a change in expression level of one or more of the selected biomarker proteins or peptide fragment in comparison to the IUP control reference may be an increase or decrease in the expression levels of the individual biomarkers. This method may employ any of the suitable diagnostic reagents or kits or compositions described above.

The measurement of the EP biomarkers in the biological sample may employ any suitable ligand, e.g., antibody (or antibody to any second biomarker) to detect the EP biomarker protein. Such antibodies may be presently extant in the art or presently used commercially, such as those available as part of commercial antibody ELISA assay kits or that may be developed by techniques now common in the field of immunology. As used herein, the term "antibody" refers to an intact immunoglobulin having two light and two heavy chains or any fragments thereof. Thus a single isolated antibody or fragment may be a polyclonal antibody, a high affinity polyclonal antibody, a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, a single chain Fv construct, a Fab construct, a light chain variable or complementarity determining region (CDR) sequence, etc. A recombinant molecule bearing the binding portion of an EP biomarker antibody, e.g., carrying one or more variable chain CDR sequences that bind e.g., ISM2, may also be used in a diagnostic assay. As used herein, the term "antibody" may also refer, where appropriate, to a mixture of different antibodies or antibody fragments that bind to the selected biomarker. Such different antibodies may bind to different biomarkers or different portions of the same EP biomarker protein than the other antibodies in the mixture. Such differences in antibodies used in the assay may be reflected in the CDR sequences of the variable regions of the antibodies. Such differences may also be generated by the antibody backbone, for example, if the antibody itself is a non-human antibody containing a human CDR sequence, or a chimeric antibody or some other recombinant antibody fragment containing sequences from a non-human source. Antibodies or fragments useful in the method of this invention may be generated synthetically or recombinantly, using conventional techniques or may be isolated and purified from plasma or further manipulated to increase the binding affinity thereof. It should be understood that any antibody, antibody fragment, or mixture thereof that binds one of the biomarkers (i) through (xii) or a particular sequence of the selected EP biomarker as defined in FIG. 6 or 10 may be employed in the methods of the present invention, regardless of how the antibody or mixture of antibodies was generated.

Similarly, the antibodies may be tagged or labeled with reagents capable of providing a detectable signal, depending upon the assay format employed. Such labels are capable, alone or in concert with other compositions or compounds, of providing a detectable signal. Where more than one antibody is employed in a diagnostic method, e.g., such as in a sandwich ELISA, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength.

Other label systems that may be utilized in the methods of this invention are detectable by other means, e.g., colored latex microparticles (Bangs Laboratories, Indiana) in which a dye is embedded may be used in place of enzymes to provide a visual signal indicative of the presence of the resulting selected biomarker-antibody complex in applicable assays. Still other labels include fluorescent compounds, radioactive compounds or elements. Preferably, an anti-biomarker antibody is associated with, or conjugated to a fluorescent detectable fluorochromes, e.g., fluorescein isothiocyanate (FITC), phycoerythrin (PE), allophycocyanin (APC), coriphosphine-O(CPO) or tandem dyes, PE-cyanin-5 (PC5), and PE-Texas Red (ECD). Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and Alexa dyes. Combinations of such labels, such as Texas Red and rhodamine, FITC+PE, FITC+PECy5 and PE+PECy7, among others may be used depending upon assay method.

Detectable labels for attachment to antibodies useful in diagnostic assays of this invention may be easily selected from among numerous compositions known and readily available to one skilled in the art of diagnostic assays. The EP biomarker-antibodies or fragments useful in this invention are not limited by the particular detectable label or label system employed. Thus, selection and/or generation of suitable EP biomarker antibodies with optional labels for use in this invention is within the skill of the art, provided with this specification, the documents incorporated herein, and the conventional teachings of immunology.

Similarly the particular assay format used to measure the selected EP biomarker in a biological sample may be selected from among a wide range of immunoassays, such as enzyme-linked immunoassays, such as those described in the examples below, sandwich immunoassays, homogeneous assays, immunohistochemistry formats, or other conventional assay formats. One of skill in the art may readily select from any number of conventional immunoassay formats to perform this invention.

Other reagents for the detection of protein in biological samples, such as peptide mimetics, synthetic chemical compounds capable of detecting the selected EP biomarker may be used in other assay formats for the quantitative detection of biomarker protein in biological samples, such as high pressure liquid chromatography (HPLC), immunohistochemistry, etc.

Employing ligand binding to the biomarker proteins or multiple biomarkers forming the signature enables more precise quantitative assays, as illustrated by the multiple reaction monitoring (MRM) mass spectrometry (MS) assays. As an alternative to specific peptide-based MRM-MS assays that can distinguish specific protein isoforms and proteolytic fragments, the knowledge of specific molecular forms of biomarkers allows more accurate antibody-based assays, such as sandwich ELISA assays or their equivalent. Frequently, the isoform specificity and the protein domain specificity of immune reagents used in pre-clinical (and some clinical) diagnostic tests are not well defined. MRM-MS assays were used to quantitative the levels of ADAM12 in the individual patient serum samples (see FIG. 5) used to comprise the serum pools used for discovery.

In one embodiment, suitable assays for use in these methods include immunoassays using antibodies or ligands to the above-identified biomarkers and biomarker signatures. In another embodiment, a suitable assay includes a multiplexed MRM based assays for two more EP biomarkers that include one or more of the proteins/unique peptides in Table 2 and FIG. 6. It is anticipated that ultimately the platform most likely to be used in clinical assays will be multi-plexed or parallel sandwich ELISA assays or their equivalent, primarily because this platform is the technology most commonly used to quantify blood proteins in clinical laboratories. However, MRM MS assays may continue to fill an important niche as they can be used productively to help evaluate the isoform/molecular form specificity of any existing immunoassays or those developed in the future.

B. Nucleic Acid Assays

Still other methods useful in performing the diagnostic steps described herein are known in the art. Such methods include methods based on hybridization analysis of polynucleotides, methods based on sequencing of polynucleotides, proteomics-based methods or immunochemistry techniques. The most commonly used methods known in the art for the quantification of mRNA expression in a sample include northern blotting and in situ hybridization; RNAse protection assays; and PCR-based methods, such as reverse transcription polymerase chain reaction (RT-PCR) or qPCR. Alternatively, antibodies may be employed that can recognize specific DNA-protein duplexes. The methods described herein are not limited by the particular techniques selected to perform them. Exemplary commercial products for generation of reagents or performance of assays include TRI-REAGENT, Qiagen RNeasy mini-columns, MASTER-PURE Complete DNA and RNA Purification Kit (EPICENTRE®, Madison, Wis.), Paraffin Block RNA Isolation Kit (Ambion, Inc.) and RNA Stat-60 (Tel-Test), the MassARRAY-based method (Sequenom, Inc., San Diego, Calif.), differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) and high coverage expression profiling (HiCEP) analysis.

Thus, in yet another embodiment, a method for diagnosing an ectopic pregnancy in a female mammalian subject involves measuring in a biological fluid sample of the subject the expression level of a gene, gene fragment, gene transcript or expression product encoding one or more of the biomarkers (i) to (viii). Alternatively, the method includes measuring the expression level of a gene, gene fragment, gene transcript or expression product encoding a combination of two or more biomarkers (i) through (viii). The method further includes comparing the subject's selected biomarker gene, gene fragment, gene transcript or expression product expression level with the level of the same gene, gene fragment, gene transcript or expression product in the biological fluid of a reference or control female mammalian subject having a normal intrauterine pregnancy (IUP). Changes in expression of the subject's selected biomarker gene, gene fragment, gene transcript or expression products from those of the reference or control correlates with a diagnosis of ectopic pregnancy.

In another embodiment, the above method further includes measuring in the biological fluid sample of the subject the expression level of an additional biomarker gene, gene fragment, gene transcript or expression product encoding fragment of biomarker (ix) to (xii). In another embodiment, the above method further includes measuring in the biological fluid sample of the subject the expression level of two or more additional biomarker gene, gene fragment, gene transcript or expression product encoding biomarkers (ix) to (xii).

In another embodiment, the above method further includes measuring in the biological fluid sample of the subject the expression level of an additional biomarker gene, gene fragment, gene transcript or expression product encoding fragment of a biomarker identified in FIG. 7, which is other than (i) through (xii).

In this diagnostic method, a change in expression level of one or more of the selected biomarker gene, gene fragment, gene transcript or expression product in comparison to the IUP control reference may be an upregulation or down regulation in the expression of the individual biomarkers gene, gene fragment, transcript or expression product. This method may employ any of the suitable diagnostic reagents or kits or compositions described above In yet another embodiment, the methods and compositions described herein may be used in conjunction with clinical risk factors to help physicians make more accurate decisions about how to manage patients with ectopic pregnancies. Another advantage of these methods and compositions is that diagnosis may occur early.

V. EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Ectopic pregnancy (EP) and normal intrauterine pregnancy (IUP) serum proteomes were quantitatively compared to systematically identify candidate biomarkers. A 3-D biomarker discovery strategy consisting of abundant protein immunodepletion, SDS gels, LC-MS/MS, and label-free quantitation of MS signal intensities identified 70 candidate biomarkers with differences between groups greater than 2.5-fold. Further statistical analyses of peptide quantities were used to select the most promising 12 biomarkers for further study, which included known EP biomarkers, novel EP biomarkers (ADAM12 and ISM2), and five specific isoforms of the pregnancy specific beta-1-glycoprotein family. Technical replicates showed good reproducibility and protein intensities from the label-free discovery analysis compared favorably with reported abundance levels of several known reference serum proteins over at least three orders of magnitude. Similarly, relative abundances of candidate biomarkers from the label-free discovery analysis were consistent with relative abundances from pilot validation assays performed for certain biomarkers using label-free multiple reaction monitoring of both the patient serum pools used for discovery and the individual samples that constituted these pools.

As described in the Examples below, the independent MRM-MS quantitative method used specific peptides as surrogates for the proteins that were identified as candidate biomarkers. These verification studies were performed in the individual patient samples that made up the pools for the discovery phase, so they are not an independent dataset. Biomarkers that did not show a significant difference between EP and IUP in the initial validation study cannot necessarily be discounted due to the small number of samples used. The 12 proteins listed in Table 2 are further tested in an independent patient cohort using the multiplexed MRM-MS quantitative assay used to measure these protein biomarkers in the original patient serum samples.

Example 1

Systematic Discovery of Ectopic Pregnancy Serum Biomarkers Using 3-D Protein Profiling Coupled with Label-Free Quantitation We used a 3-D method to systematically compare sera from patients with EP and IUP to identify candidate EP biomarkers. The 3-D method consisted of immunodepletion of 20 abundant serum proteins followed by GeLC-MS/MS analysis, with subsequent label-free quantitative comparisons using Rosetta Elucidator software (v3.1, Rosetta Biosoftware, Seattle, Wash.) to align and compare data at the MS ion intensity level. This software is no longer commercially developed as a result of the purchase of Rosetta Biosoftware by Microsoft Corporation.

This analysis identified 70 candidate biomarkers with greater than 2.5-fold difference between the EP and IUP groups, and a high-priority biomarker subset was selected based upon the statistical probability that annotated peptides could properly classify samples into the EP or IUP group. Pilot validation of several biomarkers was conducted using label-free multiple reaction monitoring (MRM) to analyze the individual samples that constituted the pools used for the initial discovery experiments. The results demonstrate that both label-free methods were reproducible and yielded consistent relative abundance changes, which resulted in identification of novel EP biomarkers as well as specific isoforms of a previously reported EP-related protein family.

A. Reagents.

200 proof molecular biology grade ethanol, LC-MS grade formic acid, and iodoacetamide were purchased from Sigma-Aldrich (St. Louis, Mo.). Sodium dodecyl sulfate (SDS) and Tris were purchased from Bio-Rad (Hercules, Calif.). Dithiothreitol (DTT) was obtained from GE Healthcare (Piscataway, N.J.). HPLC grade acetonitrile was purchased from Thomas Scientific (Swedesboro, N.J.). Sequencing grade modified trypsin was purchased from Promega (Madison, Wis.).

B. Serum Collection.

Serum was collected from nine patients with an ectopic pregnancy and nine matched controls with normal intrauterine pregnancies. Specimens were matched based on gestational age (range of 4 weeks, 2 days to 11 weeks, 3 days), hCG level (3821-52430 mIU/ml) and diagnosis (EP or IUP). Blood was collected by venipuncture into BD Vacutainer red/grey serum separator tubes (BD, Franklin Lakes, N.J.), allowed to clot at RT, and centrifuged. Serum was then aliquoted, frozen, and stored at −80° C.

C. ProteoPrep20 Depletion.

Samples were depleted of 20 abundant serum proteins using a ProteoPrep20 Immunodepletion Column (Sigma-Aldrich). Typically, 100 µL of serum was filtered through a 0.22 µm microcentrifuge filter and injected onto the column. The flow-through fractions containing unbound proteins were collected, pooled, and precipitated with nine volumes of 200 proof ethanol, pre-chilled to −20° C. Ethanol supernatants were carefully removed and protein pellets were frozen and stored at −20° C. until further use. Fractions containing affinity-bound abundant proteins were collected and pooled, neutralized with 1M NaOH, and frozen for possible future analysis.

D. SDS-PAGE/In-Gel Trypsin Digestion.

Prior to 1-D SDS-PAGE, frozen protein pellets from ethanol precipitation of depleted serum were thawed briefly and re-suspended in 50 mM Tris-Cl, 1% SDS, pH 8.5. Samples were reduced with 20 mM DTT for 1 h at 37° C. and alkylated with 60 mM IAM in 50 mM Tris-Cl, pH 8.5 for 1 h at 37° C. Alkylation was quenched with 50 mM DTT for 15 min at 37° C. Following in-solution reduction and alkylation, samples were prepared for PAGE by addition of SDS sample buffer. For each sample, aliquots representing 10 µL of original serum per lane were loaded into 10-well 12% NuPAGE mini-gels (Invitrogen, Carlsbad, Calif.) and separated using MES running buffer until the tracking dye had migrated 2 cm. Gels were stained with Colloidal Blue (Invitrogen), and each lane was subsequently sliced into 21 uniform 1 mm slices using a custom razor-blade array. Corresponding slices from three lanes for each depleted serum sample were combined in single wells of a 96-well pierced plate (Biomachines, Inc., Carrboro, N.C.). Gel slices were digested overnight using 0.02 µg/µL modified trypsin. Following digestion, aliquots of corresponding fractions from three patients in each group were pooled to produce three EP and three IUP serum fraction pools. These pools and the remainder of individual sample digests were frozen and stored at −20° C. for future discovery and validation analyses, respectively.

E. LC-MS/MS.

For initial discovery of candidate biomarkers, pooled tryptic digests were analyzed in duplicate using an LTQ-Orbitrap XL mass spectrometer (Thermo Scientific, Waltham, Mass.) interfaced with a Nano-ACQUITY UPLC system (Waters, Milford, Mass.) with the column heater maintained at 40° C. For each tryptic digest, 6 µL was injected onto a UPLC Symmetry trap column (180 µm i.d.×2 cm packed with 5 µm C18 resin; Waters), and tryptic peptides were separated by RP-HPLC on a BEH C18 nanocapillary analytical column (75 µm i.d.×25 cm, 1.7 µm particle size; Waters). Solvent A was Milli-Q (Millipore, Billerica, Mass.) water containing 0.1% formic acid, and Solvent B was ACN containing 0.1% formic acid. Peptides were eluted at 200 mL/min using an ACN gradient consisting of 5-28% B over 42 min, 28-50% B over 25.5 min, 50-80% B over 5 min, 80% B for 4.5 min before returning to 5% B over 0.5 min. The column was re-equilibrated using 5% B at 400 nl/min for 20 min before injecting the next sample. The mass spectrometer was set to scan m/z from 400 to 2000. The full MS scan was collected at 60,000 resolution in the Orbitrap in profile mode followed by data-dependant MS/MS scans on the three most abundant ions exceeding a minimum threshold of 1000, collected in the linear trap. Monoisotopic precursor selection was enabled and charge-state screening was enabled to reject z=1 ions. Ions subjected to MS/MS were excluded from repeated analysis for 60 s. The order of sample analysis was randomized to prevent temporal experimental bias. Mass spectrometer, HPLC, and autoinjector performance were rigorously monitored to maintain mass accuracies within 2 ppm, retention times within a ±1.0 min window, and injection volumes within ±10% to facilitate label-free pattern comparisons.

F. Label-Free Quantitation Using the Rosetta Elucidator System.

LC-MS and LC-MS/MS data were analyzed using the Rosetta Elucidator system. A total of 252 raw MS spectra files were imported into the system (6 depleted serum pools×21 fractions×duplicates); LC-MS data were acquired from 0-98 min, but based on elution profiles of peptides and density of ion signals, data for the label-free comparison was trimmed to 20-75 minutes and the m/z range was trimmed to 400-1800. Retention time (RT) alignment, feature identification (discrete ion signals), and feature extraction across the entire chromatographic time window were performed by the Elucidator software, essentially as described by others.[29,30] DTAs were created with BioWorks v. 3.3.1 (Thermo Scientific) using high-quality features with z>1 and <5, and having peak scores greater than 0.7 and 0.8 for RT and m/z, respectively. Peak scores, as defined in the Rosetta Elucidator System User Guide, are correlation coefficients that compare the shape of a feature in the time and m/z dimensions to the shape of an ideal peak, with an ideal peak having a score of 1.[31] DTAs were searched using the SEQUEST algorithm (v. 28, rev. 13, University of Washington, Seattle, Wash.) with a full tryptic constraint against a human Uni-Ref100 protein sequence database (Oct. 23, 2007, 84,662 entries) to which commonly observed "contaminants" were added (trypsin, keratins, etc.). A decoy database was produced by reversing the protein sequence of each database entry and the entire reversed database was appended in front of the forward database. Peptide and protein information was assigned to features using the Protein and Peptide Tellers, which are Rosetta Biosoftware's re-implementations of the open-source ProteinProphet™ and PeptideProphet® programs,[32,33] respectively. Specifically, as described in the Rosetta Elucidator System User Guide, Peptide Teller validates peptides assigned to MS/MS spectra by search engines by computing probabilities that search results are correct in the dataset based on search scores and peptide properties. Protein Teller computes probabilities that proteins were present in a sample based on the combined probabilities of their corresponding peptides. Importantly, it deals with two issues critical for protein inference: First, correct peptides often correspond to multi-hit proteins whereas incorrect peptides most often correspond to single-hit proteins. This non-random grouping of peptides with their corresponding proteins can lead to an amplification of the false positive error rate at the protein level. Protein Teller counteracts this effect by penalizing peptides corresponding to single-hit proteins at an appropriate amount learned from each data set. Second, a substantial number of identified peptides are common to multiple database entries. This is especially true for human and other higher eukaryotic species, which usually contain alternative splice forms, large, homologous protein families, and partial sequences in the databases. Protein Teller apportions common peptides among all corresponding proteins to derive the simplest list of proteins that can explain the observed peptides.[31] Data were filtered using Protein Teller scores of correct identification probability>0.95 and Peptide Teller scores>0.8.

G. Identification of Differentially Expressed Proteins of Interest.

The experiment was defined in the Elucidator System as having two treatment groups (EP, IUP). Each treatment group included three pools of three individual serum samples and two technical replicates per group. Several strategies and tools within the Elucidator System were used to analyze the data, including differences at the annotated peptide level, the protein level, and peptide trend plots. Specifically, the 2-D visual script (not shown) utilized peptide annotation to sum feature intensities across gel slice fractions within each sample, and peptides significantly different between groups were defined using a two-way Analysis of Variance (ANOVA) with p<0.001. Peptides were grouped into consensus proteins using Protein Teller and protein level ratios were determined using those peptides that were significantly different between groups, as defined by ANOVA.

A subsequent independent manual analysis was conducted by exporting the peptide report results, which included values for technical replicates, into Microsoft Excel (Microsoft Corporation, Redmond, Wash.). Peptides were grouped into proteins based on protein description and pair-wise ratios between average intensities of IUP and EP were calculated for each peptide as well as the summed intensity for the protein. In addition, a further statistical test was developed independently to identify those peptides with the greatest discrimination power between groups, as summarized below.

H. Identification of the Most Significant Peptide Differences.

We assumed peptide logarithmic expression levels in each sample were normally distributed and introduced two statistical measurements, sum-of-Z-score (sumZscores) and probability-of-misclassification ($P_m$), to objectively quantitate the separation between the two distributions. Given two normal distributions with means and variances ($\mu_1$, $\sigma_1^2$) and ($\mu_2$, $\sigma_2^2$) respectively, sumZscores computes the distance between the two means in terms of Z-scores, taking into account the widths of the distributions. Explicitly, we have the following expression for sumZscores, $$sumZscore = \frac{|\mu_1 - \mu_2|}{\sigma_1} + \frac{|\mu_1 - \mu_2|}{\sigma_2} = |\mu_1 - \mu_2|\left(\frac{1}{\sigma_1} + \frac{1}{\sigma_2}\right)$$

On the other hand, the probability-of-misclassification ($P_m$) of a peptide represents the minimal theoretical error that would occur if we were to classify samples from a balanced mixture of two normal distributions into EP or IUP group by thresholding on the logarithmic expression level of that peptide. In practice, the optimal threshold value can be found by solving a quadratic equation for the point(s) where the two normal distributions yield equal density, and then select the one with lower classification error. The value for $P_m$ is then computed as the corresponding minimal theoretical error. A detailed derivatization of is described in Supporting Information.

I. Targeted LC-MS/MS Analysis.

Targeted LC-MS/MS analyses for proteins of interest were performed on a LTQ-Orbitrap XL mass spectrometer coupled to a Nano-ACQUITY UPLC system. Targeted analysis was used to: verify the initial peptide and protein identifications of putative biomarkers of interest, distinguish between related protein isoforms where needed, and increase the number of identified peptides where needed for subsequent quantitative assay development. Columns, solvents, and gradient used were as described above for LC-MS/MS. A list of m/z values representing the targeted peptides were generated and placed into the parent mass list of the MS method. The mass spectrometer was set to scan m/z from 360 to 2000 at 60,000 resolution in the Orbitrap followed by data-dependent ion trap MS/MS scans of up to the three most abundant ions from the parent mass list that exceed a minimum threshold of 500. Targeted ions were monitored throughout the entire run with an m/z tolerance of ±10 ppm. Dynamic exclusion was enabled with a repeat count of 2, repeat duration of 10 s, and exclusion duration of 10 s. Monoisotopic precursor selection was not enabled, and charge-state screening was set to reject singly charged ions and ions with unknown charge state.

J. Label-Free Multiple Reaction Monitoring (MRM).

MRM experiments were performed on a 4000 Q TRAP hybrid triple quadrupole/linear ion trap mass spectrometer (Applied Biosystems, Foster City, Calif.) interfaced with a NanoACQUITY UPLC system. Chromatography was performed with Solvent A (Milli-Q water with 0.1% formic acid) and Solvent B (acetonitrile with 0.1% formic acid). Typically, 5 µA of an appropriate tryptic digest was injected in duplicate on PicoFrit columns (75-µm i.d., 15-µm tip opening; New Objective, Woburn, Mass.) packed in house with 25 cm of Magic C18 reversed-phase resin (Michrom Bioresources, Auburn, Calif.). Peptides were eluted at 300 mL/min using an acetonitrile gradient consisting of 5-35% B over 15 min, 35-70% B over 5 min, 70% B for 5 min before returning to 5% B in 0.5 min. To minimize sample carryover, a blank was run between each sample. Data were acquired with a spray voltage of 2,800 V, curtain gas of 20 p.s.i., nebulizer gas of 10 p.s.i., and an interface heater temperature of 150° C. At least three MRM transitions per peptide, and three peptides per protein were monitored and acquired at unit resolution in both Q1 and Q3 quadrupoles to maximize specificity. Scheduled MRM also was used to reduce the number of concurrent transitions and maximize the dwell time for each transition. The MRM detection window was set at 4 min, and target scan time was set at 1 s. The final MRM method included 60 optimized transitions for five target proteins. Data analysis was performed using Multi-Quant version 1.1 software (AB/MDS Sciex, Foster City, Calif.). The most abundant transition for each peptide was used for quantification unless interference from the matrix was observed. In these cases, another transition free of interference was chosen for quantification.

An essential feature of label-free comparisons is that technical variations in sample processing, HPLC performance, sample injection, and mass spectrometer performance must be minimized over the entire course of the experiment. This study demonstrates the feasibility of maintaining consistent performance over more than 250 LC-MS/MS runs when using a 3-D discovery method for comparing sera from EP and IUP patients. However, analysis of the large volume of resulting data is complex. One critical factor when proteomes are fractionated is that the software utilized must be capable of matching and quantifying corresponding related ion currents across adjacent fractions because slight variations in distribution of proteins or peptides across fractions is inevitable in complex samples. The Rosetta Elucidator software used in this study combines data for a given peptide across fractions provided that at least one MS/MS spectra in each fraction resulted in the correct peptide identification. Furthermore, protein intensities are based upon the peptide identifications associated with the protein. Hence, although data alignment and quantification is conducted at the MS signal intensity level, correct annotation of peptides and grouping of peptides into consensus proteins is still critically important. Comparisons of alternative peptide score filtering and assignment of peptides to proteins showed that using the Peptide and Protein Tellers with relatively stringent filtering criteria minimized quantitative noise with identification of 70 candidate biomarkers that exhibited at least 2.5-fold differences between the EP and IUP groups. Further statistical analysis at the peptide level subsequently was used to select the most promising 12 candidate biomarker for future validation efforts in an independent patient cohort, which included known and novel EP biomarkers. This analysis also identified specific isoforms of some known proteins and specific proteolytically processed forms of ADAM12 that are EP biomarkers. Interestingly, label-free discovery analysis intensities for several known reference serum proteins compared favorably with their reported abundance levels, and relative abundances of candidate biomarkers from the label-free discovery analysis were consistent with label-free pilot MRM validation assay values for both serum pools and individual samples that constituted these pools. These results demonstrate robust, reproducible, in-depth 3-D serum proteome discovery, and subsequent pilot-scale validation studies readily can be achieved using label-free quantitation strategies.

Example 2

Strategy for Discovery of EP Serum Biomarkers Using Label-Free GeLC-MS/MS

A flow diagram summarizing the 3-D method for quantitative comparisons of serum from EP and IUP patients can be found at Beer et al, J. Proteome Res., 10(3):1126-38 (2011) at FIG. 1, incorporated by reference herein. Major protein depletion followed by GeLC-MS/MS is an efficient approach to identify a wide range of proteins in complex biological fluids such as serum.[6,23,34] In this study, the SDS gel separation was performed until the tracking dye migrated 2.0 cm. While performing longer gel separations and using a greater number of gel slices would further increase depth of proteome coverage, the major trade-offs are that throughput proportionally decreases and the complexity of the data set can exceed the capacity of existing software to perform quantitative comparisons.

Example 3

GeLC-MS/MS Comparison of EP and IUP Serum Pools

Depleted sera from nine EP and nine IUP patients were quantitatively compared by label-free LC-MS/MS analysis of pooled tryptic digests. Table 1 summarizes the scope of the experiment, which included a total of 252 LC-MS/MS runs for the discovery phase. Isotope groups (note 1) are the multiple features (discrete m/z signals) that comprise a peptide's isotopic envelope. The isoltope groups were filtered on: $z>1$, $z<5$, Peak time score=0.7; Peak m/z score=0.8 prior to DTA creation.

TABLE 1

| Summary of GeLC-MS/MS Comparison of EP and IUP Sera | |
|---|---|
| Samples | 6 pools × duplicates |
| Fractions/Pool | 21 |
| Total LC-MS/MS Runs | 252 |
| High Quality Features | 1,095,293 |
| High Quality Isotope Groups[1] | 251,889 |
| Filtered Isotope Groups for DTAs[2] | 227,663 |

All runs for a given gel slice were performed in a group starting at the top of gel to minimize variations in HPLC and mass spectrometer performance, although the order of performing analyses was randomized within gel slice groups to minimize the potential for experimental bias. These data produced approximately 1.1 million features, that is, discrete ion signals with unique elution times and m/z values. Retention time alignments and feature extractions across the entire chromatographic window where peptides eluted (20-75 min with a maximum 4 min window of variation) were performed within Elucidator using the Peak Teller algorithm. The software corrected for local retention time shifts across all runs for each fraction and removed noise and background. Figures generated therefrom (not shown) show retention time shifts among the 12 LC-MS/MS runs for three different gel slices run at the beginning (gel slice 1), middle (slice 10), and near the end (slice 20) of the entire experiment. Retention times typically varied by less than 1 min among the 12 runs for each fraction, with the greatest variation occurring early in the gradient where the most hydrophilic peptides eluted.

Example 4

Identification and Prioritization of Candidate Biomarkers

The Elucidator 2-D visual script (not shown) was used for initial identification of apparently significant differences between EP and IUP specimens as described in the Examples above. This analysis resulted in identification of 70 putative candidate biomarkers (FIG. 7) based on at least two identified peptides with p<0.001 (ANOVA) and at least 2.5-fold increases or decreases in the EP group compared to the IUP group. A 2.5-fold cut-off was selected for several reasons. First, label-free quantitation was expected to exhibit increased variation compared to other quantitation methods; hence a more conservative fold change of 2.5 was initially chosen rather than a typical 1.5-2.0 fold cutoff used in many proteomic studies. Second, proteins exhibiting more subtle differences in average values between clinical groups are unlikely to be good biomarkers because most blood biomarkers exhibit relatively wide ranges in concentration, even within clinical groups. However, inspection of resulting peptide intensities across all pools and duplicate LC-MS/MS runs showed that for some proteins, very large increases were observed in a single pool, with varying degrees of overlap between groups for the remaining pools. In addition, most of the putative biomarkers that were observed to be elevated in EP appeared to correlate with an observed higher hemolysis in EP pool 2 compared with all other pools. Consistent with this concern, the largest overall fold increases for EP were multiple database entries for the hemoglobin subunits (FIG. 7). In addition, analysis of peptide trends for some putative biomarker candidates showed wide variations indicative of substantial noise at the peptide level for a number of proteins. The most common sources of this noise included: very weak signals, interference from unrelated incompletely resolved ions, minor variations in peptide elution, and/or imperfect alignment of corresponding peaks within a gel slice group.

To further prioritize candidate biomarkers based on their ability to distinguish between EP and IUP, we considered two additional statistical parameters, sumZscores and $P_m$ for each identified peptide, rather than a strict fold change cutoff to identify candidate biomarkers (see Methods and Supporting Information). A graph showing the statistical evaluation of peptide probabilities, specifically the c\Correlation between sumZscore and $P_m$ for the complete set of 8,438 peptides identified using Peptide Teller to annotate features can be found at FIG. 2 of at Beer et al, J. Proteome Res., 10(3):1126-38 (2011) at FIG. 1, incorporated by reference herein. Vertical scatter plots illustrate the log intensity distributions of peptides from the Groups I-IV regions of the plot (data not shown, See, Beer et al, cited above). Blue datapoints are from EP samples and brown datapoints are from IUP samples. Horizontal lines indicate average values for the group. The multiple peptides are not necessarily from the same protein and therefore may exhibit opposing trends. There is no or minimal overlap of peptide levels for the two outcomes in Group I and Group II. There is extensive overlap in Group III and Group IV.

Interestingly, although sumZscore and $P_m$ are distinct and independently defined, we observed an encouraging trend governing the lower bound on sumZscore based on both the current data set (data not shown. See, Beer et al.) and simulated data. Specifically, as we restricted $P_m$ to lower values, that is, filtering for peptides with good $P_m$ scores, we also guaranteed a good lower bound on sumZscore (data not shown). Hence, there is negligible benefit to considering both parameters over considering $P_m$ alone. To identify the highest priority candidate biomarkers, we selected those proteins where at least 80% of the identified peptides had $P_m$<0.3 and detectable intensities for at least eight of the 12 data sets.

This analysis identified nine high-priority candidate biomarkers as shown in Table 2. In col. 3, "significant peptides" are those with the highest probability of correctly classifying new data into the correct group. In col. 4 of the table, "fold change" using IUP as the reference and based only on significant peptides as defined above. Hence, some values differ from those shown in FIG. 7.

TABLE 2

Selected Candidate Biomarkers of Ectopic Pregnancy

| Gene Name | Protein Description | # Significant Peptides[a]/ Total | Fold Change[b] |
|---|---|---|---|
| ADAM12 | ADAM 12 precursor | 8/8 | −21.9 |
| PSG7 | Pregnancy specific beta-1-glycoprotein 7 precursor | 4/5 | −13.4 |
| ISM2 | Isthmin 2 (Thrombospondin, type I domain containing 3 isoform 1) | 9/10 | −12.3 |
| PSG11 | Pregnancy specific beta-1-glycoprotein 11 isoform 1 | 4/5 | −11.7 |
| PSG9 | Pregnancy specific beta-1-glycoprotein 9 (PSG9 protein) | 15/15 | −10.4 |
| PSG1 | Isoform 2 of Pregnancy-specific beta-1-glycoprotein 1 | 4/4 | −9.9 |
| PSG2 | Pregnancy-specific beta-1-glycoprotein 2 precursor | 2/2 | −9.7 |
| CGB | Choriogonadotropin subunit beta precursor (β-hCG) | 4/4 | −4.9 |
| CGA | Glycoprotein hormones alpha chain precursor | 3/3 | −4.9 |
| PAPPA | Pappalysin-1 precursor | 20/40 | −34.1 |
| CSH1 | Chorionic somatomammotropin hormone precursor | 3/14 | −54.7 |
| PAEP | Progestagen-associated endometrial protein | 2/7 | −2.9 |

In addition, three proteins from the initial candidate biomarker list (PAPPA, CSH1, and PAEP) that failed the stringent $P_m$ statistical test were added to the high-priority candidate biomarker list due to their previously reported association with EP.[8,13]

Elucidator peptide trend plots were used to evaluate further the correlation of peptide intensities within a protein with EP and IUP and to visualize the effectiveness of our statistical tests. First, known common contaminants such as keratins and trypsin were removed and signals from duplicate analyses were averaged for all 8,438 high-confidence peptides (Peptide Teller probability>0.8). Then, data were Z-score transformed to emphasize relative intensity changes and adjust for differences in signal intensity of different peptides. Representative peptide trends are shown in FIGS. 3A-3D. As expected, based upon the above analyses, ADAM12 (FIG. 1A) and ISM2 (FIG. 1B) show consistent differences between experimental groups and minimal variation in trends between peptides within these proteins. ISM2 had a single peptide that failed the probability of misclassification test out of 10 unique peptides annotated to this protein.

In contrast, the peptide trends for PAEP (FIG. 1C) were highly variable, with only two of seven peptides passing the probability of misclassification test. When peptide trends for putative biomarkers show such wide variability it becomes more difficult to predict whether such candidates will be useful biomarkers, as it is uncertain which subset of peptides most closely reflects the actual protein abundance levels. As noted above, this candidate was retained in our selected biomarker group both because it has been previously associated with EP and to test whether our probability of misclassification test is too restrictive and should be relaxed.

Finally, SELENBP1 (data not shown) is an example of a putative biomarker from the Elucidator comparison with an overall significantly higher abundance in EP. A peptide trend plot for SELENBP1 from the Elucidator analysis can be found in Beer et al, cited above, at FIG. 3D, where 5/6 peptides passed the ANOVA filter, but all peptides failed the custom statistical test. Although most peptides annotated to this protein show a consistent trend, the difference between groups is primarily due to a very high value in the single EP sample with the most hemolysis. These data suggest that this protein will be less specific than the high-priority biomarkers discussed above.

Quantitative changes of all putative candidate biomarkers also were examined by summing peptide intensities for each protein. Comprehensive peptide intensity reports for aligned data, prior to combining replicates, were generated in the Elucidator System and exported to Excel for the 70 putative candidate biomarkers identified in the initial Elucidator analysis. Peptides were sorted based on annotated protein description, peptide intensities for candidate biomarkers were extracted and summed, and fold change values were calculated from combined average intensities for EP or IUP at the individual peptide and protein levels. Technical replicates for the 12 candidate biomarkers listed in Table 2 showed good reproducibility. CVs ranged from 0.25-89% with 72% of samples having VCs less than 25%. The peptide sequences, individual sample intensity data, fold changes, and probability of misclassification ($P_m$) for these 12 selected biomarkers are shown in FIG. 6. The corresponding data for the other putative biomarkers listed in FIG. 7 are shown in Beer et al, J. Proteome Research, 10(3):1126-38 (2011).

To address closely related protein isoforms, the effects of potential incorrect assignment of shared peptides to the wrong isoform were evaluated for the selected candidate biomarkers in Table 2. All protein codes returned from the Rosetta Elucidator annotation were selected and these sequences were aligned to identify common and unique peptides. Fold changes were re-calculated considering only significant peptides and only isoform-specific significant peptides. The fold changes were very similar for all three approaches for all the high-priority biomarkers. In addition, all peptides from FIG. 6 were blasted against the same database to identify additional isoforms supported by identified peptides. Any ambiguous isoform identifications are noted in the footnote in FIG. 6.

Figure 2A:
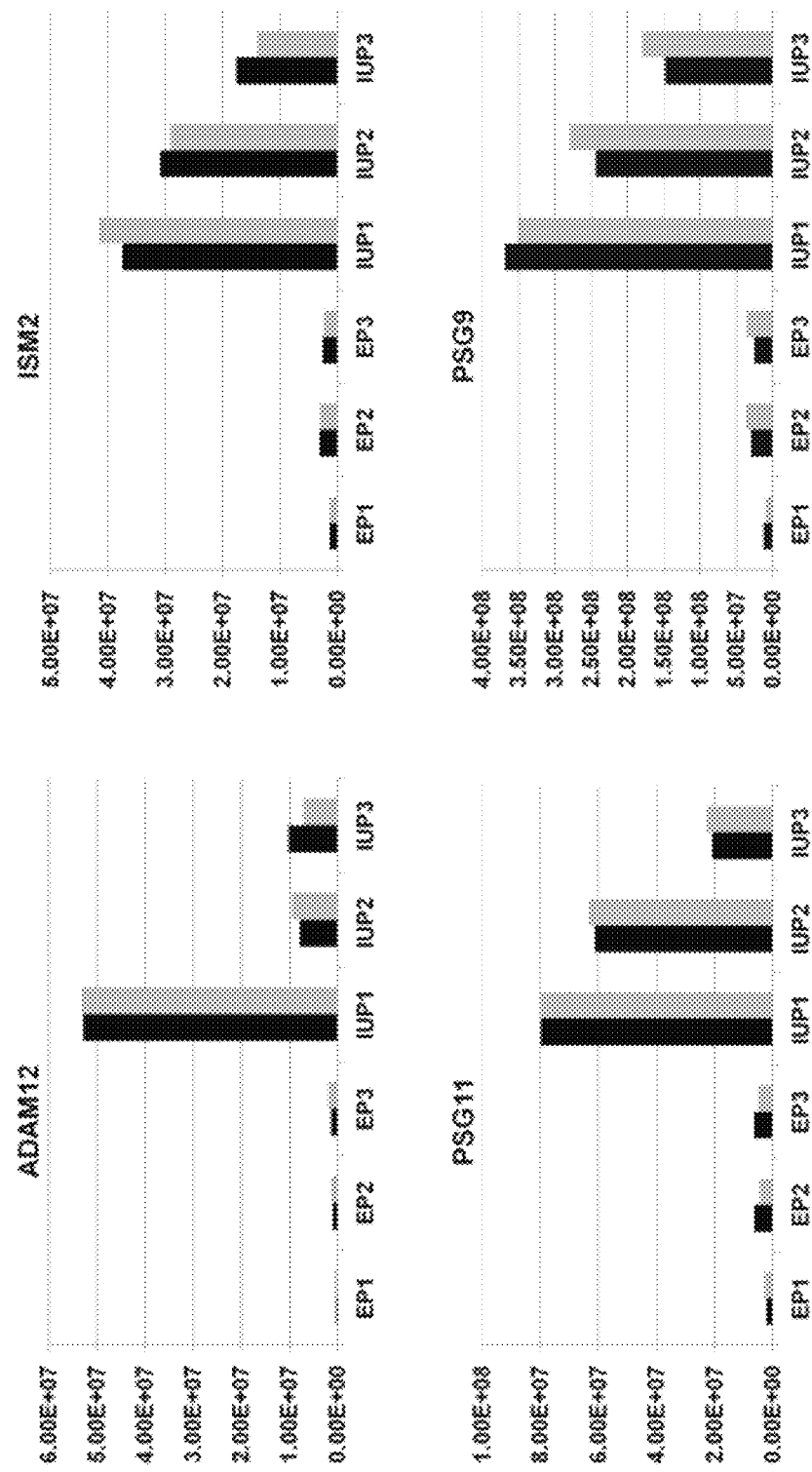
FIG. 2A are four graphs showing quantitative comparisons of candidate EP biomarkers ADAM12 and ISM2 and reference serum proteins PSG11 and PSG9. Protein intensities from the Elucidator label-free comparisons are shown for the three EP and three IUP pooled serum samples. Paired black and gray bars are replicate LC-MS analyses. Representative novel proteins identified above are decreased in ectopic pregnancy, including PSG9 and PSG11, the specific isoforms of the pregnancy-specific glycoprotein (PSG) protein family. PSG has previously been associated with ectopic pregnancy, but not at the specific protein isoform level.
Figure 2B:
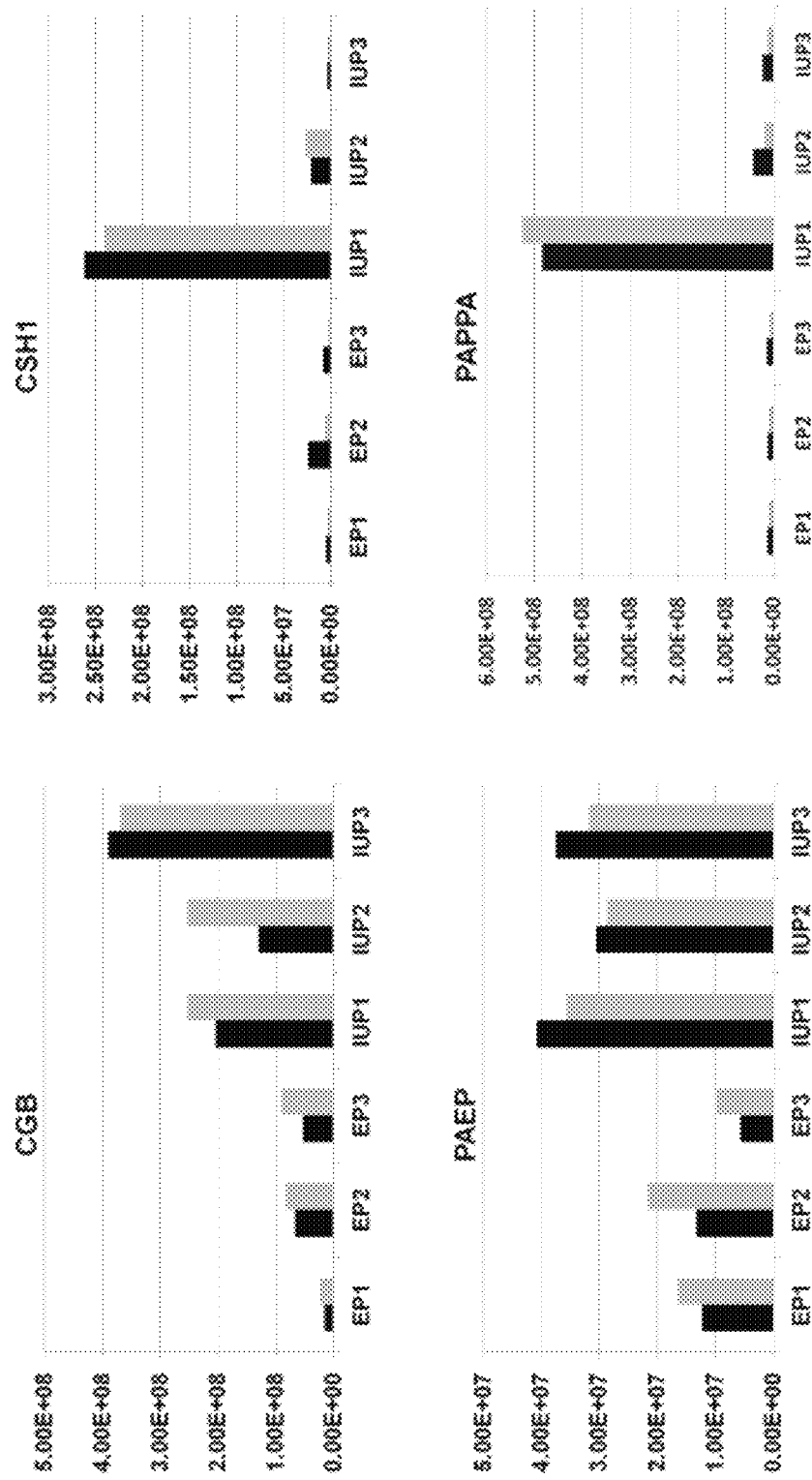
FIG. 2B are four graphs showing quantitative comparisons of representative additional proteins identified in this study that were previously reported candidate biomarkers of EP, namely CGB, CHS1, PAEP and PAPPA.
Figure 2C:
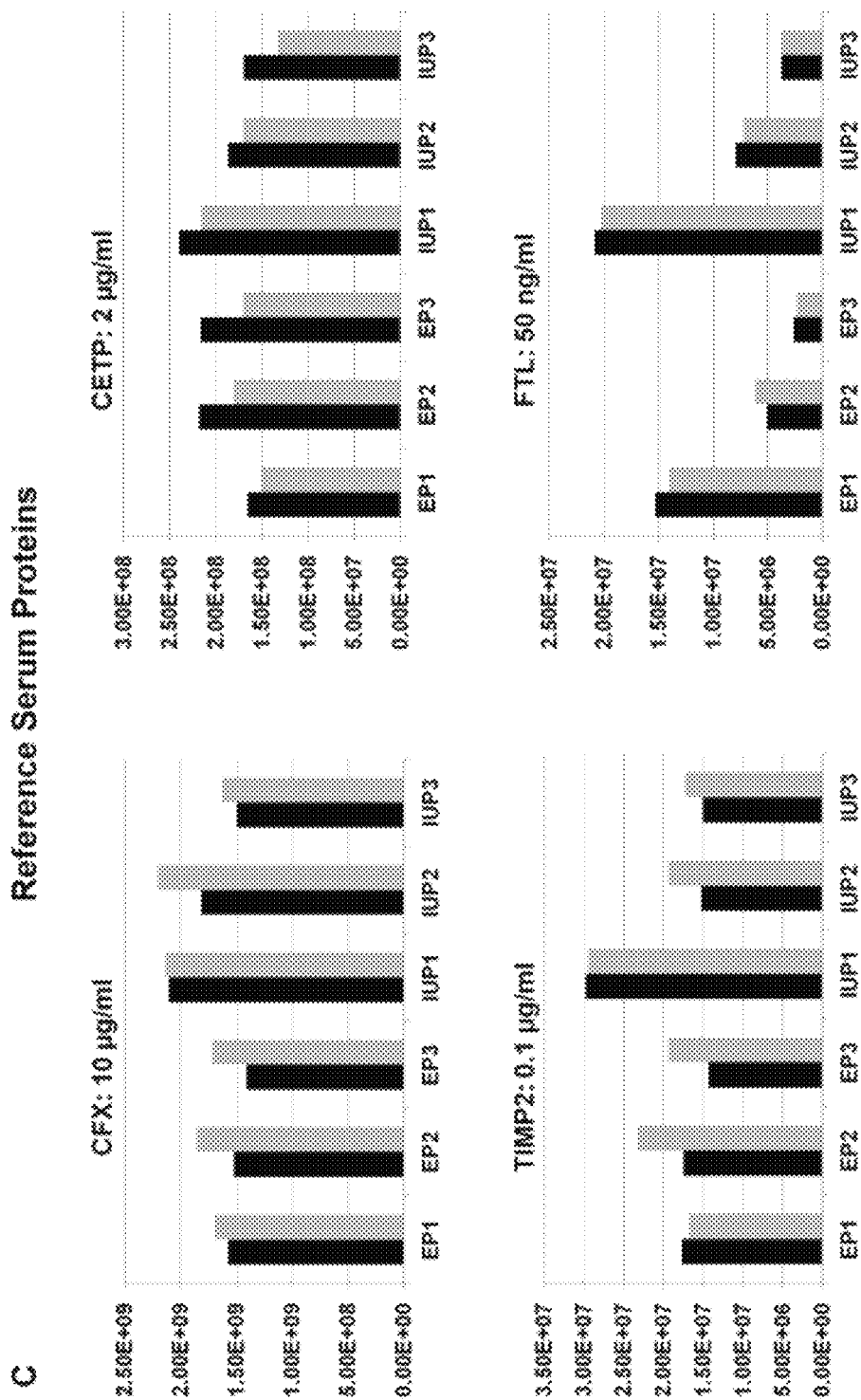
FIG. 2C are four graphs showing quantitative comparisons of four non-candidate, well-characterized serum proteins with known abundance levels that cover a wide concentration range, i.e., CFX, CETP, TIMP2 and FTL. The similar levels of these proteins between groups suggests there is no overall bias in protein recovery specific to either IUP or EP.

Quantitative comparisons of individual technical replicates are shown in FIG. 2 for representative candidate biomarkers and several reference non-candidate serum proteins. As expected, the trends at the protein level closely parallel those at the individual peptide level for those proteins where there was minimal noise and variability for the majority of peptides, such as ADAM12 and ISM2. These data further illustrate that overall protein intensities for duplicate runs were highly consistent. Evaluation of representative non-candidate serum proteins with known normal concentrations show very similar levels across all EP and IUP pools for the three most abundant proteins. Interestingly, there is very good agreement between known serum levels of these proteins and the observed protein intensities from the Elucidator analysis. Specifically, CFX at ~10 μg/ml, CETP at ~2 μg/ml, and TIMP1 at ~0.1 μg/ml[35,36] represent sequential order of magnitude differences in known concentrations, and the observed protein intensities are approximately $10^9$, $10^8$ and $10^7$, respectively. This illustrates excellent agreement between known concentrations and observed relative signals using label-free quantitation. Furthermore, out of a list of approximately 40 proteins with reported concentrations between 10-100 ng/mL,[35] we have identified 8 proteins, including FTL (FIG. 4), indicating moderate capacity to detect proteins in the ng/ml range using this method.

Example 5

Importance of MW Fractionation

Figure 3:
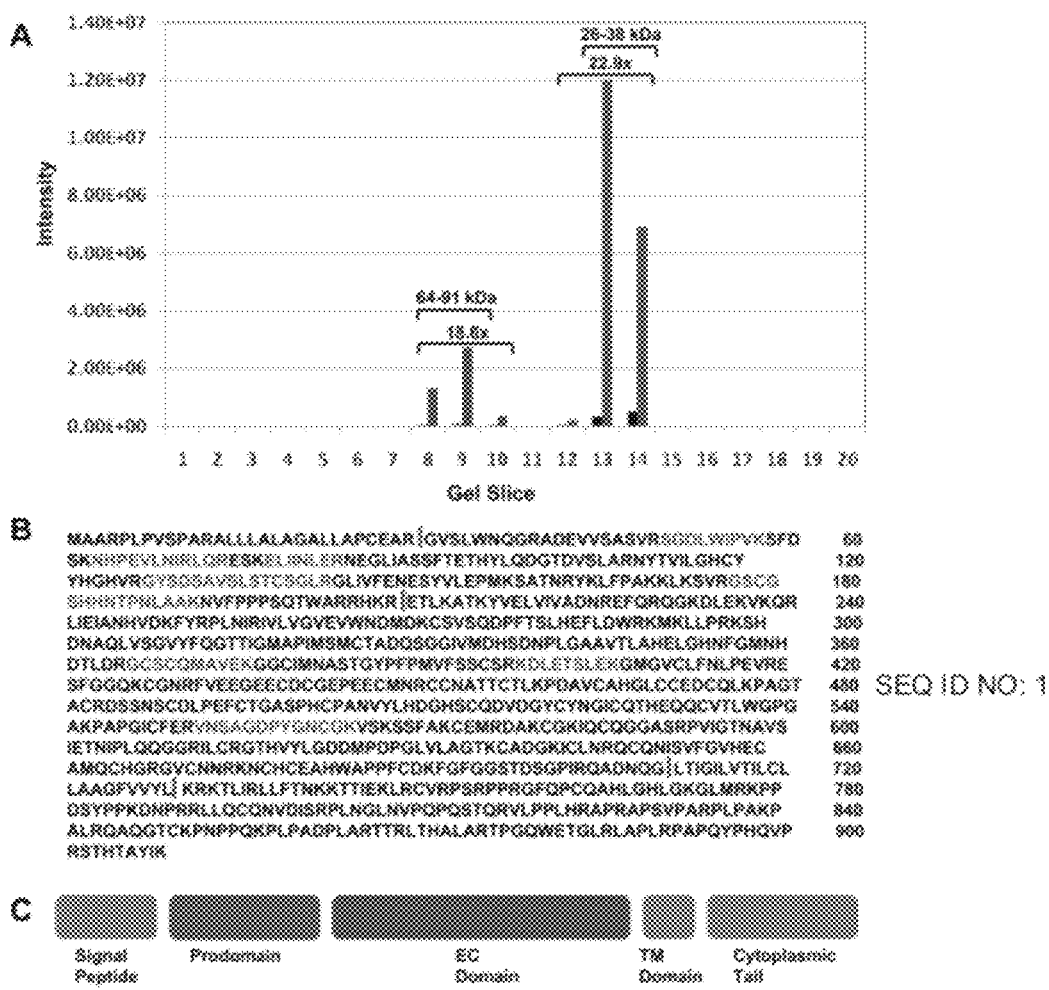
FIG. 3A is a GeLC-MS/MS-based identification of multiple molecular forms of ADAM12. This graph shows the distribution of intensities across gel fractions associated with ADAM12. The average peptide intensities observed in IUP for the prodomain (grey bars in gel slices 12-14) and extracellular domains (grey bars in gel slices 8-10) correspond to the color-coded sequences in FIG. 3B. Of each pair, the left side bars indicate the observed average intensities of the same peptides in EP. Both distinct forms of ADAM12 show similar fold changes between EP and IUP. The apparent MW and observed fold changes for the two regions are indicated.
FIG. 3B is a 909 amino acid sequence of ADAM12, in which the 6 peptides shaded in the prodomain (aa 30-aa 207) were found in gel slices 12-14; while three shaded peptides from slices 8-10 are found within the extracellular region (aa208-aa708) of the ADAM12 protein. Boundaries between the five different domains shown in FIG. 3C are indicated by vertical lines in the sequence.
FIG. 3C is a schematic diagram illustrating the five domains of ADAM12.
Figure 4A:
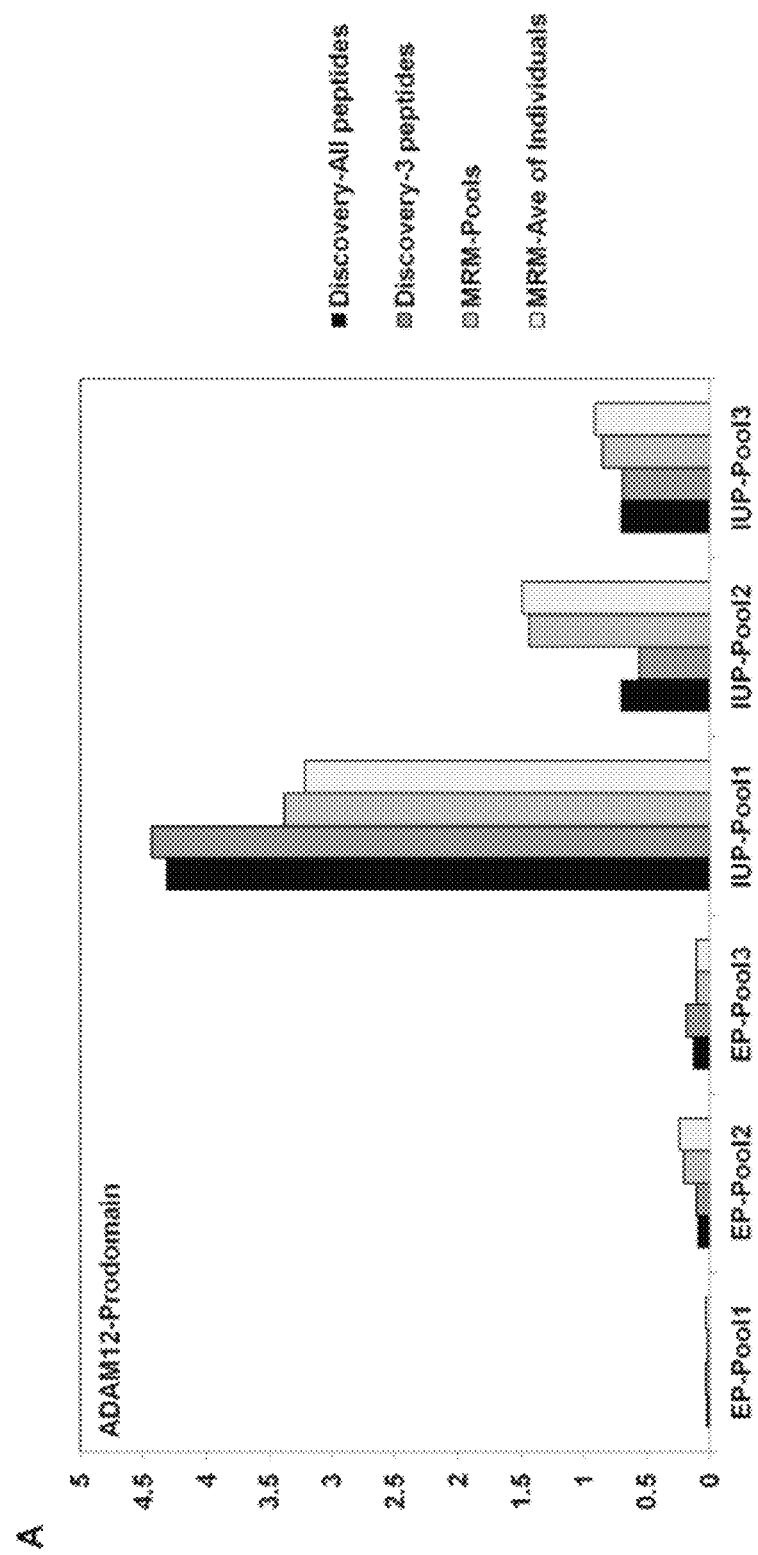
FIG. 4A is a comparison of quantitative data from label-free discovery and label-free validation. This graph shows peptide intensities for ADAM12 in the patient serum pools. "Discovery" data represent the normalized protein intensity from summing either all peptides identified or only three peptides used for MRM validation (as discussed in Example 1). "MRM-Pools" represents protein intensity data from the pooled tryptic digests used in the initial discovery experiment. "MRM-Ave of Individuals" shows the average protein intensity from MRM analysis of the three individual patients' sera (FIG. 4B) that were pooled for discovery. In each case, intensities were summed for gel slices 12-15 and normalized. These data demonstrate that label-free discovery quantitation and label-free MRM validation showed consistent relative trends that varied by less than two-fold.
Figure 4B:
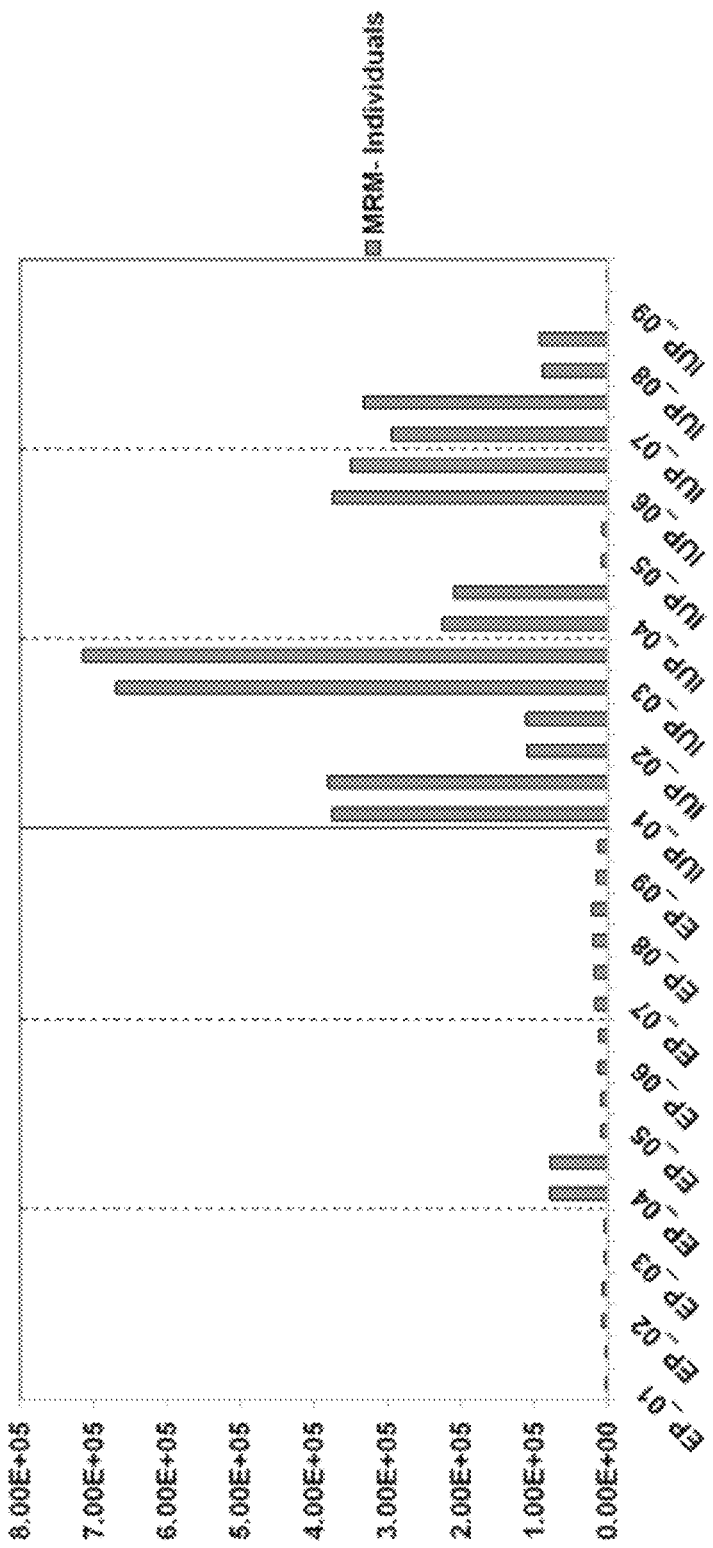
FIG. 4B is a graph showing ADAM12 protein quantitation results from MRM analysis of individual patient serum samples (replicates are shown by the paired bars). Data are the averaged intensity of the three MRM peptides (intensities were summed for gel slices 12-15 without normalization). Dashed lines indicate the individual samples that belong to the corresponding pools in FIG. 4A.
Figure 4C:
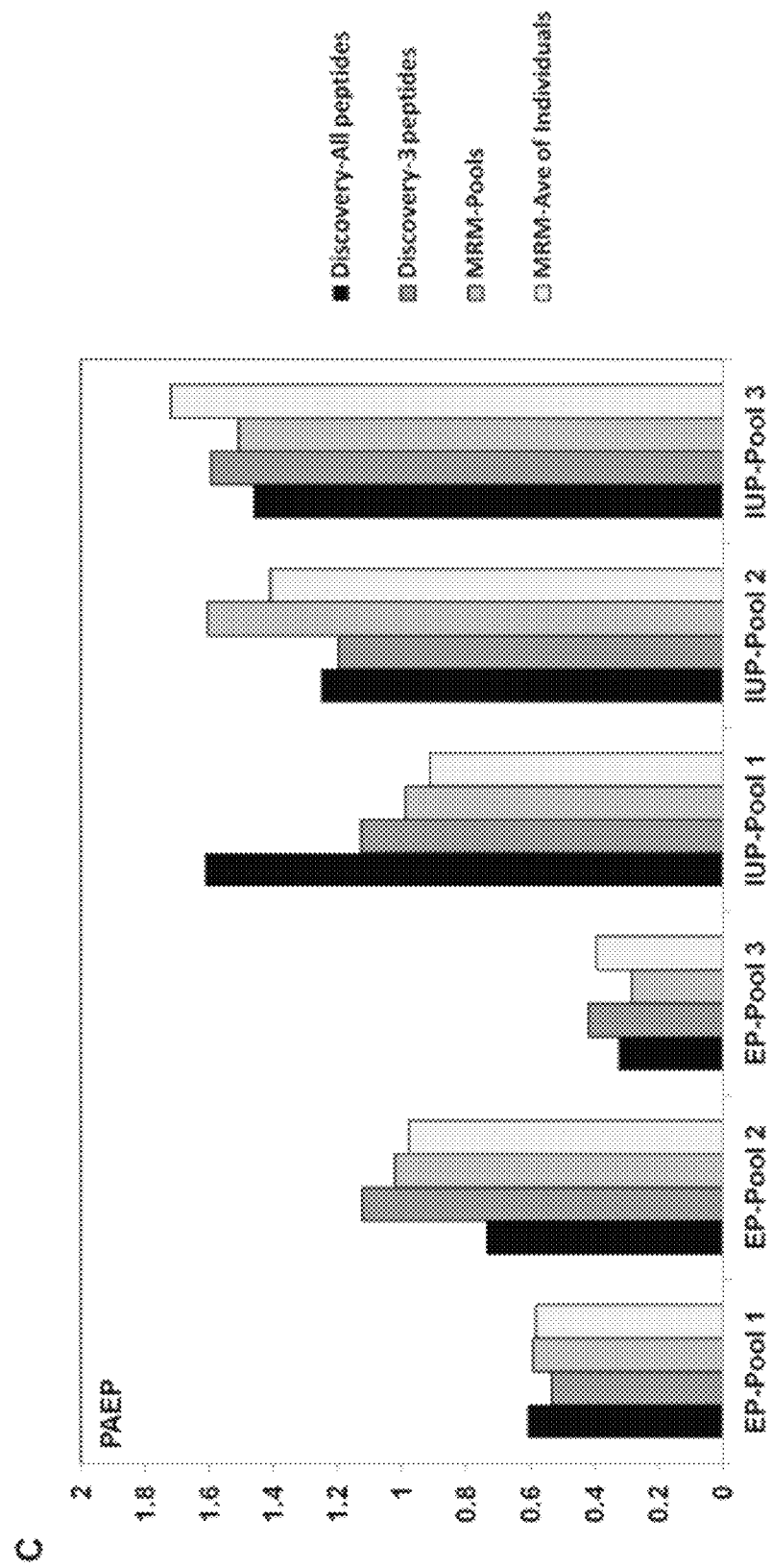
FIG. 4C is a comparison of quantitative data from label-free discovery and label-free validation for the candidate biomarker PAEP, which corresponds with FIG. 4A with the exception that five peptides were used for MRM quantitation. This graph shows peptide intensities for PAEP in the patient serum pools. "Discovery" data represent the normalized protein intensity from summing either all peptides identified or only three peptides used for MRM validation (as discussed in Example 1). "MRM-Pools" represents protein intensity data from the pooled tryptic digests used in the initial discovery experiment. "MRM-Ave of Individuals" shows the average protein intensity from MRM analysis of the five individual patients' sera (FIG. 4D) that were pooled for discovery. In each case, intensities were summed for gel slices 12-15 and normalized. These data demonstrate that label-free discovery quantitation and label-free MRM validation showed consistent relative trends that varied by less than two-fold.
Figure 4D:
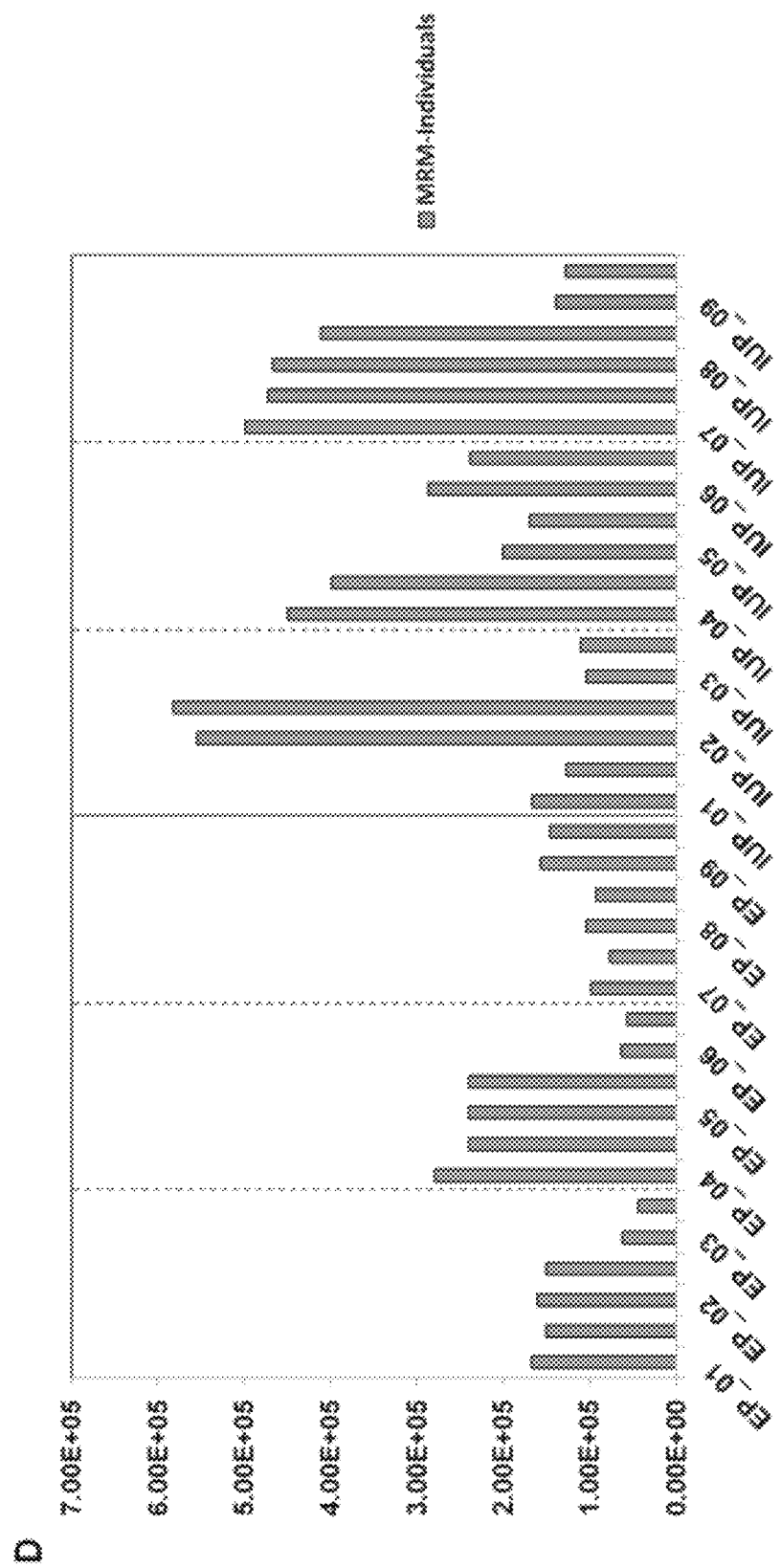
FIG. 4D is a graph showing PAEP protein quantitation results from MRM analysis of individual patient serum samples (replicates are shown by the paired bars). Data are the averaged intensity of the five MRM peptides (intensities were summed for gel slices 12-15 without normalization). Dashed lines indicate the individual samples that belong to the corresponding pools in FIG. 4C.
Figure 6B:
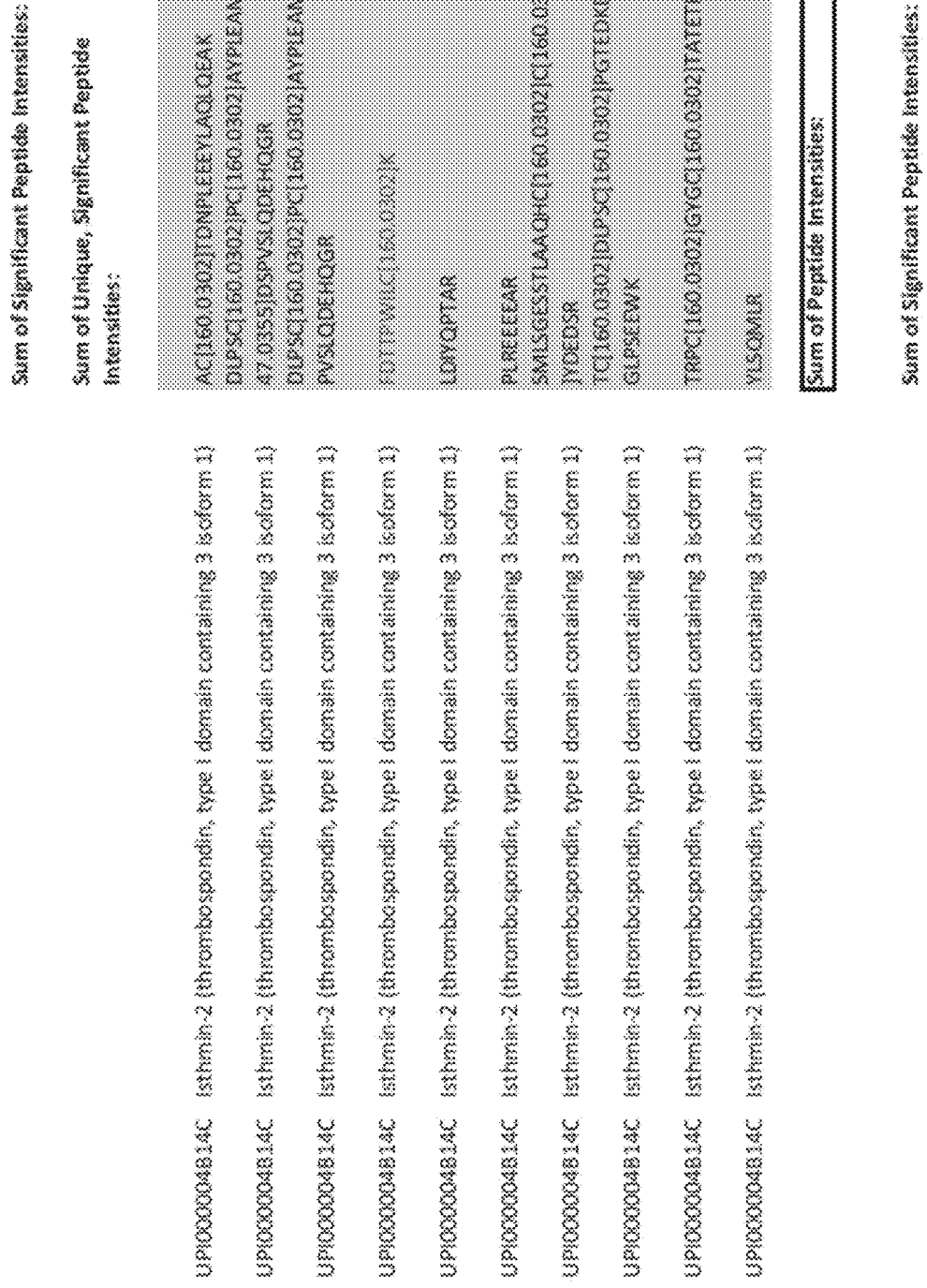
FIG. 6 is a list of peptide sequences and intensities for the 12 selected candidate biomarkers of Table 2.
Figure 6C:
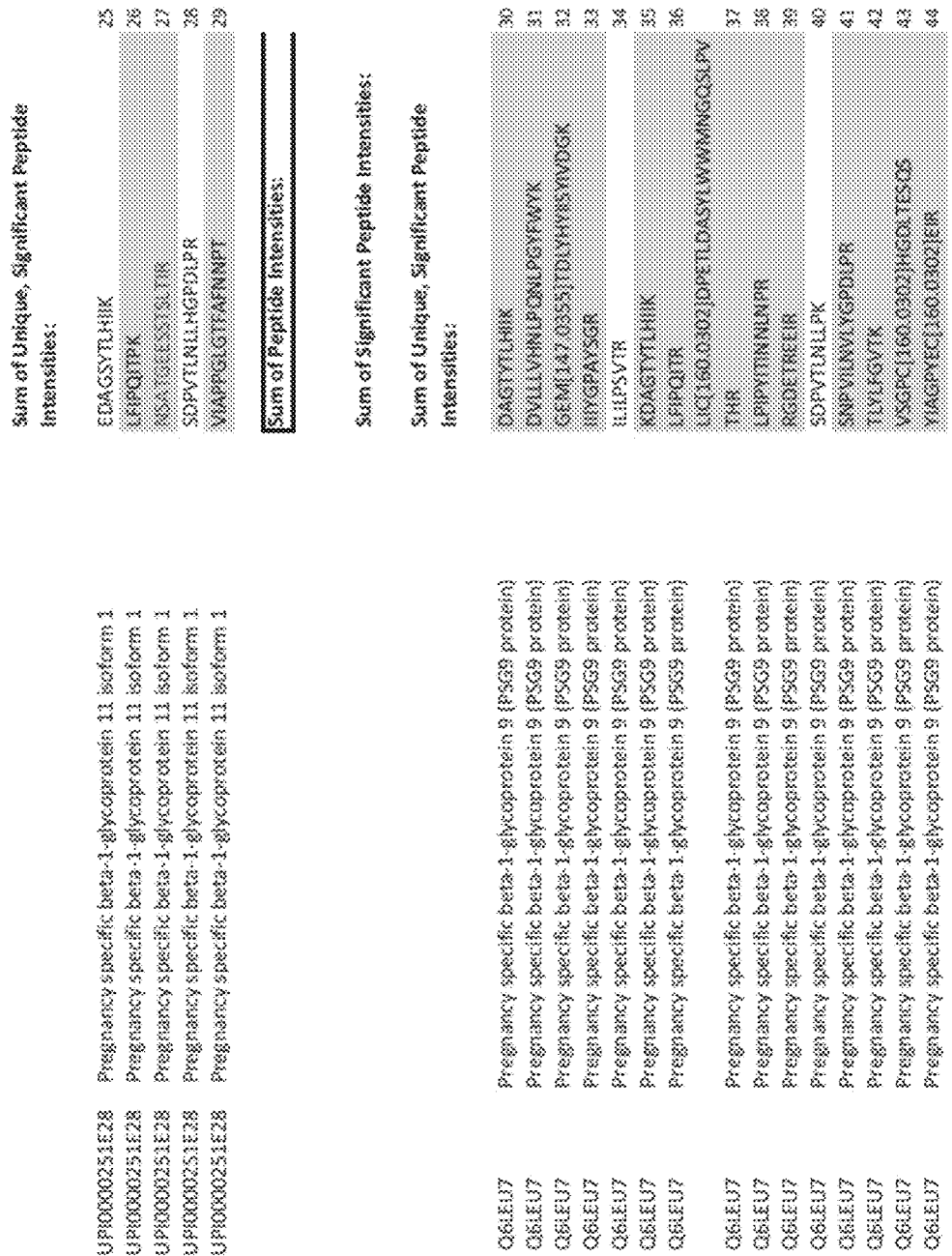
Figure 6E:
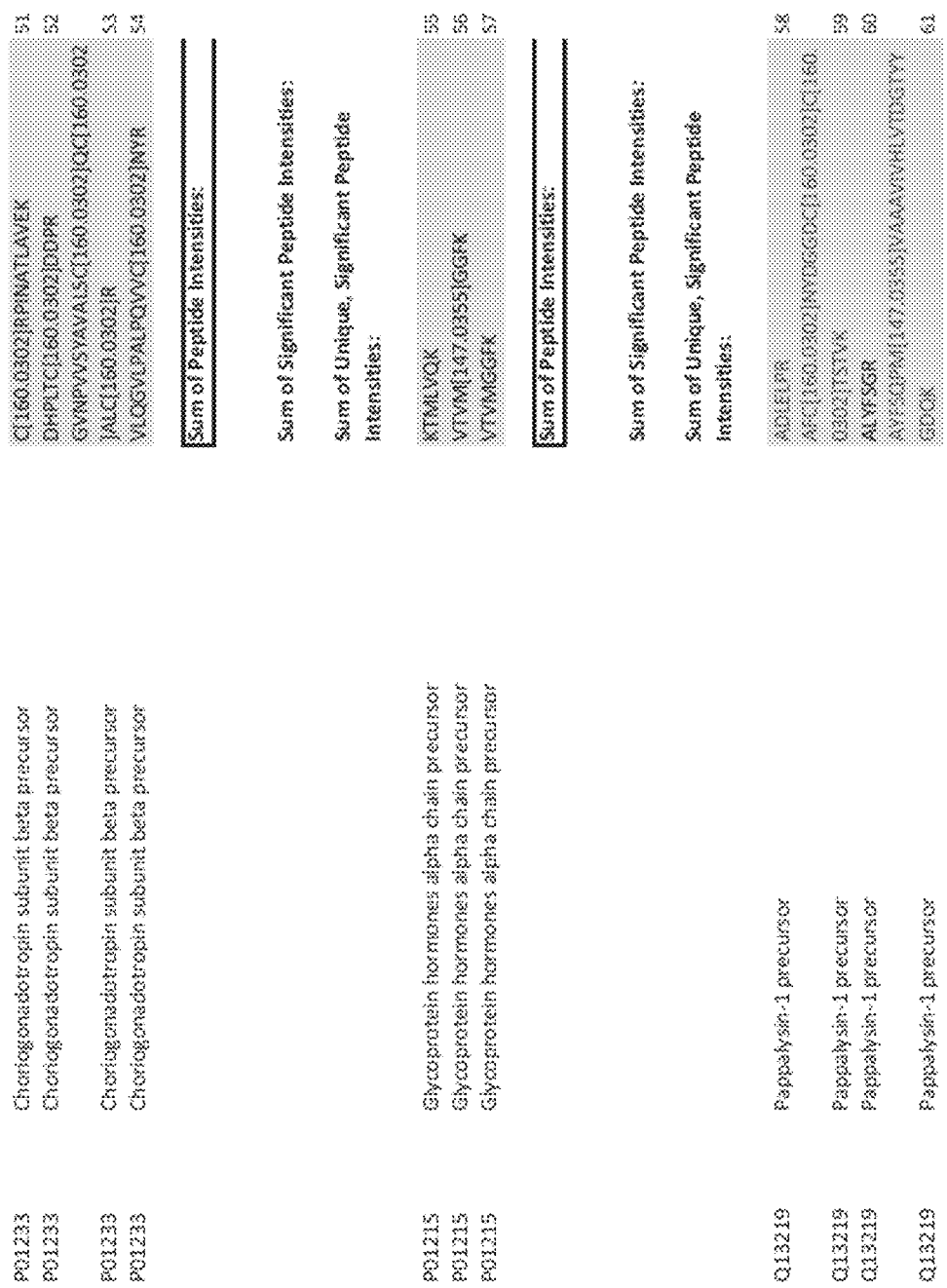
Figure 6G:
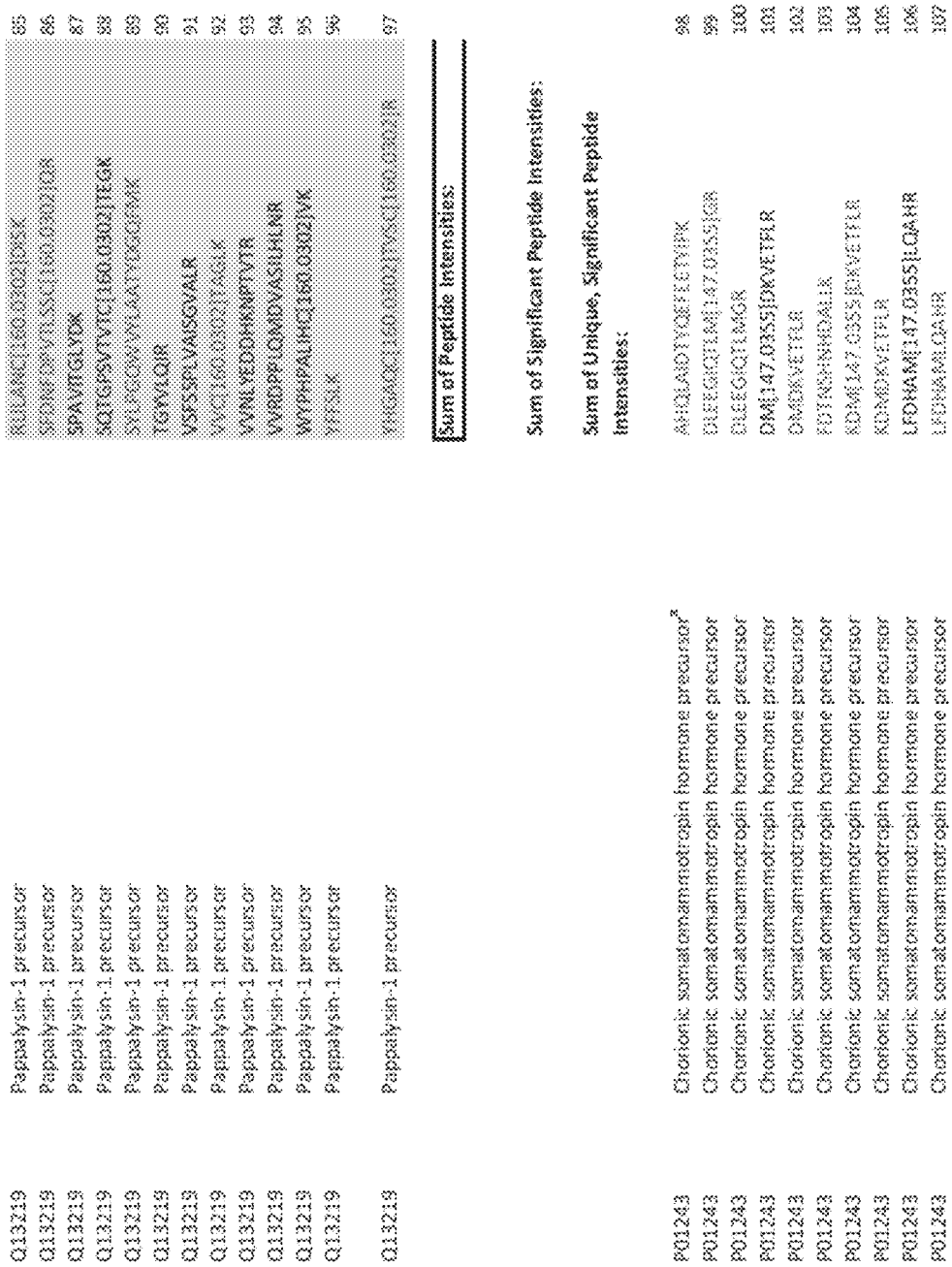
Figure 6H:
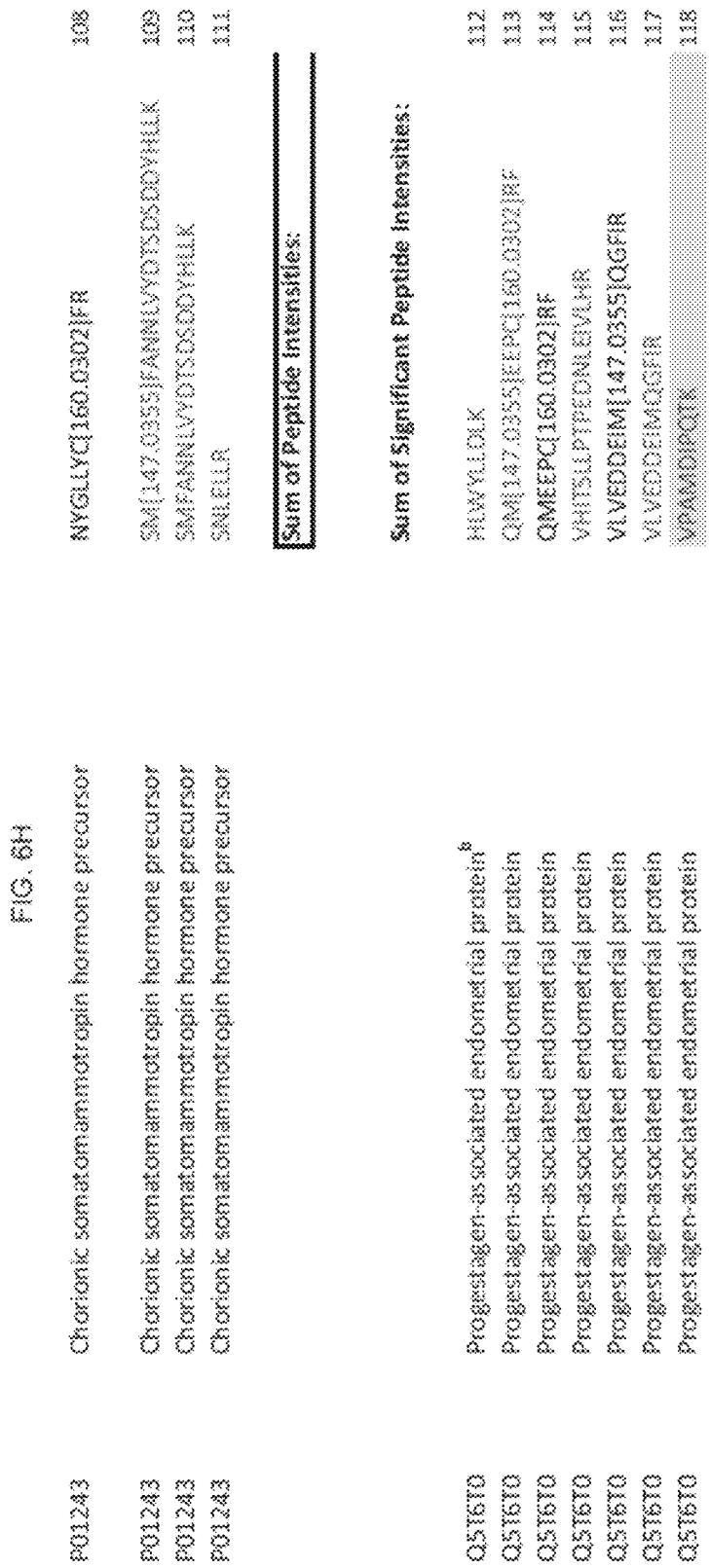

There are a number of alternative methods of fractionating serum proteins after major protein depletion, including strong cation exchange or off-gel electrophoresis of peptides, or solution IEF of proteins. However, fractionation of intact proteins by 1-D SDS gels preserves information about protein size, thereby providing insights into some forms of protein processing, major post-translational modifications, or alternative splicoforms that are more likely to be missed by alternative fractionation methods.[37] An interesting example in the current study is the observed molecular weight and peptide distribution of ADAM12 in serum (FIG. 3). It is apparent from the distribution of unique peptides to distinct regions of the gel that ADAM12 is represented in these sera by Pro-domain and EC domain fragments, but not by either full-length protein or the intact extracellular portion of the protein. The observed domain sizes as determined by SDS gel migration are in good agreement with those previously reported for ADAM12 domains on 1-D gels.[38]

While the two identified fragments show similar relative abundances in the current data set, it remains to be determined whether this trend holds up when larger patient populations are evaluated. Furthermore, knowledge of the precise molecular form(s) of a protein that correlate with a disease or medical condition can be invaluable when setting up validation assays using either MRM or immunoassay-based methods.

Example 6

Initial Verification and Validation of Selected Candidate Biomarkers

In an initial proof-of-principle independent test of the quantitative changes observed in the discovery phase, we used MRM analysis to further analyze the five of our 12 selected candidate biomarkers that were observed to be contained within gel slices 12-15. This group included a novel EP candidate biomarker identified in this study (ADAM12), two previously reported EP biomarkers that were ranked as high priority in the current study (CGA and CGB) and two previously reported EP biomarkers identified by the Elucidator workflow but with only a few high probability peptides (CSH1 and PAEP). For each gel slice, tryptic digests from the same nine depleted and fractionated IUP sera used in the discovery phase were pooled and used for targeted LC-MS/MS analysis in the Orbitrap mass spectrometer. A pool of IUP sera was selected because all targeted proteins of interest were observed to be higher in IUP compared with EP. Previously identified, as well as several theoretical tryptic peptides predicted to be suitable for MRM assays (no oxidation sensitive residues, readily cleavable tryptic boundaries, >6 and <25 residues), were analyzed using a parent mass list for the expected precursor ions as described in Methods. Peptides successfully identified in the targeted analysis were used to establish MRM assays. During MRM assay development using the same pooled IUP sample, at least five predicted strong transitions were tested and peptide identities were determined by the observed superposition of multiple transitions for each peptide of interest. Furthermore, the LC chromatographic systems used for the targeted analyses on the Orbitrap and the 4000Q MRM analyses were matched so that retention times were nearly identical on the two systems, thereby providing further confirmation that signals for the intended peptides were being quantitated in the MRM studies.

A scheduled MRM assay method was developed where at least three transitions per peptide and at least three peptides per protein could be confidently detected and quantified. This assay then was applied to quantitative analysis of the original EP and IUP pools as well as the nine individual EP and nine IUP sets of tryptic digests that were pooled for the original discovery experiments (FIG. 4). These MRM assays were conducted using label-free quantitation, that is, integration of signals for transitions without normalizing to an internal standard peptide.

As illustrated in FIGS. 6A-6D, there is consistent agreement of relative intensity trends between the discovery phase label-free protein quantitation using the Elucidator quantitation and the results from MRM analysis of the same pools. Similarly, when individual samples were quantified and the results of the three samples comprising each pool were averaged, these values were highly consistent with those obtained for the pooled sera using both label-free methods. The MRM analyses of the five tested biomarkers on all individual samples are shown in FIG. 5. Technical replicates of the individual EP and IUP samples showed good reproducibility. CVs ranged from 0 to 141%; however, only a single peptide from CSH1 in the EP set was highly variable due to low signal intensity. CVs for all other peptides were below 60% and the majority (94%) of peptides monitored had CVs less than 25%. Significance between groups was analyzed by unpaired t-test with Welch's correction (calculated using GraphPad Prism, v 5.03; GraphPad Software, LaJolla, Calif.). Not surprisingly, data from individual samples show more scatter and more overlap between groups than with pooled samples, with significant differences between groups for ADAM12, PAEP, and CGA (p≤0.05). This partial overlap between groups, as well as substantial heterogeneity within groups, is a common problem encountered for most biomarkers. For example, as indicated above, a single serum value of β-hCG (CGB), the current best diagnostic marker for EP, cannot completely segregate between EP and IUP due to substantial overlap of the ranges for EP and IUP specimens.[9] We observed similar results in this small cohort for CGB, as well as CSH1, which are not significantly different between groups. ADAM12, while significant when comparing mean intensities, also shows substantial variability among individual controls (IUP group) with some values overlapping the EP range. In one aspect, it is anticipated that the most definitive diagnostic test will be a multiple biomarker test to avoid any biomarker non-overlapping ranges between EP and IUP.

Example 7

Further Evaluation of ADAM12

The AUC from the quantitative multiple reaction monitoring data from the initial proteomics study for three ADAM-12 peptides was 0.81 for ADAM-12. Picking a cut-point that minimizes misclassification between the groups, the specificity was 78% for ADAM-12, with a sensitivity of 100%. Combining the ADAM-12 results with values of two known biomarkers (progestagen-associated endometrial protein [PAEP] and CHS-1) with use of CART, we achieved similar discrimination. Results for ADAM-12 were highly correlated with those for CSH-1 (r ¼ 0.90, P<0.0001), although PAEP was not correlated significantly with either CSH-1 (r ¼ 0.41, P¼ 0.09) or ADAM-12 (r ¼ 0.33, P¼ 0.19).

On the basis of these results, ADAM-12 was selected for further evaluation in serum from 99 women with EP and 100 women with IUP with use of DELFIA. Subject characteristics for the much larger independent cohort are shown in Table 3 below. There were no significant differences in maternal age, gestational age, race, ethnicity, site, or time frame of collection between the cases and controls. Gestational age was missing in 19 of 99 women in the EP group because of an unknown last menstrual period. The level of hCG was higher in the IUP group (7,586 mIU/mL) compared with the EP group (1,150 mIU/mL, P<0.0001) (Table 3).

TABLE 3

Subject characteristics for ADAM12 assay

| Characteristic | IUP (n) | IUP value | EP (n) | EP value | P value |
|---|---|---|---|---|---|
| Age (y)[a] | 98 | 27.51 +/− 6.70 | 98 | 29.02 +/− 6.11 | 0.101[b] |
| Gestational age (d)[a] | 100 | 48.80 +/− 12.34 | 80 | 45.14 +/− 19.07 | 0.140[b] |
| β-HCG (mIU/mL)[c] | 98 | 7,586 (47-36,589) | 99 | 1,150 (22-29,323) | <.0001[d] |
| Race | 97 | | 96 | | 0.888[e] |
| white | 63 | 65% | 63 | 65% | |
| black | 27 | 28% | 28 | 29% | |
| other | 7 | 7% | 5 | 5% | |
| Ethnicity-Hispanic | 58/97 | 50% | 57/96 | 50% | 0.953[f] |
| Site | 100 | | 99 | | 0.744[f] |
| Penn | 22 | 22% | 18 | 18% | |
| Miami | 42 | 42% | 46 | 46% | |
| USC | 36 | 36% | 35 | 35% | |
| Year | 100 | | 99 | | 0.400[e] |
| 2000-2003 | 13 | 13% | 7 | 7% | |
| 2004-2006 | 29 | 29% | 30 | 30% | |
| 2007-2009 | 58 | 58% | 62 | 63% | |

[a]Mean_SD.
[b]Two-sample t-test.
[c]Median (range).
[d]Wilcoxon rank sum test.
[e]Fisher's exact test.
[f]Pearson c2 test.

We again found a statistically significant decrease in ADAM-12 in the EP group (mean 11.7_48.2 ng/mL; median 2.5 ng/mL [range 2.5-440 ng/mL]) compared with the IUP group (mean 115.4_−214.1 ng/mL; median 18.6 ng/mL [range 2.5-1,131 ng/mL], P<0.0001) (data not shown). There was good discrimination between the groups as assessed by receiver operating characteristics (AUC ¼ 0.82). Whereas only 16 of 100 IUPs were below the minimum detectable limit, the majority of the patients with an EP (68 of 99) were below the sensitivity for the assay.

We examined the sensitivity and specificity of the test at three cutpoints, for the entire group and for subgroups stratified by gestational age and stratified by hCG level (Table 4 below). For all comparisons, specificity was maximized at the lowest cut-point and sensitivity was maximized at higher cut-points. For the group as a whole, as the cut-point was elevated from 2.53 to 48.49 ng/mL, the sensitivity increased (70% vs. 97%; P<0.001) whereas the specificity decreased (84% vs. 37%; P<0.001). The same change in cut-point resulted in a decrease in accuracy (77% vs. 67%; P=0.03).

Dichotomizing the samples by gestational age at 7 weeks demonstrated that the specificity of the test is greater at a gestational age of ≥7 weeks than <7 weeks for all three cut-points (100% vs. 70%, P<0.001 for cut-point 2.53; 87% vs. 41%, P<0.001 for cut-point 6.81; and 72% vs. 7%, P<0.001 for cut-point 48.49). There was no statistically significant difference in the sensitivity between the higher and lower gestational age groups (59% vs. 75%, P=0.14 for cut-point 2.53; 78% vs. 92%, P=0.08 for cut-point 6.81; and 100% vs. 96%, P=0.55 for cut-point 48.49). Accuracy was not significantly different between the high and low gestational ages at a lowest cut-point (85% vs. 73%, P=0.06) but was significantly higher in gestational age ≥7 weeks as compared with <7 weeks at a cutpoint of 48.49 (82% vs. 52%, P<0.001).

Dichotomized at an hCG level of 2,000 mIU/mL, ADAM-12 demonstrated higher specificity with higher hCG levels.

Our data confirm the value of ADAM-12 as a potential biomarker because we demonstrated that it can discriminate an EP from an IUP with a sensitivity of 70% and specificity of 84%. Choosing a higher cut-point, we optimized sensitivity to 97% (with a lower specificity). This marker performed better in women ≥7 weeks gestational age, with 100% specificity and 59% sensitivity at a low cut-point, and 100% sensitivity and 72% specificity at a higher cut-point.

In this study, we also found that ADAM-12 levels positively correlated with gestational age in the IUP group but not the EP group. The increase in specificity at higher gestational age and hCG levels is likely due to the rise of ADAM-12 levels in the IUP group without a corresponding rise in EP with increasing gestational age. The increased sensitivity levels at lower hCG levels in all but the group with near-perfect sensitivity (cut-point 48.49) may be a reflection of the weak, but significant, correlation of EPs with hCG. Therefore, the ADAM-12 test would be more sensitive in the group of EPs with lower hCG levels, irrespective of gestational age.

TABLE 4

Sensitivity and specificity of ADAM-12 test

| Group | Ep (n) | IUP (n) | Sensitivity, % (CI)[a] | Specificity, % (CI)[a] | Accuracy, % (CI)[a] | Sensitivity, % (CI)[a] | Specificity, % (CI)[a] | Accuracy, % (CI)[a] | Sensitivity, % (CI)[a] | Specificity, % (CI)[a] | Accuracy, % (CI)[a] |
|---|---|---|---|---|---|---|---|---|---|---|---|
| Whole group | 99 | 100 | 70 (60-79) | 84 (75-91) | 77 (70-83) | 89 (81-94) | 62 (52-72) | 75 (69-81) | 97 (91-99) | 37 (28-47) | 67 (60-73) |
| <7 wk gestational age | 53 | 54 | 75 (62-86) | 70 (56-82) | 73 (63-81) | 92 (82-98) | 41 (28-55) | 66 (57-75) | 96 (87-100) | 7 (2-18) | 52 (42-62) |
| ≥7 wk gestational age | 27 | 46 | 59 (39-78) | 100 (93-100) | 85 (75-92) | 78 (58-91) | 87 (74-95) | 84 (73-91) | 100 (87-100) | 72 (57-84) | 82 (71-90) |
| <2,000 mIU/mL hCG | 59 | 19 | 83 (71-92) | 53 (29-76) | 76 (65-85) | 98 (91-100) | 32 (13-57) | 82 (72-90) | 100 (94-100) | 21 (6-46) | 81 (70-89) |
| ≥2,000 mIU/mL hCG | 40 | 79 | 50 (34-66) | 90 (83-96) | 77 (69-84) | 75 (59-87) | 68 (57-78) | 71 (62-79) | 93 (80-98) | 39 (28-51) | 57 (48-66) |

[a]Two-sided 95% confidence intervals (CI) are presented, except where values equal 100%, in which case a one-sided 97.5% CI is presented The specificity was higher for hCG≥2,000 mIU/mL than hCG<2,000 mIU/mL at cut-point 2.53 and 6.81 (91% vs. 53%, P<0.001, and 68% vs. 32%, P=0.004, respectively). The sensitivity, however, was higher at hCG<2,000 mIU/mL compared with 82,000 mIU/mL at cutpoints of 2.53 and 6.81 (83% vs. 50%, P=0.001, and 98% vs. 75%, P<0.001, respectively). The extreme cut-point of 48.49, which optimized sensitivity, did not demonstrate significant differences between either sensitivity or specificity between the groups (100% for hCG<2,000 mIU/mL vs. 93% for >2,000 mIU/mL, P=0.06, and 21% vs. 39%, P=0.19, respectively). Accuracy was not different at the low cut-point (76% for hCG<2,000 mIU/mL vs. 77% for hCG ≥2,000 mIU/mL, P=0.79) but was significantly higher at hCG levels<2,000 mIU/mL versus ≥2,000 mIU/mL at the highest cut-point (81% vs. 57%, P=0.001).

Correlation between ADAM-12 levels and both gestational age and hCG levels was performed in the overall IUP and EP groups. Level of ADAM-12 was significantly correlated with gestational age in the IUP group (r = 0.66, P<0.0001) but not in the EP group (r = 0.20, P=0.07). When the two groups are graphed from 4 to 12 weeks, ADAM-12 levels rise in the IUP group as EP levels remain suppressed with increasing gestational age (data not shown). Level of ADAM-12 was more weakly, but significantly, correlated with hCG in both the IUP group (r = 0.53, P<0.0001) and the EP group (0.50, P<0.0001).

Each and every patent, patent application, and publication, including publications listed below, and publicly available peptide sequences cited throughout the disclosure, is expressly incorporated herein by reference in its entirety. In addition, Rausch et al, "A disintegrin and metalloprotease protein-12 as a novel marker for the diagnosis of ectopic pregnancy, Fertility and Sterility, 95(4):1373-8 (Mar. 15, 2011), and Beer et al, "Systematic discovery of ectopic pregnancy serum biomarkers using 3-D protein profiling coupled with label-free quantitation, J. Proteome Research, 10:1126-38 (epub Dec. 10, 2010) (March 2011) are expressly incorporated herein by reference in their entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

PUBLICATIONS

1. Anderson, N. L.; Anderson, N. G., The human plasma proteome: history, character, and diagnostic prospects. *Mol Cell Proteomics* 2002, 1, (11), 845-67.
2. Anderson, N. L., The roles of multiple proteomic platforms in a pipeline for new diagnostics. *Mol Cell Proteomics* 2005, 4, (10), 1441-4.

3. Rifai, N. et al., Protein biomarker discovery and validation: the long and uncertain path to clinical utility. *Nat Biotechnol* 2006, 24, (8), 971-83.
4. Anderson, N. L., The clinical plasma proteome: a survey of clinical assays for proteins in plasma and serum. *Clin Chem* 2010, 56, (2), 177-85.
5. Gerton, G. L. et al, A serum proteomics approach to the diagnosis of ectopic pregnancy. *Ann N Y Acad Sci* 2004, 1022, 306-16.
6. Choolani, M. et al, Proteomic technologies for prenatal diagnostics: advances and challenges ahead. *Expert Rev Proteomics* 2009, 6, (1), 87-101.
7. Cabar, F. R. et al, Serum markers in the diagnosis of tubal pregnancy. *Clinics (Sao Paulo)* 2008, 63, (5), 701-8.
8. Cartwright, J. et al, Serum biomarkers of tubal ectopic pregnancy: current candidates and future possibilities. *Reproduction* 2009, 138, (1), 9-22.
9. Barnhart, K. T., Clinical practice. Ectopic pregnancy. *N Engl J Med* 2009, 361, (4), 379-87.
10. Seeber, B. E.; Barnhart, K. T., Suspected ectopic pregnancy. *Obstet Gynecol* 2006, 107, (2 Pt 1), 399-413.
11. Hoover, K. W. et al, Trends in the diagnosis and treatment of ectopic pregnancy in the United States. *Obstet Gynecol* 2010, 115, (3), 495-502.
12. Daponte, A. et al, The value of a single combined measurement of VEGF, glycodelin, progesterone, PAPP-A, HPL and LIF for differentiating between ectopic and abnormal intrauterine pregnancy. *Hum Reprod* 2005, 20, (11), 3163-6.
13. Mueller, M. D. et al, Novel placental and nonplacental serum markers in ectopic versus normal intrauterine pregnancy. *Fertil Steril* 2004, 81, (4), 1106-11.
14. Abbott, J. et al, Ectopic pregnancy: ten common pitfalls in diagnosis. *Am J Emerg Med* 1990, 8, (6), 515-22.
15. Tay, J. I. et al, Ectopic pregnancy. *BMJ* 2000, 320, (7239), 916-9.
16. Omenn, G. S. et al, Overview of the HUPO Plasma Proteome Project: results from the pilot phase with 35 collaborating laboratories and multiple analytical groups, generating a core dataset of 3020 proteins and a publicly-available database. *Proteomics* 2005, 5, (13), 3226-45.
17. States, D. J. et al, Challenges in deriving high-confidence protein identifications from data gathered by a HUPO plasma proteome collaborative study. *Nat Biotechnol* 2006, 24, (3), 333-8.
18. Echan, L. A. et al, Depletion of multiple high-abundance proteins improves protein profiling capacities of human serum and plasma. *Proteomics* 2005, 5, (13), 3292-303.
19. Bjorhall, K. et al, Comparison of different depletion strategies for improved resolution in proteomic analysis of human serum samples. *Proteomics* 2005, 5, (1), 307-17.
20. Beer, L. A., Speicher, D. W., Immunoaffinity depletion of high abundance plasma and serum proteins. In *The Protein Protocols Handbook*, 3rd ed.; Humana Press: New York, 2009.
21. Fang, Y. et al, Quantitative analysis of proteome coverage and recovery rates for upstream fractionation methods in proteomics. *J Proteome Res* 2010, 9, (4), 1902-12.
22. Piersma, S. R. et al, Workflow comparison for label-free, quantitative secretome proteomics for cancer biomarker discovery: method evaluation, differential analysis, and verification in serum. *J Proteome Res* 2010, 9, (4), 1913-22.
23. Tang, H. Y. et al, A novel four-dimensional strategy combining protein and peptide separation methods enables detection of low-abundance proteins in human plasma and serum proteomes. *Proteomics* 2005, 5, (13), 3329-42.
24. Old, W. M. et al, Comparison of label-free methods for quantifying human proteins by shotgun proteomics. *Mol Cell Proteomics* 2005, 4, (10), 1487-502.
25. Zhu, W. et al, Mass spectrometry-based label-free quantitative proteomics. *J Biomed Biotechnol* 2010, 2010, 840518.
26. Elliott, M. H. et al, Current trends in quantitative proteomics. *J Mass Spectrom* 2009, 44, (12), 1637-60.
27. Mueller, L. N. et al, An assessment of software solutions for the analysis of mass spectrometry based quantitative proteomics data. *J Proteome Res* 2008, 7, (1), 51-61.
28. This software is no longer commercially developed as a result of the purchase of Rosetta Biosoftware by Microsoft Corporation.
29. Paweletz, C. P.; Wiener, M. C.; Bondarenko, A. Y.; Yates, N. A.; Song, Q.; Liaw, A.; Lee, A. Y.; Hunt, B. T.; Henle, E. S.; Meng, F.; Sleph, H. F.; Holahan, M.; Sankaranarayanan, S.; Simon, A. J.; Settlage, R. E.; Sachs, J. R.; Shearman, M.; Sachs, A. B.; Cook, J. J.; Hendrickson, R. C., Application of an end-to-end biomarker discovery platform to identify target engagement markers in cerebrospinal fluid by high resolution differential mass spectrometry. *J Proteome Res* 2010, 9, (3), 1392-401.
30. Neubert, H.; Bonnert, T. P.; Rumpel, K.; Hunt, B. T.; Henle, E. S.; James, I. T., Label-free detection of differential protein expression by LC/MALDI mass spectrometry. *J Proteome Res* 2008, 7, (6), 2270-9.
31. Rosetta Elucidator System v. 3.1 User Guide
32. Nesvizhskii, A. I.; Keller, A.; Kolker, E.; Aebersold, R., A statistical model for identifying proteins by tandem mass spectrometry. *Anal Chem* 2003, 75, (17), 4646-58.
33. Keller, A.; Nesvizhskii, A. I.; Kolker, E.; Aebersold, R., Empirical statistical model to estimate the accuracy of peptide identifications made by MS/MS and database search. *Anal Chem* 2002, 74, (20), 5383-92.
34. Wang, H.; Chang-Wong, T.; Tang, H. Y.; Speicher, D. W., Comparison of extensive protein fractionation and repetitive LC-MS/MS analyses on depth of analysis for complex proteomes. *J Proteome Res* 2010, 9, (2), 1032-40.
35. Anderson, L., Candidate-based proteomics in the search for biomarkers of cardiovascular disease. *J Physiol* 2005, 563, (Pt 1), 23-60.
36. Larsen, M. B.; Stephens, R. W.; Brunner, N.; Nielsen, H. J.; Engelholm, L. H.; Christensen, I. J.; Stetler-Stevenson, W. G.; Hoyer-Hansen, G., Quantification of tissue inhibitor of metalloproteinases 2 in plasma from healthy donors and cancer patients. *Scand J Immunol* 2005, 61, (5), 449-60.
37. Steen, H.; Mann, M., The ABC's (and XYZ's) of peptide sequencing. *Nat Rev Mol Cell Biol* 2004, 5, (9), 699-711.
38. Wewer, U. M.; Morgelin, M.; Holck, P.; Jacobsen, J.; Lydolph, M. C.; Johnsen, A. H.; Kveiborg, M.; Albrechtsen, R., ADAM12 is a four-leafed clover: the excised prodomain remains bound to the mature enzyme. *J Biol Chem* 2006, 281, (14), 9418-22.
39. Beer, L. A. et al., Systematic Discovery of Ectopic Pregnancy Serum Biomarkers Using 3-D Protein Profiling Coupled with Label-free Quantitation. *J. Proteom. Res.*, published on-line Dec. 10, 2010, DOI: 10.1021/pr1008866

The invention claimed is:

1. A diagnostic reagent or kit for use in diagnosing an ectopic pregnancy in a mammalian subject consisting of:
   i. a ligand that binds Isthmin2 (ISM2),
   ii. a ligand that binds the pro-domain or extracellular (EC) domain of ADAM12,
   iii. a ligand that binds pregnancy specific beta-1 glycoprotein isoform 7 (PSG7),
   iv. a ligand that binds pregnancy specific beta-1 glycoprotein isoform 11 (PSG11),
   v. a ligand that binds pregnancy specific beta-1 glycoprotein isoform 9 (PSG9), and
   vi. a ligand that binds pregnancy specific beta-1 glycoprotein isoform 2 (PSG2);
   wherein at least one of the ligands is covalently or non-covalently joined with a detectable label or immobilized upon a substrate.

2. A diagnostic reagent or kit for use in diagnosing an ectopic pregnancy in a mammalian subject consisting of:
   i. a ligand that binds Isthmin2 (ISM2),
   ii. a ligand that binds the pro-domain or extracellular (EC) domain of ADAM12,
   iii. a ligand that binds pregnancy specific beta-1 glycoprotein isoform 7 (PSG7),
   iv. a ligand that binds pregnancy specific beta-1 glycoprotein isoform 11 (PSG11),
   v. a ligand that binds pregnancy specific beta-1 glycoprotein isoform 9 (PSG9), and
   vi. a ligand that binds pregnancy specific beta-1 glycoprotein isoform 2 (PSG2); and a ligand that binds to a protein or peptide fragment selected from the group consisting of:
   vii. pregnancy specific beta-1 glycoprotein isoform 1 (PSG1),
   viii. choriogonadotropin subunit beta precursor (CGB);
   ix. glycoprotein hormones alpha chain precursor (CGA);
   x. pappalysin-1 precursor (PAPPA);
   xi. chorionic somatomammotropin hormone precursor (CSH1); and
   xii. progestagen-associated endometrial protein (PAEP); or
   xiii a combination of ligands, each ligand binding a different peptide or protein of (vii) through (xii)
   wherein at least one of the ligands is covalently or non-covalently joined with a detectable label or immobilized upon a substrate.

3. The reagent or kit according to claim 1, wherein each of said ligands is immobilized upon a substrate.

4. The reagent or kit according to claim 1, wherein said ligands are proteins or peptides.

5. The reagent or kit according to claim 4, wherein said ligand is an antibody or fragment thereof.

6. The reagent of kit according to claim 1, wherein each of said ligands is covalently or non-covalently joined with a detectable label.

7. A diagnostic reagent or kit for use in diagnosing an ectopic pregnancy in a mammalian subject consisting of (i) a ligand that that binds to Isthmin2 (ISM2), and (ii) a ligand that binds to the pro-domain or extracellular (EC) domain of ADAM12, wherein at least one of the ligands is covalently or non-covalently joined with a detectable label or immobilized upon a substrate.

8. A diagnostic reagent or kit for use in diagnosing an ectopic pregnancy in a mammalian subject consisting of
(i) a ligand that that binds to Isthmin2 (ISM2),
(ii) a ligand that binds to the pro-domain or extracellular (EC) domain of ADAM12, and one or more ligands selected from:
iii. a ligand that binds to pregnancy specific beta-1 glycoprotein isoform 7 (PSG7),
v. a ligand that binds to pregnancy specific beta-1 glycoprotein isoform 11 (PSG11),
v. a ligand that binds to pregnancy specific beta-1 glycoprotein isoform 9 (PSG9), and
vi. a ligand that binds to pregnancy specific beta-1 glycoprotein isoform 2 (PSG2),
wherein at least one of the ligands is covalently or non-covalently joined with a detectable label or immobilized upon a substrate.

9. A diagnostic reagent or kit for use in diagnosing an ectopic pregnancy in a mammalian subject consisting of
(i) a ligand that that binds to Isthmin2 (ISM2),
(ii) a ligand that binds to the pro-domain or extracellular (EC) domain of ADAM12,
one or more ligands selected from:
iii. a ligand that binds to pregnancy specific beta-1 glycoprotein isoform 7 (PSG7),
v. a ligand that binds to pregnancy specific beta-1 glycoprotein isoform 11 (PSG11),
v. a ligand that binds to pregnancy specific beta-1 glycoprotein isoform 9 (PSG9), and
vi. a ligand that binds to pregnancy specific beta-1 glycoprotein isoform 2 (PSG2); and
one or more ligands selected from:
vii. a ligand that binds to pregnancy specific beta-1 glycoprotein isoform 1 (PSG1),
viii. a ligand that binds to choriogonadotropin subunit beta precursor (CGB);
ix. a ligand that binds to glycoprotein hormones alpha chain precursor (CGA);
x. a ligand that binds to pappalysin-1 precursor (PAPPA);
xi. a ligand that binds to chorionic somatomammotropin hormone precursor (CSH1); and
xii. a ligand that binds to progestagen-associated endometrial protein (PAEP),
wherein at least one of the ligands is covalently or non-covalently joined with a detectable label or immobilized upon a substrate.

10. A diagnostic reagent or kit for use in diagnosing an ectopic pregnancy in a mammalian subject consisting of (i) a ligand that that binds to Isthmin2 (ISM2), (ii) a ligand that binds to the pro-domain or extracellular (EC) domain of ADAM12, and one or more ligands selected from:
vii. a ligand that binds to pregnancy specific beta-1 glycoprotein isoform 1 (PSG1) or a fragment thereof,
viii. a ligand that binds to choriogonadotropin subunit beta precursor (CGB) or a fragment thereof;
ix. a ligand that binds to glycoprotein hormones alpha chain precursor (CGA) or a fragment thereof;
x. a ligand that binds to pappalysin-1 precursor (PAPPA) or a fragment thereof;
xi. a ligand that binds to chorionic somatomammotropin hormone precursor (CSH1) or a fragment thereof; and
xii. a ligand that binds to progestagen-associated endometrial protein (PAEP) or a fragment thereof,
wherein at least one of the ligands is covalently or non-covalently joined to a detectable label or immobilized upon a substrate.

11. A diagnostic reagent or kit for use in diagnosing an ectopic pregnancy in a mammalian subject comprising a set of ligands, the ligands consisting of:
i. a ligand that binds Isthmin2 (ISM2),
ii. a ligand that binds the pro-domain or extracellular (EC) domain of ADAM12,
iii. a ligand that binds pregnancy specific beta-1 glycoprotein isoform 7 (PSG7),
iv. a ligand that binds pregnancy specific beta-1 glycoprotein isoform 11 (PSG11),
v. a ligand that binds pregnancy specific beta-1 glycoprotein isoform 9 (PSG9), and
vi. a ligand that binds pregnancy specific beta-1 glycoprotein isoform 2 (PSG2);
wherein at least one of the ligands is covalently or non-covalently joined with a detectable label or immobilized upon a substrate.

12. A diagnostic reagent or kit for use in diagnosing an ectopic pregnancy in a mammalian subject comprising a set of ligands, the set of ligands consisting of:
(i) a ligand that that binds to Isthmin2 (ISM2),
(ii) a ligand that binds to the pro-domain or extracellular (EC) domain of ADAM12, and a ligand that that binds to a peptide or protein selected from:
iii. pregnancy specific beta-1 glycoprotein isoform 7 (PSG7),
v. pregnancy specific beta-1 glycoprotein isoform 11 (PSG11),
v. pregnancy specific beta-1 glycoprotein isoform 9 (PSG9), and
vi. pregnancy specific beta-1 glycoprotein isoform 2 (PSG2),
wherein at least one of the ligands is covalently or non-covalently joined with a detectable label or immobilized upon a substrate.

* * * * *